(12) United States Patent
Penning et al.

(10) Patent No.: US 9,181,246 B2
(45) Date of Patent: Nov. 10, 2015

(54) PYRROLOPYRIDINE INHIBITORS OF KINASES

(71) Applicant: AbbVie Inc., North Chicago, IL (US)

(72) Inventors: Thomas D. Penning, Elmhurst, IL (US);
Keith W. Woods, Libertyville, IL (US);
Chunqiu Lai, Libertyville, IL (US);
Alan S. Florjancic, Kenosha, WI (US);
Yunsong Tong, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/444,540

(22) Filed: Jul. 28, 2014

(65) Prior Publication Data

US 2014/0357616 A1    Dec. 4, 2014

Related U.S. Application Data

(62) Division of application No. 13/086,546, filed on Apr. 14, 2011, now Pat. No. 8,822,446.

(60) Provisional application No. 61/325,591, filed on Apr. 19, 2010.

(51) Int. Cl.
| | |
|---|---|
| A61K 31/395 | (2006.01) |
| A61K 31/505 | (2006.01) |
| A61K 31/535 | (2006.01) |
| A61K 31/44 | (2006.01) |
| C07D 239/02 | (2006.01) |
| C07D 401/04 | (2006.01) |
| C07D 279/10 | (2006.01) |
| C07D 471/04 | (2006.01) |

(52) U.S. Cl.
CPC .................................. C07D 471/04 (2013.01)

(58) Field of Classification Search
CPC .. C07D 471/04; C07D 239/02; C07D 401/04; C07D 279/10; A61K 31/395; A61K 31/505; A61K 31/535; A61K 31/44
USPC .............. 514/210.18, 272, 273, 228.2, 234.5, 514/300; 544/321, 320, 123, 127, 58.6; 546/113
See application file for complete search history.

(56) References Cited

U.S. PATENT DOCUMENTS

| | | | |
|---|---|---|---|
| 2009/0253679 A1 | 10/2009 | Leroy et al. | |
| 2011/0015172 A1 | 1/2011 | Penning et al. | |
| 2011/0015173 A1* | 1/2011 | Florjancic et al. | 514/210.18 |
| 2014/0357616 A1* | 12/2014 | Penning et al. | 514/210.18 |

FOREIGN PATENT DOCUMENTS

| | | |
|---|---|---|
| WO | 2007054508 A1 | 5/2007 |
| WO | 2011008915 A1 | 1/2011 |

OTHER PUBLICATIONS

Cho W.H., et al., "CDC7 Kinase Phosphorylates Serine Residues Adjacent to Acidic Amino Acids in the Minichromosome Maintenance 2 Protein," Proceedings of the National Academy of Sciences USA, 2006, vol. 103 (31), pp. 11521-11526.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Ermoli A., et al., "Cell Division Cycle 7 Kinase Inhibitors: 1H-pyrrolo[2,3-b]pyridines, Synthesis and Structure-activity Relationships," Journal of Medicinal Chemistry, 2009, vol. 52 (14), pp. 4380-4390.

Feng D., et al., "Inhibiting the Expression of DNA Replication-Initiation Proteins 25 Induces Apoptosis in Human Cancer Cells," Cancer Research, 2003, vol. 63 (21), pp. 7356-7364.

International Search Report and Written Opinion for Application No. PCT/US2011/032464, mailed on Jul. 6, 2011, 12 pages.

Kim J.M., et al., "Functions of Mammalian Cdc7 Kinase in Initiation/Monitoring of DNA Replication and Development," Mutation Research, 2003, vol. 532 (1-2), pp. 29-40.

Kim J.M., et al., "Genetic Dissection of Mammalian Cdc7 Kinase: Cell Cycle 20 and Developmental Roles," Cell Cycle, 2004, vol. 3 (3), pp. 300-304.

Lau E., et al., "Is There a Pre-RC Checkpoint that Cancer Cells Lack", Cell Cycle, 2006, vol. 5 (15), pp. 1602-1606.

Lau E., et al., "The Functional Role of Cdc6 in S-G2/M in Mammalian Cells," EMBO Reports, 2006, vol. 7 (4), pp. 425-430.

Lau E., et al., "The Role of Pre-Replicative Complex (pre-RC) Components in Oncogenesis," Faseb Journal, 2007, vol. 21 (14), pp. 3786-3794.

Montagnoli A., et al., "Cdc7 Inhibition Reveals a p53-Dependent Replication Checkpoint that is Defective in Cancer Cells," Cancer Research, 2004, vol. 64 (19), pp. 7110-7116.

Montagnoli A., et al., "Identification of Mcm2 Phosphorylation Sites by S-Phase-Regulating Kinases," The Journal of Biological Chemistry, 2006, vol. 281 (15), pp. 10281-10290.

Stillman B., "Origin Recognition and the Chromosome Cycle," FEBS Letters, 2005, vol. 579 (4), pp. 877-884.

(Continued)

*Primary Examiner* — James O Wilson
*Assistant Examiner* — Ebenezer O Sackey
(74) *Attorney, Agent, or Firm* — Changxia Sun

(57) ABSTRACT

The present invention relates to compounds of formula (I) or pharmaceutical acceptable salts,

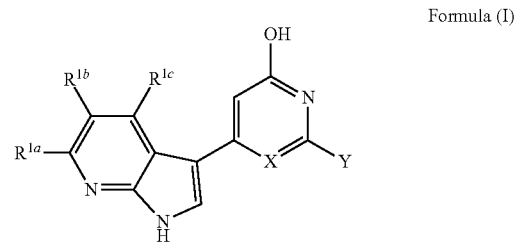

Formula (I)

wherein $R^{1a}$, $R^{1b}$, $R^{1c}$, X, and Y are defined in the description. The present invention relates also to compositions containing said compounds which are useful for inhibiting kinases such as Cdc7 and methods of treating diseases such as cancer.

21 Claims, No Drawings

(56) References Cited

OTHER PUBLICATIONS

Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.

Tse, C. et al., "ABT-263: A Potent and Orally Bioavailable Bcl-2 Family Inhibitor," Cancer Research, 2008, vol. 68 (9), pp. 3421-3428—Including Supplementary Data.

Tsuji T., et al., "Essential Role of Phosphorylation of MCM2 by Cdc7/Dbf4 in the Initiation of DNA Replication in Mammalian Cells," Molecular Biology of the Cell, 2006, vol. 17 (10), pp. 4459-4472.

\* cited by examiner

PYRROLOPYRIDINE INHIBITORS OF KINASES

CROSS-REFERENCE TO RELATED APPLICATIONS

This application is a divisional application of U.S. patent application Ser. No. 13/086,546 filed Apr. 14, 2011, which claims priority to U.S. Provisional Application Ser. No. 61/325,591 filed Apr. 19, 2010, both of which are incorporated by reference in their entirety.

BACKGROUND OF THE INVENTION

Eukaryotic cells divide by a directed, step-wise process referred to as the cell cycle. Cells must first replicate their DNA in S phase before separating their sister chromatids in mitosis (karyokinesis) and splitting off into two daughter cells (cytokinesis). In mammalian cells, DNA replication must be initiated at multiple sites (replication origins) throughout the genome to ensure that all the genetic material is duplicated prior to mitosis. To maintain genome integrity, DNA must be replicated only once per cell cycle, and so this process is highly regulated and governed by checkpoints. Before replication is initiated, origins must be licensed through the formation of pre-replication complexes (pre-RCs) in early G1. Formation of pre-RCs involves the step-wise binding of the origin recognition complex (ORC) to origins followed by the binding of the loading factors Cdc6 and Cdt1. These proteins then recruit the putative DNA replicative helicase complex, MCM2-7. Once this pre-RC is formed, replication initiation requires the activation of S-phase-promoting serine/threonine kinases, Cyclin/Cdks and Cdc7/Dbf4. These kinases consist of an enzymatic sub-unit (CDKs and Cdc7) and a regulatory sub-unit (Cyclins for CDKs; Dbf4 or Drf1 for Cdc7). They phosphorylate multiple MCMs in pre-RCs in a sequential manner, thereby activating the helicase and recruiting other DNA replication factors (Cdc45, GINS complex, etc.) for DNA synthesis (for reviews, see Kim et al., 2003; Kim et al., 2004; Lau et al., 2006; Lau et al., 2007; Stillman, 2005). MCM2 Serine-40 and Serine-53 are well-characterized phosphorylation sites for Cdc7/Dbf4 (Cho et al., 2006; Montagnoli et al., 2006; Tsuji et al., 2006).

Inhibiting regulators of replication initiation, such as Cdc6, Cdc7/Dbf4 or Cdc7/Drf1, has lethal consequences in cancerous cells, whereas normal cells are able to arrest and resume normal divisions once initiation activity is restored (Feng et al., 2003; Montagnoli et al., 2004; see Lau and Jiang, 2006, for review). Small molecule inhibitors of the protein kinase Cdc7 are thus attractive candidates for therapeutic intervention in cancer, inflammation and other cell proliferative disorders.

SUMMARY OF THE INVENTION

The present invention has numerous embodiments. One embodiment of this invention, therefore, pertains to compounds that have formula (I)

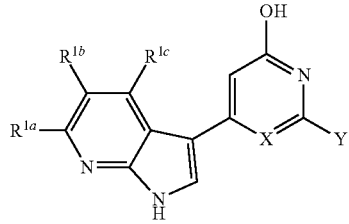

Formula (I)

wherein $R^{1a}$, $R^{1b}$, $R^{1c}$, X, and Y are as defined below and subsets therein.

Also provided are pharmaceutically acceptable compositions, comprising a therapeutically effective amount of a compound of formula (I) a pharmaceutically acceptable salt in combination with a pharmaceutically suitable carrier.

One embodiment is directed to a method of treating cancer in a mammal comprising administering thereto a therapeutically acceptable amount of a compound or pharmaceutically acceptable salt of formula (I). In yet another embodiment pertains to a method of decreasing tumor volume in a mammal comprising administering thereto a therapeutically acceptable amount of a compound or pharmaceutically acceptable salt of formula (I).

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

ABBREVIATIONS AND DEFINITIONS

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O). The term "oxy" (alone or in combination with another term(s)) means an ether substituent, and may be depicted as —O—.

The term "alkylhydroxy" (alone or in combination with another term(s)) means alkyl-OH.

The term "alkylamino" (alone or in combination with another term(s)) means alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$7.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl;

6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$— prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

In one aspect, the present invention provides compounds of formula (I):

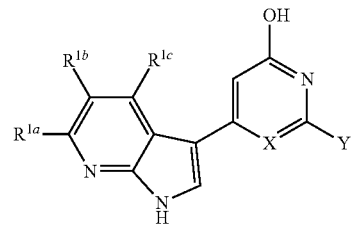

Formula (I)

wherein $R^{1a}$, $R^{1b}$, and $R^{1c}$ are independently hydrogen, hydroxy, nitro, halogen, cyano, trifluoromethyl, trifluoromethoxy, $C_{1-4}$-alkyl, —$OR^a$, —$NR^bR^c$; —$C(O)OR^a$, —$C(O)NR^bR^c$, —$NR^bC(O)R^c$, —$NHC(O)NHR^b$, or —$NHSO_2R^a$;

X is N or $CR^2$;

$R^2$ is hydrogen or $C_{1-4}$-alkyl;

Y is $NR^3R^4$, $NR^6C(O)R^7$, $NR^6SO_2R^7$, aryl, or heterocyclyl, wherein the aryl and heterocyclyl are optionally substituted with one or more $R^5$;

$R^3$ is hydrogen, $C_{1-8}$-alkyl, $C_{2-8}$-alkenyl, $C_{2-8}$-alkynyl, $C_{3-8}$-cycloalkyl, $C_{3-8}$-cycloalkyl-($C_{1-8}$-alkyl)-, heterocycloalkyl, heterocycloalkyl-($C_{1-8}$-alkyl)-, aryl, aryl-($C_{1-8}$-alkyl)-, heteroaryl-, or heteroaryl-($C_{1-8}$-alkyl), wherein (a) the $R^3C_{1-8}$-alkyl, $C_{2-8}$-alkenyl, $C_{2-8}$-alkynyl substituents, alone or as part of another group, are optionally substituted with one or more substituents selected from the group consisting of halogen, cyano, nitro, —$OR^a$, —$C(O)R^a$, —$C(O)OR^a$, —$OC(O)R^a$, —$NR^bR^c$, —$NR^bC(O)R^a$, —$NHC(O)NHR^h$, —$C(O)NR^bR^c$, —$NHSO_2R^a$, and —$SO_2NR^bNR^c$; and (b) the $R^3C_{3-8}$-cycloalkyl, heterocycloalkyl, aryl, and heteroaryl, alone or as part of another group, are optionally substituted with one or more $R^5$;

$R^4$ is hydrogen or $C_{1-8}$-alkyl; wherein the $C_{1-8}$-alkyl is optionally substituted with one or more substituents selected from the group consisting of halogen, cyano, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$;

$R^5$ is selected from the group consisting of $C_{1-8}$-alkyl, $C_{2-8}$-alkenyl, $C_{2-8}$-alkynyl, aryl, heterocyclyl, halogen, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$NHSO_2R^e$, —$C(O)NR^eR^f$, —$SR^d$, —$S(O)R^d$, —$SO_2R^d$, —$SO_2NR^eNR^f$, —$B(OH)_2$, —$CF_3$, —$CF_2CF_3$, —$OCF_3$, and —$OCF_2CF_3$ wherein (a) the $R^5C_{1-8}$-alkyl, $C_{2-8}$-alkenyl, $C_{2-8}$-alkynyl, substituents are optionally substituted with one or more substituents selected from the group consisting of aryl, heterocyclyl, $C_{3-8}$-cycloalkyl, halogen, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$C(O)NR^eR^f$; and wherein (b) the $R^5$ aryl or heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, —$OR^g$, —$C(O)R^g$, —$C(O)OR^g$, —$OC(O)R^g$, —$NR^hR^i$, —$NR^hC(O)R^g$, —$NHC(O)NHR^h$, —$NHSO_2R^g$, —$C(O)NR^hR^i$, —$SR^g$, —$S(O)R^g$, —$SO_2R^g$, —$SO_2NR^hNR^i$, —$CF_3$, —$CF_2CF_3$, —$OCF_3$, and —$OCF_2CF_3$;

$R^6$ is hydrogen or $C_{1-8}$-alkyl;

$R^7$ is $C_{1-8}$-alkyl, $C_{2-8}$-alkenyl, $C_{2-8}$-alkynyl, $C_{3-8}$-cycloalkyl, $C_{3-8}$-cycloalkyl-($C_{1-8}$-alkyl)-, heterocycloalkyl, heterocycloalkyl-($C_{1-8}$-alkyl)-, aryl, aryl-($C_{1-8}$-alkyl)-, heteroaryl-, or heteroaryl-($C_{1-8}$-alkyl)-, wherein (a) the $R^7C_{1-8}$-alkyl, $C_{2-8}$-alkenyl, $C_{2-8}$-alkynyl substituents, alone or as part of another group, are optionally substituted with one or more substituents selected from the group consisting of halogen, cyano, nitro, —OR$^a$, —C(O)Ra, —C(O)OR$^a$, —OC(O)R$^a$, —NR$^b$R$^c$, —NR$^b$C(O)R$^a$, —NHC(O)NHR$^b$, —C(O)NR$^b$R$^c$, —NHSO$_2$R$^a$, —SO$_2$NR$^b$NR$^c$, and aryl; and (b) the R$^7$C$_{3-8}$-cycloalkyl, heterocycloalkyl, aryl, and heteroaryl, alone or as part of another group, are optionally substituted with one or more R$^5$;

R$^a$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, heterocyclyl, C$_{3-8}$-cycloalkyl, halogen, cyano, hydroxy, C$_{1-8}$-alkoxy, —NH$_2$, —NH(C$_{1-8}$-alkyl), —O(C$_{1-8}$-alkyl)NH$_2$, and —N(C$_{1-8}$-alkyl)$_2$;

R$^b$ and R$^c$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^b$ and R$^c$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^d$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, aryl-(C$_{1-8}$-alkyl)-, heterocyclyl, C$_{3-8}$-cycloalkyl, halogen, cyano, hydroxy, C$_{1-8}$-alkoxy, —NH$_2$; —NH(C$_{1-8}$-alkyl), and —N(C$_{1-8}$-alkyl)$_2$; wherein the aryl, aryl-(C$_{1-8}$-alkyl)-, heterocyclyl, and C$_{3-8}$-cycloalkyl, alone or as part of another group, are optionally substituted with one or more substituents independently selected from the group consisting of C$_{1-8}$-alkyl, aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^e$ and R$^f$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^e$ and R$^f$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^g$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^h$ and R$^i$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^h$ and R$^i$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

or a pharmaceutically acceptable salt thereof.

In one embodiment of formula (I), R$^{1a}$, R$^{1b}$, and R$^{1c}$ are hydrogen. In another embodiment of formula (I), R$^{1b}$ and R$^{1c}$ are hydrogen and R$^{1a}$ is hydroxy, nitro, halogen, cyano, trifluoromethyl, trifluoromethoxy, C$_{1-4}$-alkyl, —OR$^a$, —NR$^b$R$^c$, —C(O)OR$^a$, —C(O)NR$^b$R$^c$, —NR$^b$C(O)R$^c$, —NHC(O)NHR$^b$, or —NHSO$_2$R$^a$. In another embodiment of formula (I), R$^{1a}$ and R$^{1c}$ are hydrogen and R$^{1b}$ is hydroxy, nitro, halogen, cyano, trifluoromethyl, trifluoromethoxy, C$_{1-4}$-alkyl, —OR$^a$, —NR$^b$R$^c$, —C(O)OR$^a$, —C(O)NR$^b$R$^c$, —NR$^b$C(O)R$^c$, —NHC(O)NHR$^b$, or —NHSO$_2$R$^a$. In another embodiment of formula (I), R$^{1c}$ is hydrogen and R$^{1a}$ and R$^{1b}$ are each independently hydroxy, nitro, halogen, cyano, trifluoromethyl, trifluoromethoxy, C$_{1-4}$-alkyl, —OR$^a$, —NR$^b$R$^c$, —C(O)OR$^a$, —C(O)NR$^b$R$^c$, —NR$^b$C(O)R$^c$, —NHC(O)NHR$^b$, or —NHSO$_2$R$^a$.

In one embodiment of formula (I), X is N.

In another embodiment of formula (I), X is CR$^2$ wherein R$^2$ is C$_{1-4}$-alkyl. In yet another embodiment of formula (I), X is CR$^2$ wherein R$^2$ is hydrogen.

In one embodiment of formula (I), Y is aryl, which is optionally substituted with one or more R$^5$. In another embodiment of formula (I), the aryl is unsubstituted. In another embodiment of formula (I), Y is phenyl or naphthyl, and the phenyl or naphthyl is substituted with one, two, or three substituents independently selected from the group consisting of C$_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$. In another embodiment of formula (I), Y is phenyl, and the phenyl is substituted with one, two, or three substituents independently selected from the group consisting of C$_{1-8}$-alkyl, halogen, —OR$^d$, —SO$_2$R$^d$, —OCF$_3$, and —CF$_3$.

In one embodiment of formula (I), Y is heterocylyl, which is optionally substituted with one or more R$^5$. In another embodiment of formula (I), the heterocyclyl is unsubstituted. In one embodiment of formula (I), Y is piperidine, thiomorpholine, morpholine, benzodioxolyl, thienyl, pyridinyl, or pyrazolyl, wherein the piperidine, thiomorpholine, morpholine, benzodioxolyl, thienyl, pyridinyl, or pyrazolyl is unsubstituted. In another embodiment of formula (I), Y is piperidine, thiomorpholine, morpholine, benzodioxolyl, thienyl, pyridinyl, or pyrazolyl, and the piperidine, thiomorpholine, morpholine, benzodioxolyl, thienyl, pyridinyl, or pyrazolyl is substituted with one, two, or three substituents independently selected from the group consisting of C$_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$. In another embodiment of formula (I), Y is a piperidine, thiomorpholine, morpholine, benzodioxolyl, thienyl, pyridinyl, or pyrazolyl, and the piperidine, thiomorpholine, morpholine, benzodioxolyl, thienyl, pyridinyl, or pyrazolyl is substituted with one, two, or three substituents independently selected from the group consisting of C$_{1-8}$-alkyl, halogen, —OR$^d$, and —C(O)OR$^d$.

In one embodiment of formula (I), Y is heterocycloalkyl, which is optionally substituted with one or more R$^5$. In another embodiment of formula (I), the heterocycloalkyl is unsubstituted. In another embodiment of formula (I), Y is piperidine, thiomorpholine, or morpholine, and the piperidine, thiomorpholine, or morpholine is unsubstituted. In another embodiment of formula (I), the piperidine, thiomorpholine, or morpholine, is substituted with one, two, or three substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$. In another embodiment of formula (I), Y is a piperidine, thiomorpholine, or morpholine, and the piperidine, thiomorpholine, or morpholine is substituted with one, two, or three substituents independently selected from the group consisting of $C_{1-8}$-alkyl, —$OR^d$, and —$C(O)OR^d$.

In one embodiment of formula (I), Y is heteroaryl, which is optionally substituted with one or more $R^5$. In another embodiment of formula (I), the heteroaryl is unsubstituted. In another embodiment, Y is thienyl, pyridinyl, or pyrazolyl, wherein the thienyl, pyridinyl, or pyrazolyl is unsubstituted. In another embodiment of formula (I), the thienyl, pyridinyl, or pyrazolyl is substituted with one, two, or three substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$. In another embodiment, Y is thienyl, pyridinyl, or pyrazolyl, and the thienyl, pyridinyl, or pyrazolyl is substituted with one, two, or three substituents independently selected from the group consisting of halogen and $OR^d$.

In one embodiment of formula (I), Y is $NR^3R^4$.

In one embodiment of formula (I), $R^3$ is $C_{1-8}$-alkyl. In another embodiment of formula (I), $R^3$ is $C_{1-8}$-alkyl which is unsubstituted. In another embodiment of formula (I), $R^3$ is $C_{1-8}$-alkyl which is substituted with one or more substituents selected from the group consisting of halogen, cyano, nitro, —$OR^a$, —$C(O)R^a$, —$C(O)OR^a$, —$OC(O)Ra$, —$NR^bR^c$, $NR^bC(O)R^a$, —$NHC(O)NHR^b$, —$C(O)NR^bR^c$, —$NHSO_2R^a$, and —$SO_2NR^bNR^c$. In another embodiment of formula (I), $R^3$ is $C_{1-8}$-alkyl which is substituted with one or two substituents selected from the group consisting of —$OR^a$, and —$NR^bR^c$. In another embodiment of formula (I), $R^3$ is $C_{1-8}$-alkyl which is substituted with one or two substituents selected from the group consisting of —$OR^a$, and —$NR^bR^c$ wherein $R^a$, $R^b$, and $R^c$ are independently selected from the group consisting of hydrogen and $C_{1-8}$-alkyl. In another embodiment of formula (I), $R^3$ is $C_{1-8}$-alkyl which is substituted with one or two substituents selected from the group consisting of —OH, $OCH_3$, —$OCH_2CH_2OCH_2CH_2NH_2$, and —$NHCH_3$.

In another embodiment of formula (I), $R^3$ is aryl or heteroaryl, which is optionally substituted with one or more $R^5$. In another embodiment of formula (I), the aryl or heteroaryl is unsubstituted.

In one embodiment of formula (I), $R^3$ is phenyl, which is substituted with one, two or three $R^5$, and $R^5$ is selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$, wherein (a) the $R^5C_{1-8}$-alkyl substituent is optionally substituted with —$OR^d$. In one embodiment of formula (I), $R^3$ is phenyl, which is substituted with one, two, or three $R^5$, and $R^5$ is $OR^d$, wherein $R^d$ is $C_{1-8}$-alkyl.

In another embodiment of formula (I), $R^3$ is a 5-7-membered heteroaryl optionally substituted with one or more $R^5$. In another embodiment of formula (I), $R^3$ is 5-7 membered heteroaryl which is unsubstituted. In yet another embodiment of formula (I), $R^3$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, which is unsubstituted. In another embodiment of formula (I), $R^3$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, which is substituted with one, two or three $R^5$, and $R^5$ is selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$.

In another embodiment of formula (I), $R^3$ is heterocloalkyl, which is optionally substituted with one or more $R^5$. In another embodiment of formula (I), $R^3$ is heterocycloalkyl, which unsubstituted. In one embodiment of formula (I), $R^3$ is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, which is unsubstituted. In one embodiment of formula (I), $R^7$ is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, which is substituted with one, two, or three $R^5$, and $R^5$ is selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$, wherein (a) the $R^5$ $C_{1-8}$-alkyl substituent is optionally substituted with —$OR^d$. In one embodiment of formula (I), $R^3$ is pyrrolidinyl, tetrahydrofuryl, piperidinyl, or tetrahydropyranyl.

In another embodiment of formula (I), $R^3$ is cycloalkyl, which is optionally substituted with one or more $R^5$. In another embodiment of formula (I), $R^3$ is cycloalkyl, which unsubstituted. In one embodiment of formula (I), $R^3$ is cyclopentyl, cyclohexyl, and cycloheptyl, which is unsubstituted. In one embodiment of formula (I), $R^3$ is cyclopentyl, cyclohexyl, and cycloheptyl, which is substituted with one, two, or three $R^5$, and $R^5$ is selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$, wherein (a) the $R^5C_{1-8}$-alkyl substituent is optionally substituted with —$OR^d$. In one embodiment of formula (I), $R^3$ is cyclopentyl, cyclohexyl, and cycloheptyl, which is substituted with one, two, or three $R^5$, and $R^5$ is —$OR^d$, —$NR^eR^f$, —$NR^eC(O)R^d$, or —$NHSO_2R^e$, wherein $R^d$, at each occurrence, is selected from the group consisting of hydrogen, $C_{1-8}$-alkyl, heterocyclyl, and $C_{3-8}$-cycloalkyl, wherein the heterocyclyl is optionally substituted with one or more substituents independently selected from the group consisting of aryl-($C_{1-8}$-alkyl), wherein the aryl-($C_{1-8}$-alkyl), alone or as part of another group, is optionally substituted with one or more substituents independently selected from the group consisting of halogen, and $R^e$ and $R^f$, at each occurrence, are independently selected from the group consisting of hydrogen, and $C_{3-8}$-cycloalkyl.

In one embodiment of formula (I), $R^3$ is $C_{3-8}$-cycloalkyl ($C_{1-8}$-alkyl), heterocycloalkyl($C_{1-8}$-alkyl), aryl-($C_{1-8}$-alkyl), or heteroaryl($C_{1-8}$-alkyl), and the $R^3$ ($C_{1-8}$-alkyl)- is unsubstituted. In another embodiment of formula (I), where $R^3$ is $C_{3-8}$-cycloalkyl($C_{1-8}$-alkyl), heterocycloalkyl($C_{1-8}$-alkyl), aryl-($C_{1-8}$-alkyl), or heteroaryl ($C_{1-8}$-alkyl), the $R^3$ ($C_{1-8}$-alkyl)- is optionally substituted with one or two substituents selected from the group consisting of —$OR^a$ and —$NR^bR^c$.

In one embodiment of formula (I), $R^3$ is $C_{3-8}$-cycloalkyl ($C_{1-8}$-alkyl), heterocycloalkyl($C_{1-8}$-alkyl), aryl-($C_{1-8}$-alkyl), or heteroaryl($C_{1-8}$-alkyl), the —($C_{1-8}$-alkyl)- is ($C_{1-8}$-alkyl)-, —($C_2$-alkyl)-, or ($C_3$-alkyl)-. In one embodiment of formula (I), $R^3$ is ($C_1$-alkyl)-.

In another embodiment of formula (I), $R^3$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), wherein the $R^3C_{3-8}$-cycloalkyl, heterocycloalkyl, aryl, and heteroaryl are optionally substituted. In another embodiment of formula (I), $R^3$ is $C_{3-8}$-cycloalkyl($C_{1-8}$-alkyl), heterocycloalkyl ($C_{1-8}$-alkyl), aryl-($C_{1-8}$-alkyl), or heteroaryl($C_{1-8}$-alkyl), wherein the $R^3C_{3-8}$-cycloalkyl, heterocycloalkyl, aryl, and heteroaryl are unsubstituted. In another embodiment of formula (I), $R^3$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), wherein the $R^3C_{3-8}$-cycloalkyl, heterocycloalkyl, aryl, and heteroaryl are substituted with one or more $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, or —$OCF_3$, wherein (a) the $R^5C_{1-8}$-alkyl substituent is optionally substituted with one or more —$OR^d$. In another embodiment of formula (I), $R^3$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), wherein the $R^3C_{3-8}$-cycloalkyl, heterocycloalkyl, aryl, and heteroaryl are substituted with one, two, or three $R^5$, and $R^5$ is selected from the group consisting of halogen, —OH, and —$CF_3$.

In one embodiment of formula (I), $R^3$ is $C_{3-8}$-cycloalkyl ($C_{1-8}$-alkyl), the $C_{3-8}$-cycloalkyl is an optionally substituted cyclobutyl, cyclopentyl, or cyclohexyl.

In one embodiment of formula (I), where $R^3$ is heterocycloalkyl($C_{1-8}$-alkyl), the heterocycloalkyl is an optionally substituted 5-7 membered heterocycloalkyl. In another embodiment of formula (I), the $R^3$ heterocyclcoalkyl is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In another embodiment of formula (I), wherein $R^3$ is heterocycloalkyl($C_{1-8}$-alkyl), the heterocycloalkyl is an optionally substituted pyrrolidinyl, tetrahydrofuryl, piperidinyl, or tetrahydropyranyl.

In one embodiment, wherein $R^3$ is aryl($C_{1-8}$-alkyl), the aryl is an optionally substituted phenyl.

In one embodiment, wherein $R^3$ is heteroaryl($C_{1-8}$-alkyl), the heteroaryl is an optionally substituted 5-7-membered heteroaryl. In yet another embodiment, where $R^3$ is heteroaryl ($C_{1-8}$-alkyl), the $R^3$ heteroaryl is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl. In yet another embodiment, where $R^3$ is heteroaryl($C_{1-8}$-alkyl), the $R^3$ heteroaryl is imidazolyl.

In one embodiment of formula (I), $R^4$ is hydrogen. In another embodiment of formula (I), $R^4$ is an unsubstituted branched or straight chain $C_{1-8}$ alkyl. In yet another embodiment of formula (I), $R^4$ is methyl, ethyl, propyl, isopropyl, n-butyl, sec-butyl, or t-butyl. In another embodiment of formula (I), $R^4$ is methyl. In another embodiment of formula (I), $R^4$ is a substituted branched or straight chain $C_{1-8}$ alkyl, wherein the $C_{1-8}$-alkyl is substituted with $OR^a$ wherein $R^a$ is selected from the group consisting of H and $C_{1-8}$-alkyl. In another embodiment of formula (I), $R^4$ is a substituted branched or straight chain $C_{1-8}$ alkyl, wherein the $C_{1-8}$-alkyl is substituted with $OCH_3$.

In another embodiment of formula (I), $NR^3R^4$ is selected from the group consisting of

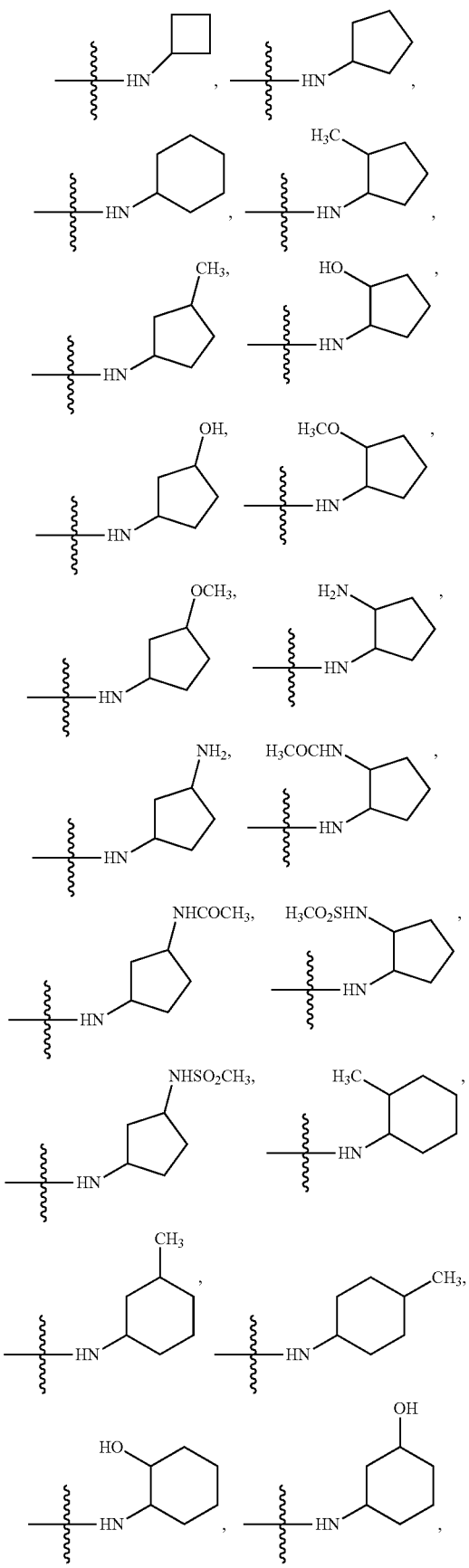

-continued
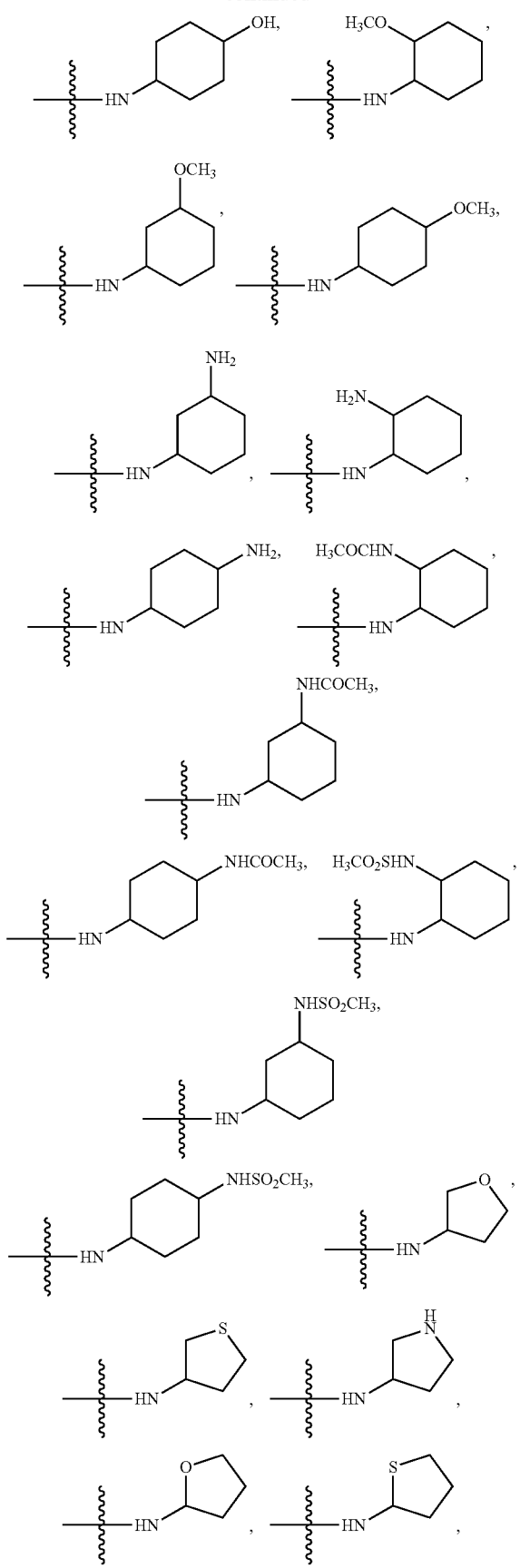
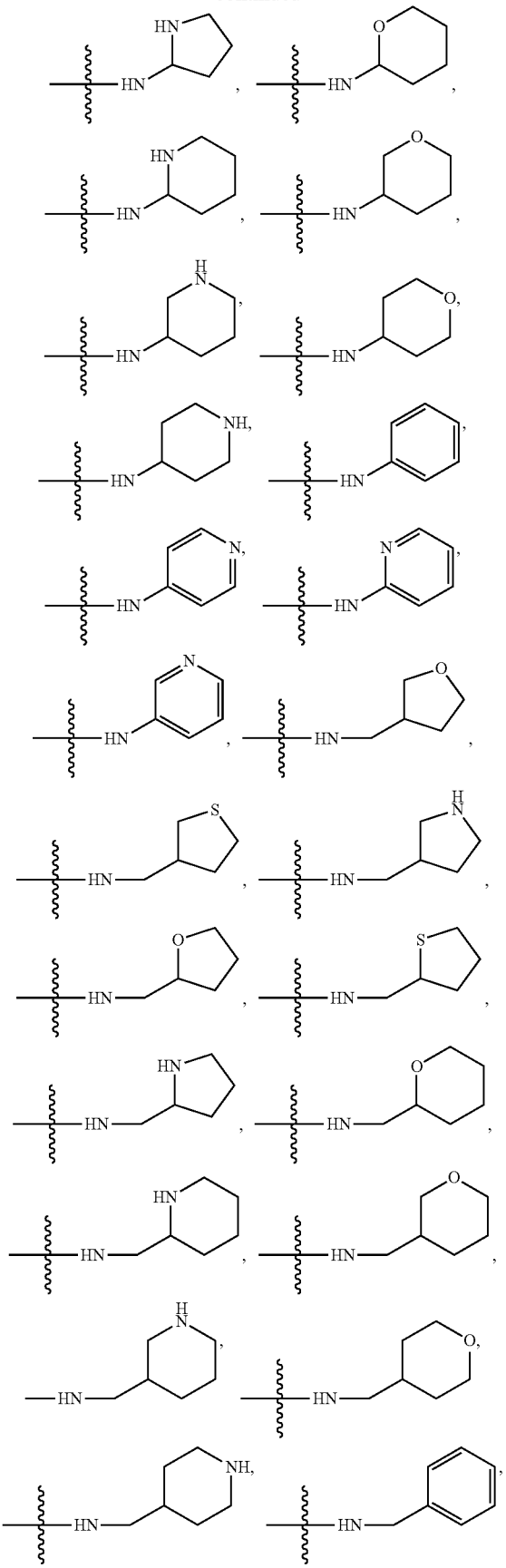

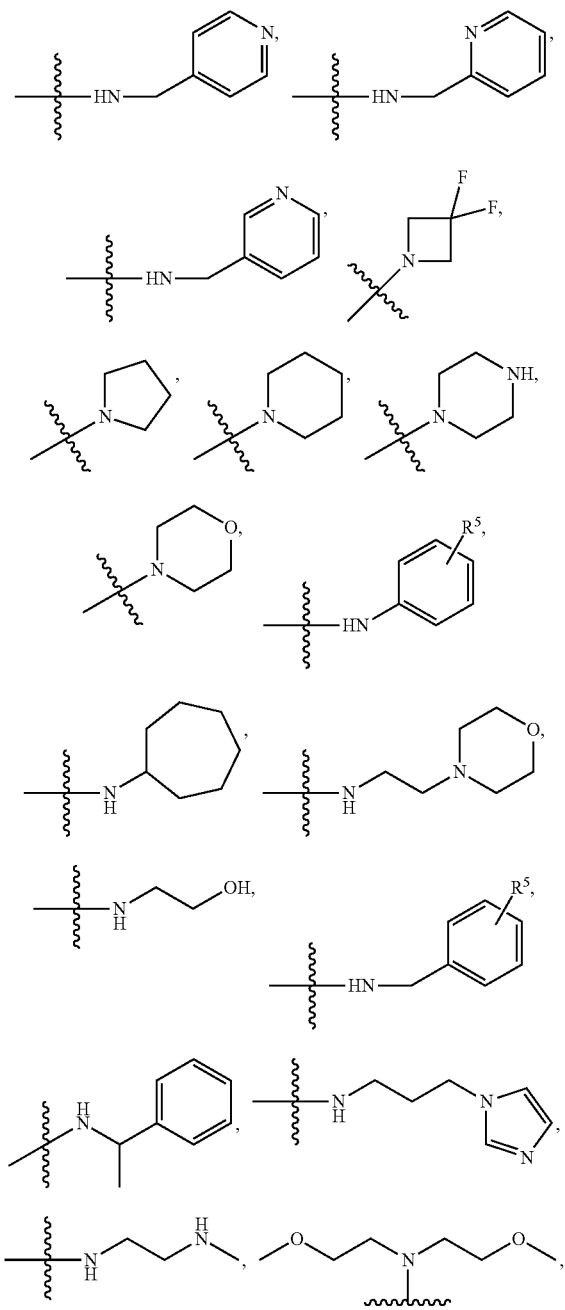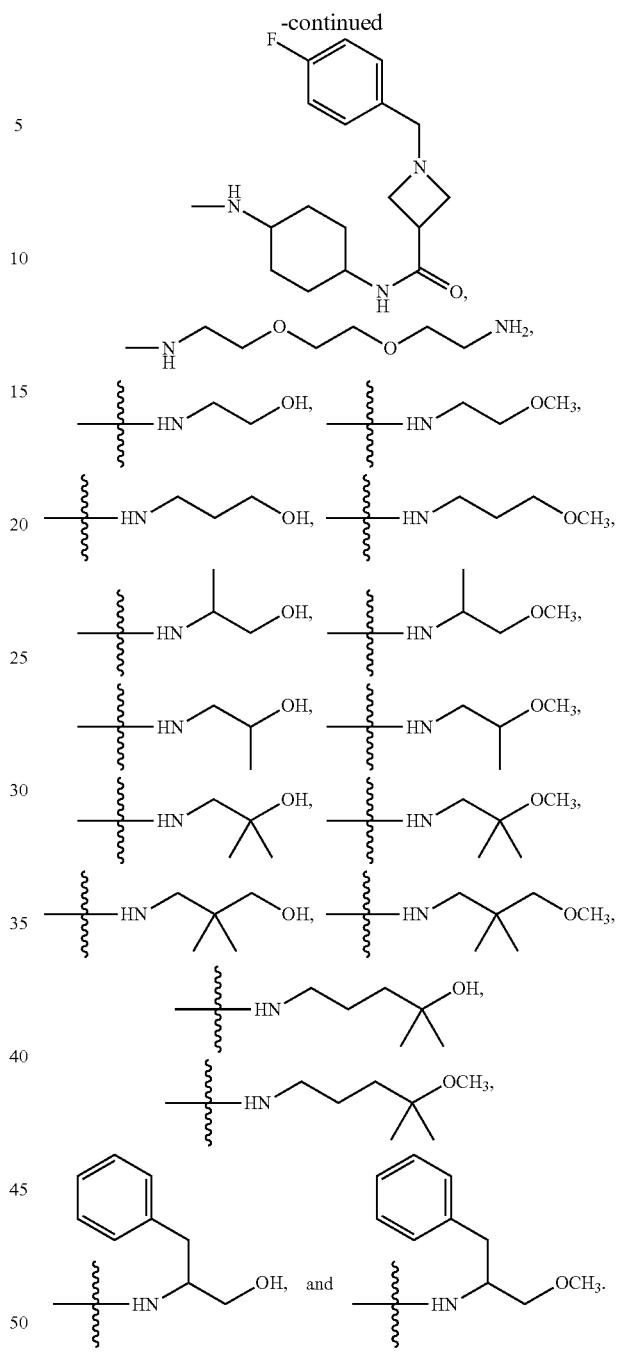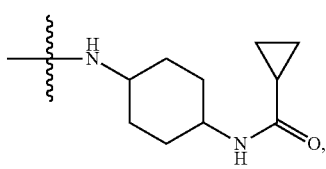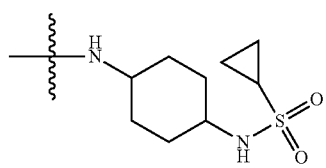

In another embodiment of formula (I), Y is $NR^6C(O)R^7$ or $NR^6SO_2R^7$.

In one embodiment of formula (I), $R^6$ is hydrogen. In another embodiment of formula (I), $R^6$ is an unsubstituted branched or straight chain $C_{1-4}$-alkyl.

In one embodiment of formula (I), $R^7$ is optionally substituted $C_{1-8}$-alkyl. In one embodiment of formula (I), the $R^7$ $C_{1-8}$-alkyl is unsubstituted. In another embodiment of formula (I), the $R^7 C_{1-8}$-alkyl is substituted with one or more substituents independently selected from the groups consisting of halogen, —$OR^a$, $NR^bR^c$, —$NR^bC(O)R^a$, —$NHSO_2R^a$, —$SO_2NR^bNR^c$, and aryl, wherein $R^a$, $R^b$, and $R^e$ are independently selected from the group consisting of H and $C_{1-8}$-alkyl. In another embodiment of formula (I), the $R^7C_{1-8}$-alkyl is optionally substituted with one or two substituents selected from the group consisting of hydroxy, methoxy, ethoxy, amino, —NHCH$_3$, —NHCOCH$_3$, —NHSO$_2$CH$_3$, and SO$_2$NHCH$_3$.

In another embodiment of formula (I), $R^7$ is aryl or heteroaryl, which is optionally substituted with one or more $R^5$. In another embodiment of formula (I), the aryl or heteroaryl is unsubstituted.

In one embodiment of formula (I), $R^7$ is phenyl, which is substituted with one, two or three $R^5$, and $R^5$ is selected from the group consisting of $C_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$, wherein (a) the $R^5C_{1-8}$-alkyl substituent is optionally substituted with —OR$^d$. In one embodiment of formula (I), $R^3$ is phenyl, which is substituted with one, two, or three $R^5$, and $R^5$ is OR$^d$, wherein $R^d$ is $C_{1-8}$-alkyl.

In another embodiment of formula (I), $R^7$ is a 5-7-membered heteroaryl optionally substituted with one or more $R^5$. In another embodiment of formula (I), $R^7$ is 5-7 membered heteroaryl which is unsubstituted. In yet another embodiment of formula (I), $R^7$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, which is unsubstituted. In one embodiment of formula (I), $R^7$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, which is substituted with one, two or three $R^5$, and $R^5$ is selected from the group consisting of $C_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$. In one embodiment of formula (I), the $R^7$ heteroaryl is pyridinyl.

In another embodiment of formula (I), $R^7$ is heterocycloalkyl, which is optionally substituted with one or more $R^5$. In another embodiment of formula (I), $R^7$ is heterocycloalkyl, which unsubstituted. In one embodiment of formula (I), $R^7$ is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, which is unsubstituted. In one embodiment of formula (I), $R^7$ is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, which is substituted with one, two, or three $R^5$, and $R^5$ is selected from the group consisting of $C_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$, wherein (a) the $R^5C_{1-8}$-alkyl substituent is optionally substituted with —OR$^d$. In one embodiment of formula (I), $R^7$ is pyrrolidinyl, tetrahydrofuryl, piperidinyl, or tetrahydropyranyl.

In another embodiment of formula (I), $R^7$ is cycloalkyl, which is optionally substituted with one or more $R^5$. In another embodiment of formula (I), $R^7$ is cycloalkyl, which unsubstituted. In one embodiment of formula (I), $R^7$ is cyclopentyl, cyclohexyl, and cycloheptyl, which is unsubstituted. In one embodiment of formula (I), $R^7$ is cyclopentyl, cyclohexyl, and cycloheptyl, which is substituted with one, two, or three $R^5$, and $R^5$ is selected from the group consisting of $C_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$, wherein (a) the $R^5C_{1-8}$-alkyl substituent is optionally substituted with —OR$^d$. In one embodiment of formula (I), $R^7$ is cyclopentyl, cyclohexyl, and cycloheptyl, which is substituted with one, two, or three $R^5$, and $R^5$ is —OR$^d$, —NR$^e$R$^f$, —NR$^e$C(O)R$^d$, or —NHSO$_2$R$^e$.

In one embodiment of formula (I), $R^7$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), and the $R^7$ ($C_{1-8}$-alkyl)- is unsubstituted. In one embodiment of formula (I), where $R^7$ is $C_{3-8}$-cycloalkyl($C_{1-8}$-alkyl), heterocycloalkyl($C_{1-8}$-alkyl), aryl-($C_{1-8}$-alkyl), or heteroaryl-($C_{1-8}$-alkyl), the $R^7$ ($C_{1-8}$-alkyl)- is optionally substituted with one or two substituents selected from the group consisting of —OR$^a$ and —NR$^b$R$^c$.

In one embodiment of formula (I), $R^7$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), the —($C_{1-8}$-alkyl)- is ($C_1$-alkyl)-, —($C_2$-alkyl)-, or ($C_3$-alkyl)-. In one embodiment of formula (I), $R^7$ is ($C_1$-alkyl)-.

In another embodiment of formula (I), $R^7$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), wherein the $R^7C_{3-8}$-cycloalkyl, heterocycloalkyl, aryl, and heteroaryl are optionally substituted. In another embodiment of formula (I), $R^7$ is $C_{3-8}$-cycloalkyl($C_{1-8}$-alkyl), heterocycloalkyl-($C_{1-8}$-alkyl), aryl-($C_{1-8}$-alkyl), or heteroaryl($C_{1-8}$-alkyl), wherein the $R^7C_{3-8}$-cycloalkyl, heterocycloalkyl, aryl, and heteroaryl are unsubstituted. In another embodiment of formula (I), $R^7$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), wherein the $R^7C_{3-8}$-cycloalkyl, heterocycloalkyl, aryl, and heteroaryl are substituted with one or more $C_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, or —OCF$_3$, wherein (a) the $R^5C_{1-8}$-alkyl substituent is optionally substituted with one or more —OR$^d$. In another embodiment of formula (I), $R^7$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), wherein the $R^3C_{3-8}$-cycloalkyl, heterocycloalkyl, aryl, and heteroaryl are substituted with one, two, or three $R^5$, and $R^5$ is selected from the group consisting of halogen, —OH, and —CF$_3$.

In one embodiment of formula (I), wherein $R^7$ is $C_{3-8}$-cycloalkyl($C_{1-8}$-alkyl), the $C_{3-8}$-cycloalkyl is an optionally substituted cyclobutyl, cyclopentyl, or cyclohexyl.

In one embodiment of formula (I), where $R^7$ is heterocycloalkyl($C_{1-8}$-alkyl), the heterocycloalkyl is an optionally substituted 5-7 membered heterocycloalkyl. In another embodiment of formula (I), the $R^7$ heterocyclcoalkyl is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In another embodiment of formula (I), wherein $R^7$ is heterocycloalkyl($C_{1-8}$-alkyl), the heterocycloalkyl is an optionally substituted pyrrolidinyl, tetrahydrofuryl, piperidinyl, or tetrahydropyranyl.

In one embodiment, wherein $R^7$ is aryl($C_{1-8}$-alkyl)-, the aryl is an optionally substituted phenyl.

In one embodiment, wherein $R^7$ is heteroaryl($C_{1-8}$-alkyl), the heteroaryl is an optionally substituted 5-7-membered heteroaryl. In yet another embodiment, where $R^7$ is heteroaryl($C_{1-8}$-alkyl), the $R^7$ heteroaryl is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl. In yet another embodiment, where $R^7$ is heteroaryl-($C_{1-8}$-alkyl)-, the $R^3$ heteroaryl is imidazolyl.

In another embodiment, the present invention provides compounds of formula (I) wherein $R^{1a}R^{1b}$, and $R^{1c}$ are hydrogen, X is N, Y is NR$^3$R$^4$, wherein $R^3$ is $C_{3-8}$-cycloalkyl, wherein the $C_{3-8}$-cycloalkyl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is $C_{3-8}$-cycloalkyl, wherein the $C_{3-8}$-cycloalkyl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is $NR^3R^4$, wherein $R^3$ is aryl, wherein the aryl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is aryl, wherein the aryl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is $NR^3R^4$, wherein $R^3$ is aryl-($C_{1-8}$-alkyl), wherein the aryl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is aryl-($C_{1-8}$-alkyl)-, wherein the aryl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is $NR^3R^4$, wherein $R^3$ is heterocycloalkyl, wherein the heterocycloalkyl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is heterocycloalkyl, wherein the heterocycloalkyl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein (a) the $C_{1-8}$-alkyl is optionally substituted with one or more —$OR^d$, and —$NHSO_2R^e$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is $NR^3R^4$, wherein $R^3$ is heterocycloalkyl-($C_{1-8}$-alkyl)-, wherein the heterocycloalkyl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is $CR^2$, $R^2$ is hydrogen, Y is heterocyclyl, wherein the heterocyclyl is optionally substituted with one or more substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is heterocyclyl, wherein the heterocyclyl is optionally substituted with one or more substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is $C_{1-8}$-alkyl, wherein the $R^3C_{1-8}$-alkyl is optionally substituted with one or more substituents selected from the group consisting of halogen, —$OR^a$, and —$NR^bR^c$; wherein $R^4$ is hydrogen or $C_{1-8}$-alkyl, and wherein $R^e$, $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is $NR^3R^4$, wherein $R^3$ is $C_{1-8}$-alkyl, wherein the $R^3C_{1-8}$-alkyl is optionally substituted with one or more substituents selected from the group consisting of halogen, —$OR^a$, and —$NR^bR^c$; wherein $R^4$ is hydrogen or $C_{1-8}$-alkyl, and wherein $R^e$, $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is $C_{1-8}$-alkyl, wherein the $R^3C_{1-8}$-alkyl is optionally substituted with one or more substituents selected from the group consisting of halogen, —$OR^a$, and —$NR^bR^c$; wherein $R^4$ is hydrogen or $C_{1-8}$-alkyl, wherein the $C_{1-8}$-alkyl is optionally substituted with one or more substituents selected from the group consisting of halogen, and —$OR^a$, and wherein $R^e$, $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is $NR^3R^4$, wherein $R^3$ is $C_{1-8}$-alkyl, wherein the $R^3C_{1-8}$-alkyl is optionally substituted with one or more substituents selected from the group consisting of halogen, —$OR^a$, and —$NR^bR^c$; wherein $R^4$ is hydrogen or $C_{1-8}$-alkyl, wherein the $C_{1-8}$-alkyl is optionally substituted with one or more substituents selected from the group consisting of halogen, and —$OR^a$, and wherein $R^e$, $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is $NR^3R^4$, wherein $R^3$ is heteroaryl-($C_{1-8}$-alkyl), wherein the aryl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is heteroaryl-($C_{1-8}$-alkyl), wherein the aryl is optionally substituted with one or two substituents independently selected from the group consisting of $C_{1-8}$-alkyl, heterocyclyl, halogen, —$OR^d$, $C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is $C_{1-8}$-alkyl, wherein the $R^3C_{1-8}$-alkyl is optionally substituted with one or more substituents selected from the group consisting of halogen, —$OR^a$, and —$NR^bR^c$; wherein $R^4$ is hydrogen or $C_{1-8}$-alkyl, wherein the $C_{1-8}$-alkyl is optionally substituted with one or more substituents selected from the group consisting of halogen, and —$OR^a$, wherein $R^e$, $R^d$, $R^e$, and $R^f$ are independently selected from the group consisting of hydrogen, $C_{1-8}$-alkyl, and $C_{3-8}$-cycloalkyl, wherein the $C_{1-8}$-alkyl is optionally substituted with —$NH_2$, or —$O(C_{1-8}$-alkyl)$NH_2$.

In another embodiment, the present invention provides compounds of formula (I) wherein $R^{1a}$, $R^{1b}$, and $R^{1c}$ are hydrogen, X is N, Y is $NR^3R^4$, wherein $R^3$ is $C_{1-8}$-alkyl, wherein the $R^3C_{1-8}$-alkyl is optionally substituted with one or more substituents selected from the group consisting of halogen, —$OR^a$, and —$NR^bR^c$; wherein $R^4$ is hydrogen or $C_{1-8}$-alkyl, wherein the $C_{1-8}$-alkyl is optionally substituted with one or more substituents selected from the group consisting of halogen, and —$OR^a$, wherein $R^e$, $R^d$, $R^e$, and $R^f$ are independently selected from the group consisting of hydrogen, $C_{1-8}$-alkyl, and $C_{3-8}$-cycloalkyl, wherein the $C_{1-8}$-alkyl is optionally substituted with —$NH_2$, or —$O(C_{1-8}$-alkyl)$NH_2$.

In another embodiment, the present invention provides compounds of formula (I) wherein $R^{1a}$, $R^{1b}$, and $R^{1c}$ are hydrogen, X is $CR^2$, $R^2$ is hydrogen, Y is aryl, wherein the aryl is optionally substituted with one or more substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is aryl, wherein the aryl is optionally substituted with one or more substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is $CR^2$, $R^2$ is hydrogen, Y is heteroaryl, wherein the heteroaryl is optionally substituted with one or more substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is heteroaryl, wherein the heteroaryl is optionally substituted with one or more substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

In another embodiment, the present invention provides compounds of formula (I) wherein $R^{1a}$, $R^{1b}$, and $R^{1c}$ are hydrogen, X is N, Y is $NR^3R^4$, wherein $R^3$ is $C_{3-8}$-cycloalkyl, wherein the $C_{3-8}$-cycloalkyl is optionally substituted with one or two substituents independently selected from the group consisting of C$_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$ wherein the C$_{1-8}$-alkyl is optionally substituted with one or more —OR$^d$, and wherein R$^d$, R$^e$, and R$^f$ are independently selected from the group consisting of hydrogen, C$_{1-8}$-alkyl, C$_{3-8}$-cycloalkyl, and heterocyclyl wherein the heterocyclyl is optionally substituted with one or more aryl-(C$_{1-8}$-alkyl), wherein the aryl-(C$_{1-8}$-alkyl), is optionally substituted with one or more halogen.

In another embodiment, the present invention provides compounds of formula (I) wherein R$^{1a}$, R$^{1b}$, and R$^{1c}$ are hydrogen, X is CR$^2$, R$^2$ is hydrogen, Y is NR$^3$R$^4$, wherein R$^3$ is C$_{3-8}$-cycloalkyl, wherein the C$_{3-8}$-cycloalkyl is optionally substituted with one or two substituents independently selected from the group consisting of C$_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$ wherein the C$_{1-8}$-alkyl is optionally substituted with one or more —OR$^d$, wherein R$^4$ is hydrogen or C$_{1-8}$-alkyl, and wherein R$^d$, R$^e$, and R$^f$ are independently selected from the group consisting of hydrogen, C$_{1-8}$-alkyl, and C$_{3-8}$-cycloalkyl, and heterocyclyl wherein the heterocyclyl is optionally substituted with one or more aryl-(C$_{1-8}$-alkyl), wherein the aryl-(C$_{1-8}$-alkyl)-, is optionally substituted with one or more halogen.

Another aspect of the invention provides compounds of formula (II), wherein R$^{1a}$, R$^{1b}$,

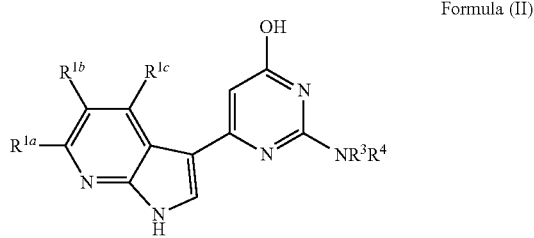

Formula (II)

In one aspect, the present invention provides compounds of formula (II), wherein R$^{1a}$, R$^{1b}$ and R$^{1c}$ are independently hydrogen, hydroxy, nitro, halogen, cyano, trifluoromethyl, trifluoromethoxy, C$_{1-4}$-alkyl, —OR$^a$, —NR$^b$R$^c$; —C(O)OR$^a$, —C(O)NR$^b$R$^c$, —NR$^b$C(O)R$^c$, —NHC(O)NHR$^b$, or —NHSO$_2$R$^a$;

R$^3$ is hydrogen, C$_{1-8}$-alkyl, C$_{2-8}$-alkenyl, C$_{2-8}$-alkynyl, C$_{3-8}$-cycloalkyl, C$_{3-8}$-cycloalkyl-(C$_{1-8}$-alkyl)-, heterocycloalkyl, heterocycloalkyl-(C$_{1-8}$-alkyl)-, aryl, aryl-(C$_{1-8}$-alkyl)-, heteroaryl-, or heteroaryl-(C$_{1-8}$-alkyl), wherein (a) the R$^3$C$_{1-8}$-alkyl, C$_{2-8}$-alkenyl, C$_{2-8}$-alkynyl substituents, alone or as part of another group, are optionally substituted with one or more substituents selected from the group consisting of halogen, cyano, nitro, —OR$^a$, —C(O)R$^a$, —C(O)OR$^a$, —OC(O)R$^a$, —NR$^b$R$^c$, —NR$^b$C(O)R$^a$, —NHC(O)NHR$^b$, —C(O)NR$^b$R$^c$, —NHSO$_2$R$^a$, —SO$_2$NR$^b$NR$^c$, and aryl; and (b) the R$^3$C$_{3-8}$-cycloalkyl, heterocycloalkyl, aryl, and heteroaryl, alone or as part of another group, are optionally substituted with one or more R$^5$;

R$^4$ is hydrogen or C$_{1-8}$-alkyl; wherein the C$_{1-8}$-alkyl is optionally substituted with one or more substituents selected from the group consisting of halogen, cyano, —OR$^a$, —C(O)Ra, —C(O)OR$^a$, —OC(O)R$^a$, —NR$^b$R$^c$, —NR$^b$C(O)R$^a$, —NHC(O)NHR$^b$, —C(O)NR$^b$R$^c$, —NHSO$_2$R$^a$, and —SO$_2$NR$^b$NR$^c$;

R$^5$ is selected from the group consisting of C$_{1-8}$-alkyl, C$_{2-8}$-alkenyl, C$_{2-8}$-alkynyl, aryl, heterocyclyl, halogen, cyano, nitro, —OR$^d$, —C(O)R$^d$, —C(O)OR$^d$, —OC(O)R$^d$, —NR$^e$R$^f$, —NR$^e$C(O)R$^d$, —NHC(O)NHR$^e$, —NHSO$_2$R$^e$, —C(O)NR$^e$R$^f$, —SR$^d$, —S(O)R$^d$, —SO$_2$R$^d$, —SO$_2$NR$^e$NR$^f$, —B(OH)$_2$, —CF$_3$, —CF$_2$CF$_3$, —OCF$_3$, and —OCF$_2$CF$_3$ wherein (a) the R$^5$C$_{1-8}$-alkyl, C$_{2-8}$-alkenyl, C$_{2-8}$-alkynyl, substituents are optionally substituted with one or more substituents selected from the group consisting of aryl, heterocyclyl, C$_{3-8}$-cycloalkyl, halogen, cyano, nitro, —OR$^d$, —C(O)R$^d$, —C(O)OR$^d$, —OC(O)R$^d$, —NR$^e$R$^f$, —NR$^e$C(O)R$^d$, —NHC(O)NHR$^e$, —C(O)NR$^e$R$^f$; and wherein (b) the R$^5$ aryl or heterocyclyl substituents are optionally substituted with one or more substituents independently selected from the group consisting of C$_{1-8}$-alkyl, C$_{2-8}$-alkenyl, C$_{2-8}$-alkynyl, aryl, heterocyclyl, halogen, cyano, nitro, —OR$^g$, —C(O)R$^g$, —C(O)OR$^g$, —OC(O)R$^g$, —NR$^h$R$^i$, —NR$^h$C(O)R$^g$, —NHC(O)NHR$^h$, —NHSO$_2$R$^g$, —C(O)NR$^h$R$^i$, —SR$^g$, —S(O)R$^g$, —SO$_2$R$^g$, —SO$_2$NR$^h$NR$^i$, —CF$_3$, —CF$_2$CF$_3$, —OCF$_3$, and —OCF$_2$CF$_3$;

R$^a$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, heterocyclyl, C$_{3-8}$-cycloalkyl, halogen, cyano, hydroxy, C$_{1-8}$-alkoxy, —NH$_2$, —NH(C$_{1-8}$-alkyl), —O(C$_{1-8}$-alkyl)NH$_2$, and —N(C$_{1-8}$-alkyl)$_2$;

R$^b$ and R$^c$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^b$ and R$^c$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^d$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, aryl-(C$_{1-8}$-alkyl)-, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$; wherein the aryl, aryl-(C$_{1-8}$-alkyl), heterocyclyl, and C$_{3-8}$-cycloalkyl, alone or as part of another group, are optionally substituted with one or more substituents independently selected from the group consisting of C$_{1-8}$-alkyl, aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^e$ and R$^f$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^e$ and R$^f$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^g$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^i$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

or a pharmaceutically acceptable salt thereof.

In one embodiment of formula (II), $R^{1a}$, $R^{1b}$, and $R^{1c}$ are hydrogen. In another embodiment of formula (II), $R^{1b}$ and $R^{1c}$ are hydrogen and $R^{1a}$ is hydroxy, nitro, halogen, cyano, trifluoromethyl, trifluoromethoxy, $C_{1-4}$-alkyl, —$OR^a$, —$NR^b R^c$, —$C(O)OR^a$, —$C(O)NR^b R^c$, —$NR^b C(O)R^c$, —$NHC(O)NHR^b$, or —$NHSO_2R^a$. In another embodiment of formula (II), $R^{1a}$ and $R^{1c}$ are hydrogen and $R^{1b}$ is hydroxy, nitro, halogen, cyano, trifluoromethyl, trifluoromethoxy, $C_{1-4}$-alkyl, —$OR^a$, —$NR^b R^c$, —$C(O)OR^a$, —$C(O)NR^b R^c$, —$NR^b C(O)R^c$, —$NHC(O)NHR^b$, or —$NHSO_2R^a$. In another embodiment of formula (II), $R^{1c}$ is hydrogen and $R^{1a}$ and $R^{1b}$ are each independently hydroxy, nitro, halogen, cyano, trifluoromethyl, trifluoromethoxy, $C_{1-4}$-alkyl, —$OR^a$, —$NR^b R^c$, —$C(O)OR^a$, —$C(O)NR^b R^c$, —$NR^b C(O)R^c$, —$NHC(O)NHR^b$, or —$NHSO_2R^a$.

In one embodiment of formula (II), $R^3$ is $C_{1-8}$-alkyl. In another embodiment of formula (II), $R^3$ is $C_{1-8}$-alkyl which is unsubstituted. In another embodiment of formula (II), $R^3$ is $C_{1-8}$-alkyl which is substituted with one or more substituents selected from the group consisting of halogen, cyano, nitro, —$OR^a$, —$C(O)R^a$, —$C(O)OR^a$, —$OC(O)Ra$, —$NR^b R^c$, —$NR^b C(O)R^a$, —$NHC(O)NHR^b$, —$C(O)NR^b R^c$, —$NHSO_2R^a$, and —$SO_2NR^b NR^c$. In another embodiment of formula (II), $R^3$ is $C_{1-8}$-alkyl which is substituted with one or two substituents selected from the group consisting of —$OR^a$, and —$NR^b R^c$. In another embodiment of formula (II), $R^3$ is $C_{1-8}$-alkyl which is substituted with one or two substituents selected from the group consisting of —$OR^a$, and —$NR^b R^c$ wherein $R^a$, $R^b$, and $R^c$ are independently selected from the group consisting of hydrogen and $C_{1-8}$-alkyl. In another embodiment of formula (II), $R^3$ is $C_{1-8}$-alkyl which is substituted with one or two substituents selected from the group consisting of —OH, $OCH_3$, —$OCH_2CH_2OCH_2CH_2NH_2$, and —$NHCH_3$.

In another embodiment of formula (II), $R^3$ is aryl or heteroaryl, which is optionally substituted with one or more $R^5$. In another embodiment of formula (II), the aryl or heteroaryl is unsubstituted.

In one embodiment of formula (II), $R^3$ is phenyl, which is substituted with one, two or three $R^5$, and $R^5$ is selected from the group consisting of $C_{1-8}$-alkyl, heterocyclyl, halogen, —$OR^d$, —$C(O)OR^d$, —$NR^e R^f$, —$NR^e C(O)R^d$, —$NHSO_2R^e$, —$SO_2R^d$, —$CF_3$, and —$OCF_3$, wherein (a) the $R^5C_{1-8}$-alkyl substituent is optionally substituted with —$OR^d$. In one embodiment of formula (II), $R^3$ is phenyl, which is substituted with one, two, or three $R^5$, and $R^5$ is $OR^d$, wherein $R^d$ is $C_{1-8}$-alkyl.

In another embodiment of formula (II), $R^3$ is a 5-7-membered heteroaryl optionally substituted with one or more $R^5$. In another embodiment of formula (I), $R^3$ is 5-7 membered heteroaryl which is unsubstituted. In yet another embodiment of formula (I), $R^3$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, which is unsubstituted. In one embodiment of formula (I), $R^3$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, which is substituted with one, two or three $R^5$, and $R^5$ is selected from the group consisting of $C_{1-8}$-alkyl, heterocyclyl, halogen, —$OR^d$, —$C(O)OR^d$, —$NR^e R^f$, —$NR^e C(O)R^d$, —$NHSO_2R^e$, —$SO_2R^d$, —$CF_3$, and —$OCF_3$.

In another embodiment of formula (II), $R^3$ is heterocycloalkyl, which is optionally substituted with one or more $R^5$. In another embodiment of formula (II), $R^3$ is heterocycloalkyl, which unsubstituted. In one embodiment of formula (II), $R^3$ is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, which is unsubstituted. In one embodiment of formula (II), $R^7$ is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, which is substituted with one, two, or three $R^5$, and $R^5$ is selected from the group consisting of $C_{1-8}$-alkyl, heterocyclyl, halogen, —$OR^d$, —$C(O)OR^d$, —$NR^e R^f$, —$NR^e C(O)R^d$, —$NHSO_2R^e$, —$SO_2R^d$, —$CF_3$, and —$OCF_3$, wherein (a) the $R^5C_{1-8}$-alkyl substituent is optionally substituted with —$OR^d$. In one embodiment of formula (II), $R^3$ is pyrrolidinyl, tetrahydrofuryl, piperidinyl, or tetrahydropyranyl.

In another embodiment of formula (II), $R^3$ is cycloalkyl, which is optionally substituted with one or more $R^5$. In another embodiment of formula (II), $R^3$ is cycloalkyl, which unsubstituted. In one embodiment of formula (II), $R^3$ is cyclopentyl, cyclohexyl, and cycloheptyl, which is unsubstituted. In one embodiment of formula (II), $R^3$ is cyclopentyl, cyclohexyl, and cycloheptyl, which is substituted with one, two, or three $R^5$, and $R^5$ is selected from the group consisting of $C_{1-8}$-alkyl, heterocyclyl, halogen, —$OR^d$, —$C(O)OR^d$, —$NR^e R^f$, —$NR^e C(O)R^d$, —$NHSO_2R^e$, —$SO_2R^d$, —$CF_3$, and —$OCF_3$, wherein (a) the $R^5C_{1-8}$-alkyl substituent is optionally substituted with —$OR^d$. In one embodiment of formula (II), $R^3$ is cyclopentyl, cyclohexyl, and cycloheptyl, which is substituted with one, two, or three $R^5$, and $R^5$ is —$OR^d$, —$NR^e R^f$, —$NR^e C(O)R^d$, or —$NHSO_2R^e$, wherein $R^d$, at each occurrence, is selected from the group consisting of hydrogen, $C_{1-8}$-alkyl, heterocyclyl, and $C_{3-8}$-cycloalkyl, wherein the heterocyclyl is optionally substituted with one or more substituents independently selected from the group consisting of aryl-($C_{1-8}$-alkyl), wherein the aryl-($C_{1-8}$-alkyl), alone or as part of another group, is optionally substituted with one or more substituents independently selected from the group consisting of halogen, and $R^e$ and $R^f$, at each occurrence, are independently selected from the group consisting of hydrogen, and $C_{3-8}$-cycloalkyl.

In one embodiment of formula (II), $R^3$ is $C_{3-8}$-cycloalkyl ($C_{1-8}$-alkyl), heterocycloalkyl($C_{1-8}$-alkyl), aryl-($C_{1-8}$-alkyl), or heteroaryl($C_{1-8}$-alkyl), and the $R^3$—($C_{1-8}$-alkyl)- is unsubstituted. In another embodiment of formula (II), where $R^3$ is $C_{3-8}$-cycloalkyl($C_{1-8}$-alkyl), heterocycloalkyl($C_{1-8}$-alkyl), aryl-($C_{1-8}$-alkyl), or heteroaryl-($C_{1-8}$-alkyl), the $R^3$ ($C_{1-8}$-alkyl)- is optionally substituted with one or two substituents selected from the group consisting of —$OR^a$ and —$NR^b R^c$.

In one embodiment of formula (II), $R^3$ is $C_{3-8}$-cycloalkyl $(C_{1-8}$-alkyl), heterocycloalkyl($C_{1-8}$-alkyl), aryl-($C_{1-8}$-alkyl), or heteroaryl($C_{1-8}$-alkyl), the —($C_{1-8}$-alkyl)- is ($C_1$-alkyl)-, —($C_2$-alkyl)-, or —($C_3$-alkyl)-. In one embodiment of formula (I), $R^3$ is —($C_1$-alkyl)-.

In another embodiment of formula (II), $R^3$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), wherein the $R^3C_{3-8}$-cycloalkyl, heterocycloalkyl, aryl, and heteroaryl are optionally substituted. In another embodiment of formula (I), $R^3$ is $C_{3-8}$-cycloalkyl($C_{1-8}$-alkyl), heterocycloalkyl ($C_{1-8}$-alkyl), aryl-($C_{1-8}$-alkyl), or heteroaryl($C_{1-8}$-alkyl), wherein the $R^3C_{3-8}$-cycloalkyl, heterocycloalkyl, aryl, and heteroaryl are unsubstituted. In another embodiment of formula (I), $R^3$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), wherein the $R^3C_{3-8}$-cycloalkyl, heterocycloalkyl, aryl, and heteroaryl are substituted with one or more $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, or —$OCF_3$, wherein (a) the $R^5C_{1-8}$-alkyl substituent is optionally substituted with one or more —$OR^d$. In another embodiment of formula (II), $R^3$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), wherein the $R^3C_{3-8}$-cycloalkyl, heterocycloalkyl, aryl, and heteroaryl are substituted with one, two, or three $R^5$, and $R^5$ is selected from the group consisting of halogen, —OH, and —$CF_3$.

In one embodiment of formula (II), $R^3$ is $C_{3-8}$-cycloalkyl $(C_{1-8}$-alkyl), the $C_{3-8}$-cycloalkyl is an optionally substituted cyclobutyl, cyclopentyl, or cyclohexyl.

In one embodiment of formula (II), where $R^3$ is heterocycloalkyl($C_{1-8}$-alkyl), the heterocycloalkyl is an optionally substituted 5-7 membered heterocycloalkyl. In another embodiment of formula (II), the $R^3$ heterocyclcoalkyl is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In another embodiment of formula (II), wherein $R^3$ is heterocycloalkyl($C_{1-8}$-alkyl), the heterocycloalkyl is an optionally substituted morpholinyl or tetrahydropyranyl.

In one embodiment, wherein $R^3$ is aryl($C_{1-8}$-alkyl), the aryl is an optionally substituted phenyl.

In one embodiment, wherein $R^3$ is heteroaryl($C_{1-8}$-alkyl), the heteroaryl is an optionally substituted 5-7-membered heteroaryl. In yet another embodiment, where $R^3$ is heteroaryl-($C_{1-8}$-alkyl), the $R^3$ heteroaryl is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl. In yet another embodiment, where $R^3$ is heteroaryl($C_{1-8}$-alkyl), the $R^3$ heteroaryl is imidazolyl.

In one embodiment of formula (II), $R^4$ is hydrogen. In another embodiment of formula (II), $R^4$ is an unsubstituted branched or straight chain $C_{1-8}$ alkyl. In yet another embodiment of formula (II), $R^4$ is methyl, ethyl, propyl, isopropyl, n-butyl, sec-butyl, or t-butyl. In another embodiment of formula (II), $R^4$ is methyl. In another embodiment of formula (II), $R^4$ is a substituted branched or straight chain $C_{1-8}$ alkyl, wherein the $C_{1-8}$-alkyl is substituted with —$OR^a$ wherein $R^a$ is selected from the group consisting of H and $C_{1-8}$-alkyl. In another embodiment of formula (II), $R^4$ is a substituted branched or straight chain $C_{1-8}$ alkyl, wherein the $C_{1-8}$-alkyl is substituted with —$OCH_3$.

In another embodiment of formula (II), $NR^3R^4$ is selected from the group consisting of

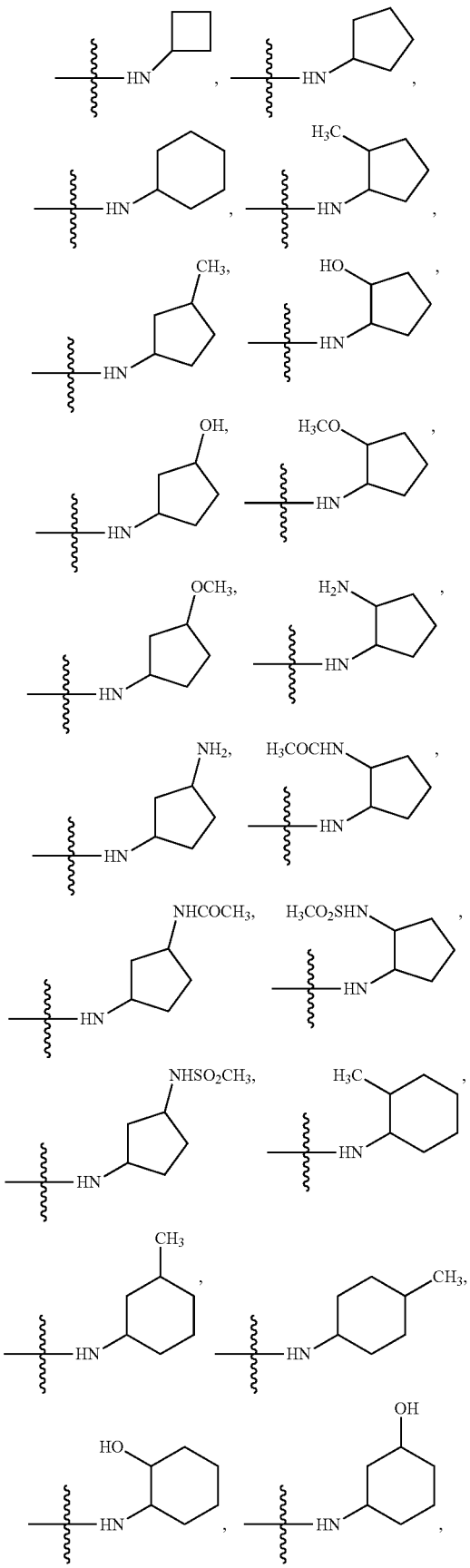

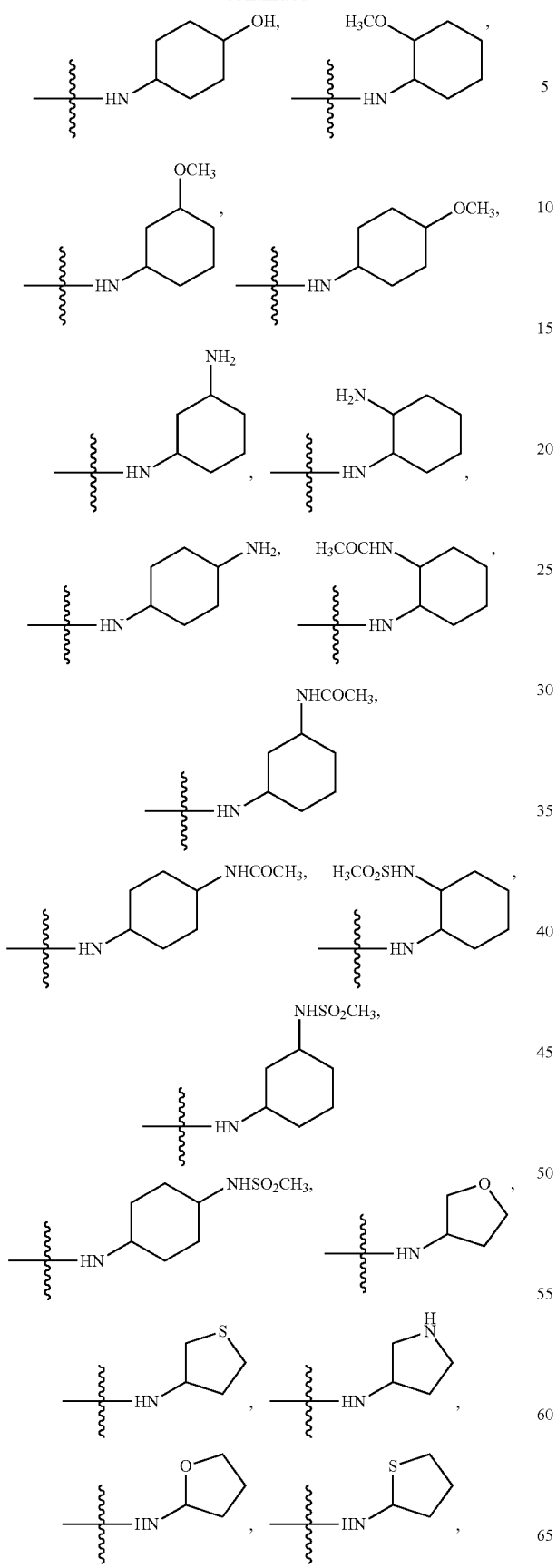
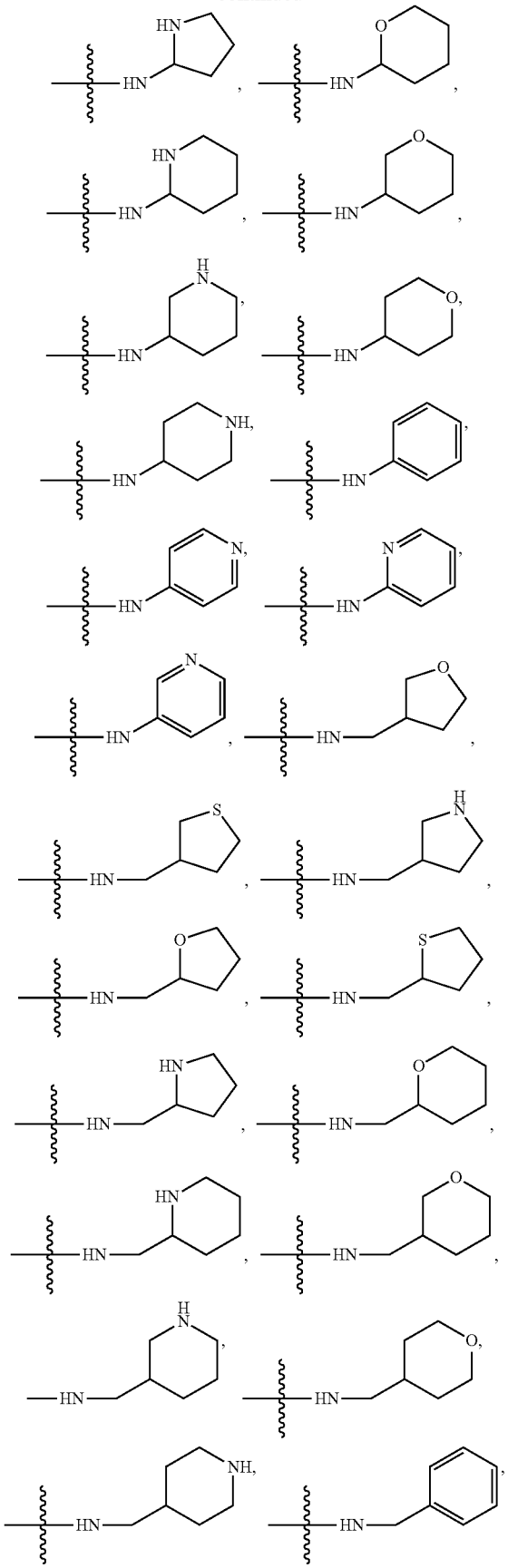

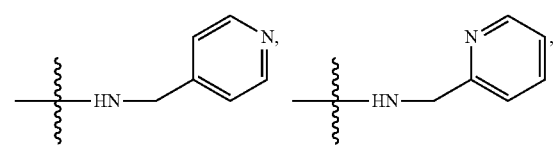
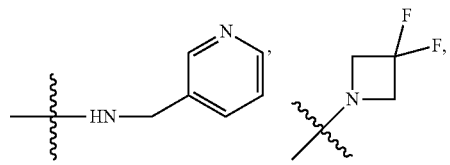
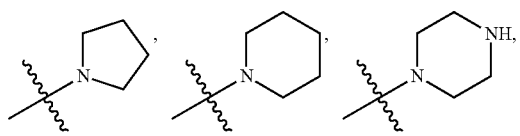
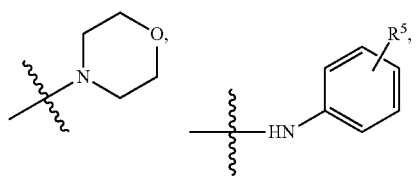
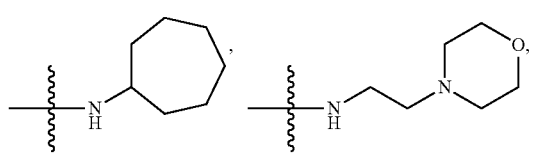
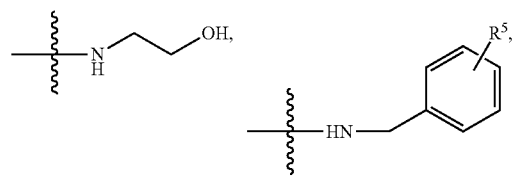
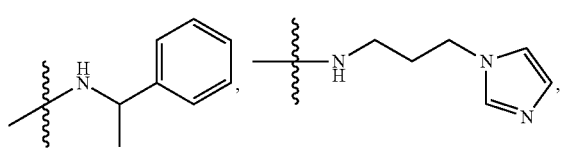
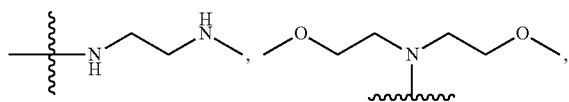
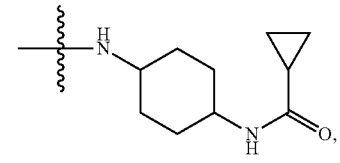
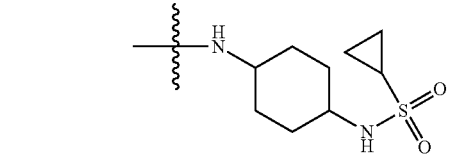
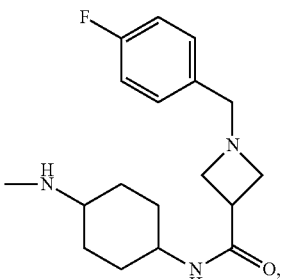
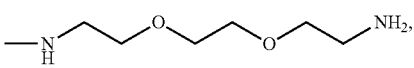
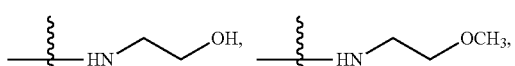
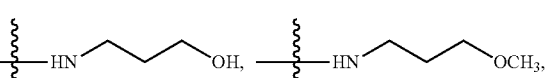
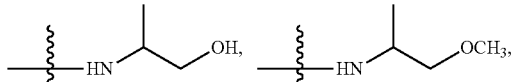
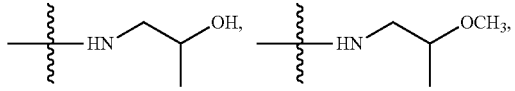
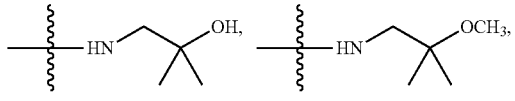
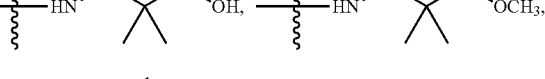
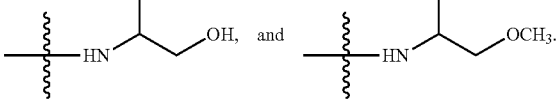
Another aspect of the invention provides compounds of formula (III), wherein $R^{1a}$, $R^{1b}$, $R^{1c}$, $R^3$ and $R^4$ are as defined generally and in subsets above.

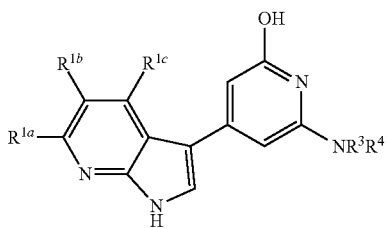

Formula (III)

In one aspect, the present invention provides compounds of formula (III), wherein $R^{1a}$, $R^{1b}$ and $R^{1c}$ are independently hydrogen, hydroxy, nitro, halogen, cyano, trifluoromethyl, trifluoromethoxy, $C_{1-4}$-alkyl, —$OR^a$, —$NR^bR^c$; —$C(O)OR^a$, —$C(O)NR^bR^c$, —$NR^bC(O)R^c$, —$NHC(O)NHR^b$, or —$NHSO_2R^a$;

$R^3$ is hydrogen, $C_{1-8}$-alkyl, $C_{2-8}$-alkenyl, $C_{2-8}$-alkynyl, $C_{3-8}$-cycloalkyl, $C_{3-8}$-cycloalkyl-($C_{1-8}$-alkyl)-, heterocycloalkyl, heterocycloalkyl-($C_{1-8}$-alkyl)-, aryl, aryl-($C_{1-8}$-alkyl)-, heteroaryl-, or heteroaryl-($C_{1-8}$-alkyl), wherein (a) the $R^3C_{1-8}$-alkyl, $C_{2-8}$-alkenyl, $C_{2-8}$-alkynyl substituents, alone or as part of another group, are optionally substituted with one or more substituents selected from the group consisting of halogen, cyano, nitro, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, —$SO_2NR^bNR^c$, and aryl; and (b) the $R^3C_{3-8}$-cycloalkyl, heterocycloalkyl, aryl, and heteroaryl, alone or as part of another group, are optionally substituted with one or more $R^5$;

$R^4$ is hydrogen or $C_{1-8}$-alkyl; wherein the $C_{1-8}$-alkyl is optionally substituted with one or more substituents selected from the group consisting of halogen, cyano, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$;

$R^5$ is selected from the group consisting of $C_{1-8}$-alkyl, $C_{2-8}$-alkenyl, $C_{2-8}$-alkynyl, aryl, heterocyclyl, halogen, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$NHSO_2R^e$, —$C(O)NR^eR^f$, —$SR^d$, —$S(O)R^d$, —$SO_2R^d$, —$SO_2NR^eNR^f$, —$B(OH)_2$, —$CF_3$, —$CF_2CF_3$, —$OCF_3$, and —$OCF_2CF_3$ wherein (a) the $R^5C_{1-8}$-alkyl, $C_{2-8}$-alkenyl, $C_{2-8}$-alkynyl, substituents are optionally substituted with one or more substituents selected from the group consisting of aryl, heterocyclyl, $C_{3-8}$-cycloalkyl, halogen, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$C(O)NR^eR^f$; and wherein (b) the $R^5$ aryl or heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, —$OR^g$, —$C(O)R^g$, —$C(O)OR^g$, —$OC(O)R^g$, —$NR^hR^i$, —$NR^hC(O)R^g$, —$NHC(O)NHR^h$, —$NHSO_2R^g$, —$C(O)NR^hR^i$, —$SR^g$, —$S(O)R^g$, —$SO_2R^g$, —$SO_2NR^hNR^i$, —$CF_3$, —$CF_2CF_3$, —$OCF_3$, and —$OCF_2CF_3$;

$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), —$O(C_{1-8}$-alkyl)$NH_2$, and —$N(C_{1-8}$-alkyl)$_2$;

$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^e$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, aryl-($C_{1-8}$-alkyl)-, heterocyclyl, $C_{3-8}$-cycloalkyl, halogen, cyano, hydroxy, $C_{1-8}$-alkoxy, —$NH_2$; —$NH(C_{1-8}$-alkyl), and —$N(C_{1-8}$-alkyl)$_2$; wherein the aryl, aryl-($C_{1-8}$-alkyl)-, heterocyclyl, and $C_{3-8}$-cycloalkyl, alone or as part of another group, are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^e$ and $R^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^e$ and $R^f$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^g$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^i$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

or a pharmaceutically acceptable salt thereof.

In one embodiment of formula (III), $R^{1a}$, $R^{1b}$, and $R^{1c}$ are hydrogen. In another embodiment of formula (III), $R^{1b}$ and $R^{1c}$ are hydrogen and $R^{1a}$ is hydroxy, nitro, halogen, cyano, trifluoromethyl, trifluoromethoxy, $C_{1-4}$-alkyl, —$OR^a$, —$NR^bR^c$, —$C(O)OR^a$, —$C(O)NR^bR^c$, —$NR^bC(O)R^c$, —$NHC(O)NHR^b$, or —$NHSO_2R^a$. In another embodiment of formula (III), $R^{1a}$ and $R^{1c}$ are hydrogen and $R^{1b}$ is hydroxy, nitro, halogen, cyano, trifluoromethyl, trifluoromethoxy, $C_{1-4}$-alkyl, —$OR^a$, —$NR^bR^c$, —$C(O)OR^a$, —$C(O)NR^bR^c$, —NR$^b$C(O)R$^c$, —NHC(O)NHR$^b$, or —NHSO$_2$R$^a$. In another embodiment of formula (III), R$^{1c}$ is hydrogen and R$^{1a}$ and R$^{1b}$ are each independently hydroxy, nitro, halogen, cyano, trifluoromethyl, trifluoromethoxy, C$_{1-4}$-alkyl, —OR$^a$, —NR$^b$R$^c$, —C(O)OR$^a$, —C(O)NR$^b$R$^c$, —NR$^b$C(O)R$^c$, —NHC(O)NHR$^b$, or —NHSO$_2$R$^a$.

In one embodiment of formula (III), R$^3$ is C$_{1-8}$-alkyl. In another embodiment of formula (III), R$^3$ is C$_{1-8}$-alkyl which is unsubstituted. In another embodiment of formula (III), R$^3$ is C$_{1-8}$-alkyl which is substituted with one or more substituents selected from the group consisting of halogen, cyano, nitro, —OR$^a$, —C(O)R$^a$, —C(O)OR$^a$, —OC(O)R$^a$, —NR$^b$R$^c$, NR$^b$C(O)R$^a$, —NHC(O)NHR$^b$, —C(O)NR$^b$R$^c$, —NHSO$_2$R$^a$, and —SO$_2$NR$^b$NR$^c$. In another embodiment of formula (I), R$^3$ is C$_{1-8}$-alkyl which is substituted with one or two substituents selected from the group consisting of —OR$^a$, and —NR$^b$R$^c$. In another embodiment of formula (III), R$^3$ is C$_{1-8}$-alkyl which is substituted with one or two substituents selected from the group consisting of —OR$^a$, and —NR$^b$R$^c$ wherein R$^a$, R$^b$, and R$^c$ are independently selected from the group consisting of hydrogen and C$_{1-8}$-alkyl. In another embodiment of formula (III), R$^3$ is C$_{1-8}$-alkyl which is substituted with one or two substituents selected from the group consisting of —OH, OCH$_3$, —OCH$_2$CH$_2$OCH$_2$CH$_2$NH$_2$, and —NHCH$_3$.

In another embodiment of formula (III), R$^3$ is aryl or heteroaryl, which is optionally substituted with one or more R$^5$. In another embodiment of formula (III), the aryl or heteroaryl is unsubstituted.

In one embodiment of formula (III), R$^3$ is phenyl, which is substituted with one, two or three R$^5$, and R$^5$ is selected from the group consisting of C$_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$, wherein (a) the R$^5$C$_{1-8}$-alkyl substituent is optionally substituted with —OR$^d$. In one embodiment of formula (III), R$^3$ is phenyl, which is substituted with one, two, or three R$^5$, and R$^5$ is OR$^d$, wherein R$^d$ is C$_{1-8}$-alkyl.

In another embodiment of formula (III), R$^3$ is a 5-7-membered heteroaryl optionally substituted with one or more R$^5$. In another embodiment of formula (III), R$^3$ is 5-7 membered heteroaryl which is unsubstituted. In yet another embodiment of formula (III), R$^3$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, which is unsubstituted. In one embodiment of formula (III), R$^3$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, which is substituted with one, two or three R$^5$, and R$^5$ is selected from the group consisting of C$_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$.

In another embodiment of formula (III), R$^3$ is heterocycloalkyl, which is optionally substituted with one or more R$^5$. In another embodiment of formula (III), R$^3$ is heterocycloalkyl, which unsubstituted. In one embodiment of formula (III), R$^3$ is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, which is unsubstituted. In one embodiment of formula (III), R$^7$ is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, which is substituted with one, two, or three R$^5$, and R$^5$ is selected from the group consisting of C$_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$, wherein (a) the R$^5$C$_{1-8}$-alkyl substituent is optionally substituted with —OR$^d$. In one embodiment of formula (III), R$^3$ is pyrrolidinyl, tetrahydrofuryl, piperidinyl, or tetrahydropyranyl.

In another embodiment of formula (III), R$^3$ is cycloalkyl, which is optionally substituted with one or more R$^5$. In another embodiment of formula (III), R$^3$ is cycloalkyl, which unsubstituted. In one embodiment of formula (III), R$^3$ is cyclopentyl, cyclohexyl, and cycloheptyl, which is unsubstituted. In one embodiment of formula (III), R$^3$ is cyclopentyl, cyclohexyl, and cycloheptyl, which is substituted with one, two, or three R$^5$, and R$^5$ is selected from the group consisting of C$_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, and —OCF$_3$, wherein (a) the R$^5$C$_{1-8}$-alkyl substituent is optionally substituted with —OR$^d$. In one embodiment of formula (III), R$^3$ is cyclopentyl, cyclohexyl, and cycloheptyl, which is substituted with one, two, or three R$^5$, and R$^5$ is —OR$^d$, —NR$^e$R$^f$, —NR$^e$C(O)R$^d$, or —NHSO$_2$R$^e$, wherein R$^d$, at each occurrence, is selected from the group consisting of hydrogen, C$_{1-8}$-alkyl, heterocyclyl, and C$_{3-8}$-cycloalkyl, wherein the heterocyclyl is optionally substituted with one or more substituents independently selected from the group consisting of aryl-(C$_{1-8}$-alkyl)-, wherein the aryl-(C$_{1-8}$-alkyl), alone or as part of another group, is optionally substituted with one or more substituents independently selected from the group consisting of halogen, and R$^e$ and R$^f$, at each occurrence, are independently selected from the group consisting of hydrogen, and C$_{3-8}$-cycloalkyl.

In one embodiment of formula (III), R$^3$ is C$_{3-8}$-cycloalkyl (C$_{1-8}$-alkyl), heterocycloalkyl(C$_{1-8}$-alkyl), aryl-(C$_{1-8}$-alkyl), or heteroaryl(C$_{1-8}$-alkyl), and the R$^3$ (C$_{1-8}$-alkyl)- is unsubstituted. In another embodiment of formula (III), where R$^3$ is C$_{3-8}$-cycloalkyl(C$_{1-8}$-alkyl), heterocycloalkyl(C$_{1-8}$-alkyl), aryl-(C$_{1-8}$-alkyl), or heteroaryl-(C$_{1-8}$-alkyl), the R$^3$ (C$_{1-8}$-alkyl)- is optionally substituted with one or two substituents selected from the group consisting of —OR$^a$ and —NR$^b$R$^c$.

In one embodiment of formula (III), R$^3$ is C$_{3-8}$-cycloalkyl (C$_{1-8}$-alkyl), heterocycloalkyl(C$_{1-8}$-alkyl), aryl-(C$_{1-8}$-alkyl), or heteroaryl(C$_{1-8}$-alkyl), the —(C$_{1-8}$-alkyl)- is (C$_1$-alkyl)-, —(C$_2$-alkyl)-, or (C$_3$-alkyl)-. In one embodiment of formula (III), R$^3$ is (C$_1$-alkyl)-.

In another embodiment of formula (III), R$^3$ is C$_{3-8}$-cycloalkyl(C$_{1-8}$-alkyl), heterocycloalkyl(C$_{1-8}$-alkyl), aryl-(C$_{1-8}$-alkyl), or heteroaryl(C$_{1-8}$-alkyl), wherein the R$^3$C$_{3-8}$-cycloalkyl, heterocycloalkyl, aryl, and heteroaryl are optionally substituted. In another embodiment of formula (III), R$^3$ is C$_{3-8}$-cycloalkyl(C$_{1-8}$-alkyl), heterocycloalkyl-(C$_{1-8}$-alkyl)-, aryl-(C$_{1-8}$-alkyl), or heteroaryl(C$_{1-8}$-alkyl), wherein the R$^3$C$_{3-8}$-cycloalkyl, heterocycloalkyl, aryl, and heteroaryl are unsubstituted. In another embodiment of formula (III), R$^3$ is C$_{3-8}$-cycloalkyl(C$_{1-8}$-alkyl), heterocycloalkyl(C$_{1-8}$-alkyl), aryl-(C$_{1-8}$-alkyl), or heteroaryl(C$_{1-8}$-alkyl), wherein the R$^3$C$_{3-8}$-cycloalkyl, heterocycloalkyl, aryl, and heteroaryl are substituted with one or more C$_{1-8}$-alkyl, heterocyclyl, halogen, —OR$^d$, —C(O)OR$^d$, —NR$^e$R$^f$, —NR$^e$C(O)R$^d$, —NHSO$_2$R$^e$, —SO$_2$R$^d$, —CF$_3$, or —OCF$_3$, wherein (a) the R$^5$C$_{1-8}$-alkyl substituent is optionally substituted with one or more —OR$^d$. In another embodiment of formula (III), R$^3$ is C$_{3-8}$-cycloalkyl(C$_{1-8}$-alkyl), heterocycloalkyl(C$_{1-8}$-alkyl), aryl-(C$_{1-8}$-alkyl), or heteroaryl(C$_{1-8}$-alkyl), wherein the R$^3$C$_{3-8}$-cycloalkyl, heterocycloalkyl, aryl, and heteroaryl are substituted with one, two, or three $R^5$, and $R^5$ is selected from the group consisting of halogen, —OH, and —$CF_3$.

In one embodiment of formula (III), $R^3$ is $C_{3-8}$-cycloalkyl ($C_{1-8}$-alkyl), the $C_{3-8}$-cycloalkyl is an optionally substituted cyclobutyl, cyclopentyl, or cyclohexyl.

In one embodiment of formula (III), where $R^3$ is heterocycloalkyl($C_{1-8}$-alkyl), the heterocycloalkyl is an optionally substituted 5-7 membered heterocycloalkyl. In another embodiment of formula (III), the $R^3$ heterocycloalkyl is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In another embodiment of formula (I), wherein $R^3$ is heterocycloalkyl($C_{1-8}$-alkyl), the heterocycloalkyl is an optionally substituted morpholinyl or tetrahydropyranyl.

In one embodiment, wherein $R^3$ is aryl($C_{1-8}$-alkyl), the aryl is an optionally substituted phenyl.

In one embodiment, wherein $R^3$ is heteroaryl($C_{1-8}$-alkyl), the heteroaryl is an optionally substituted 5-7-membered heteroaryl. In yet another embodiment, where $R^3$ is heteroaryl ($C_{1-8}$-alkyl), the $R^3$ hetroaryl is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl. In yet another embodiment, where $R^3$ is heteroaryl($C_{1-8}$-alkyl), the $R^3$ heteroaryl is imidazolyl.

In one embodiment of formula (III), $R^4$ is hydrogen. In another embodiment of formula (III), $R^4$ is an unsubstituted branched or straight chain $C_{1-8}$ alkyl. In yet another embodiment of formula (III), $R^4$ is methyl, ethyl, propyl, isopropyl, n-butyl, sec-butyl, or t-butyl. In another embodiment of formula (III), $R^4$ is methyl. In another embodiment of formula (II), $R^4$ is a substituted branched or straight chain $C_{1-8}$ alkyl, wherein the $C_{1-8}$-alkyl is substituted with —$OR^a$ wherein $R^a$ is selected from the group consisting of H and $C_{1-8}$-alkyl. In another embodiment of formula (III), $R^4$ is a substituted branched or straight chain $C_{1-8}$ alkyl, wherein the $C_{1-8}$-alkyl is substituted with $OCH_3$.

In another embodiment of formula (III), $NR^3R^4$ is selected from the group consisting of

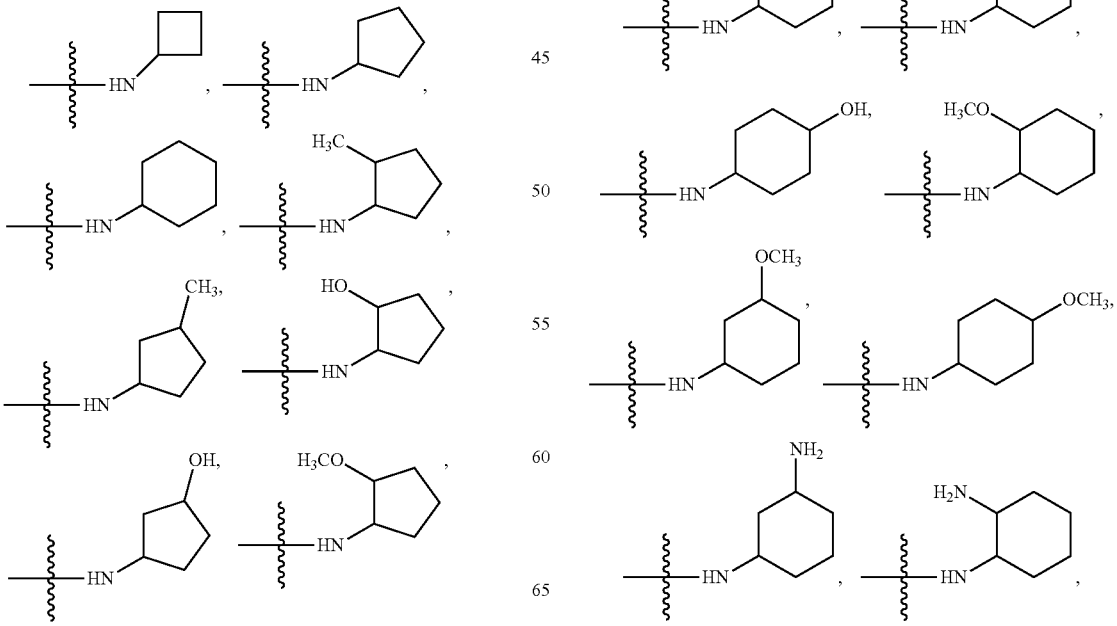

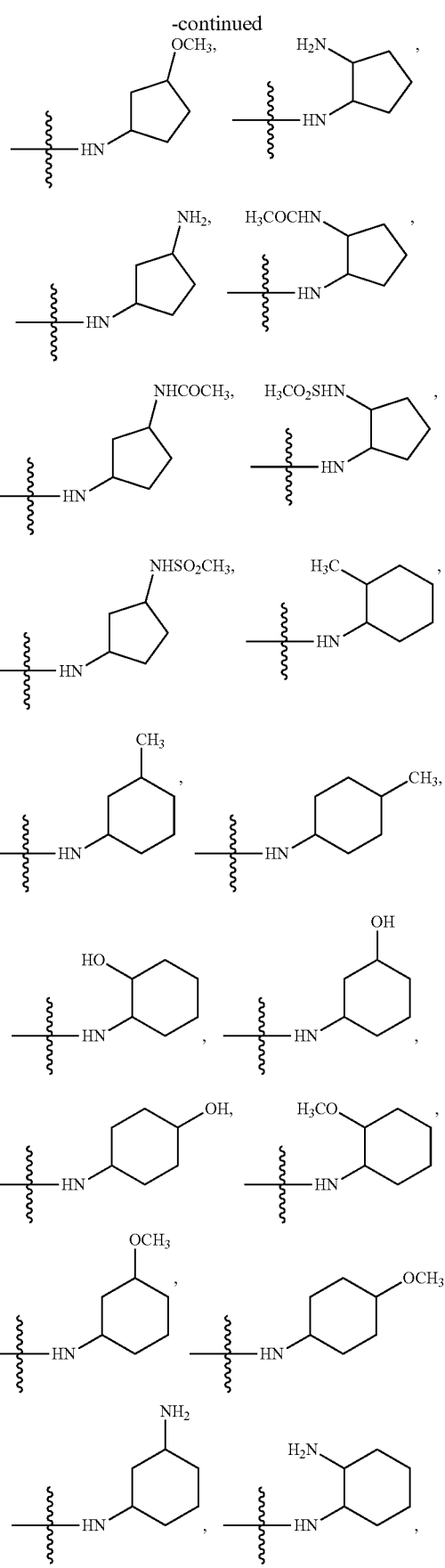

-continued
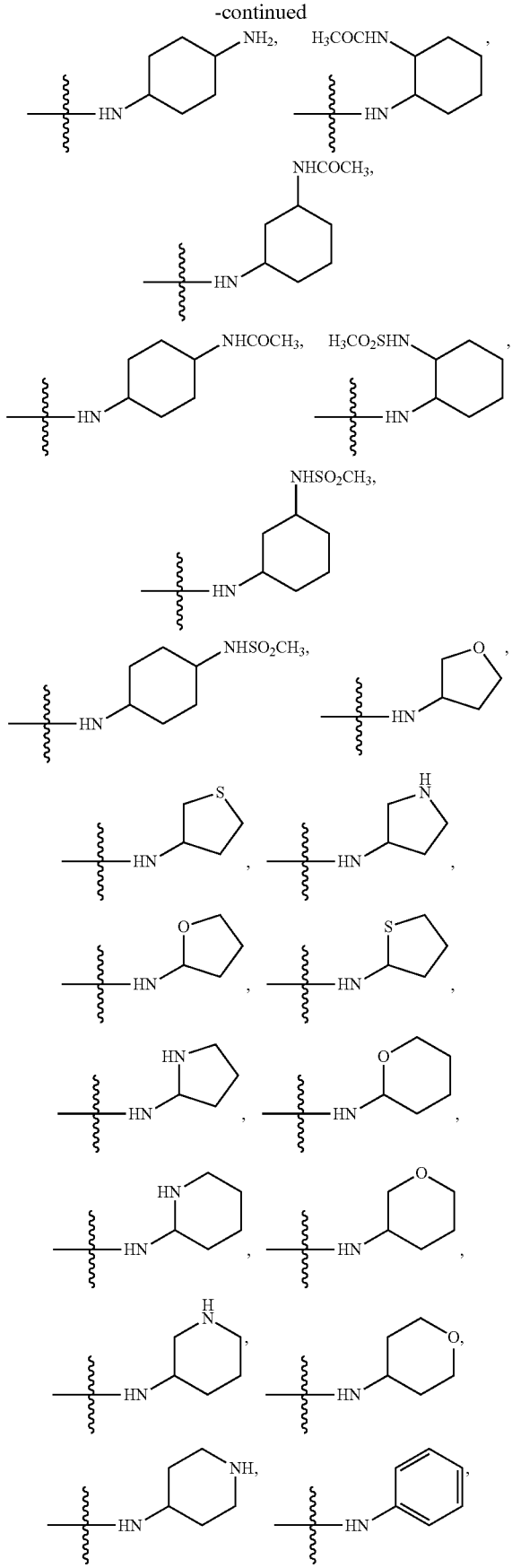
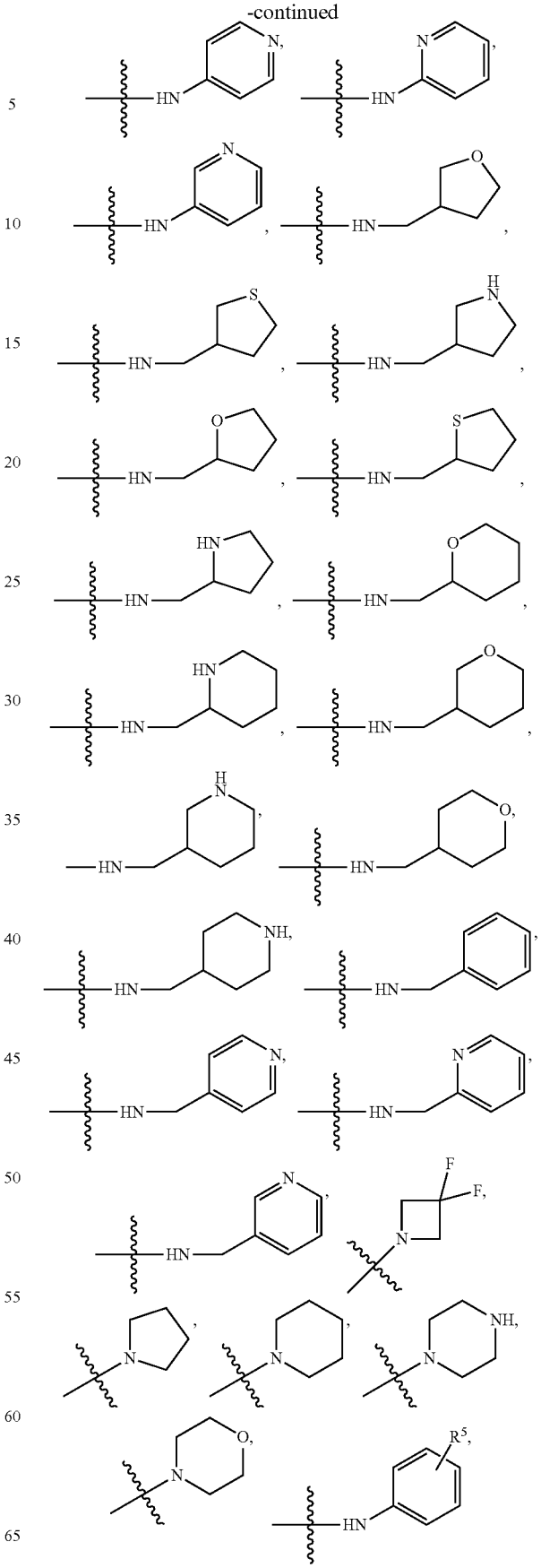

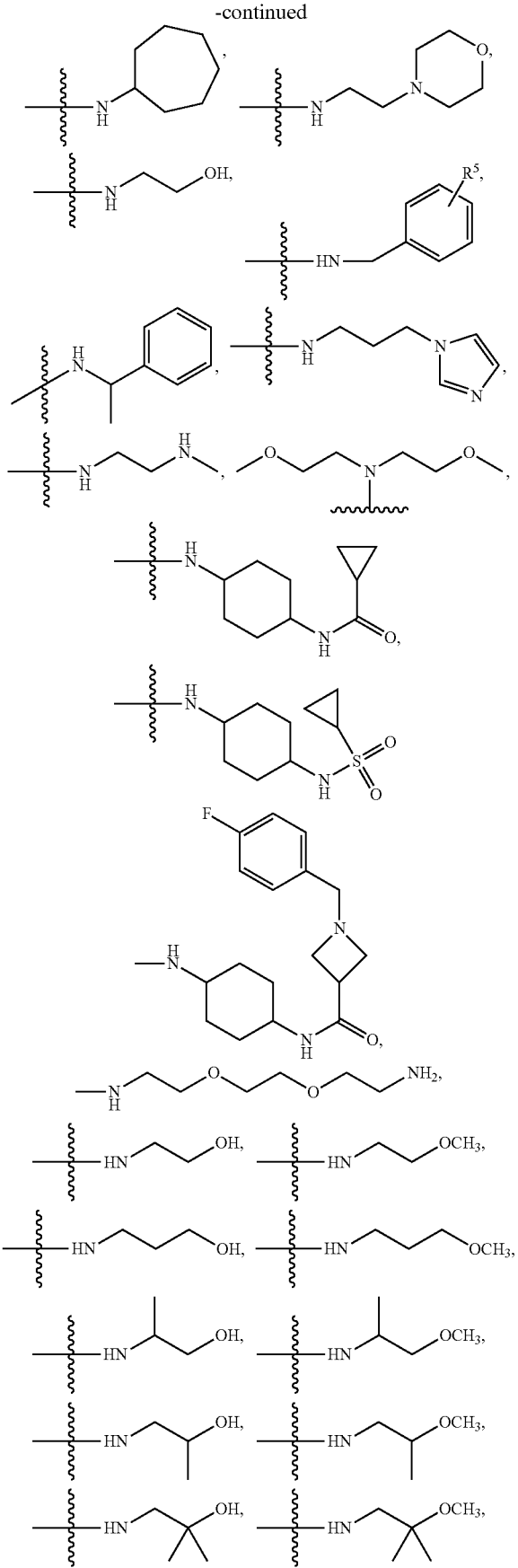
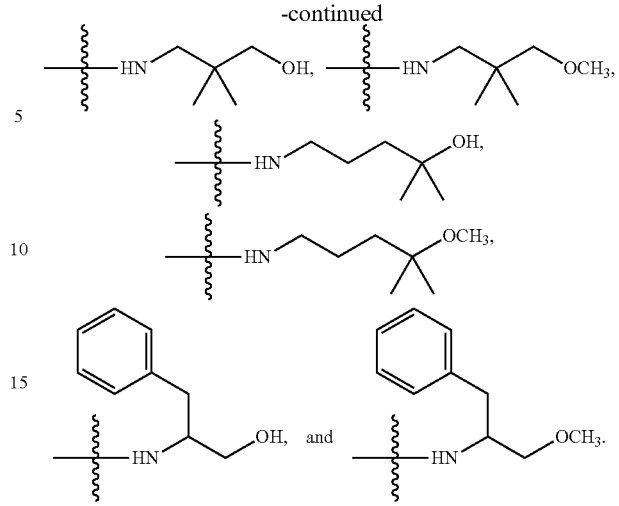

Another aspect of the invention provides compounds of formula (IV), wherein X, $R^{1a}$, $R^{1b}$, $R^{1c}$, and $R^5$ are as defined generally and in subsets above, and n is 0, 1, 2, 3, 4, or 5.

Formula (IV)

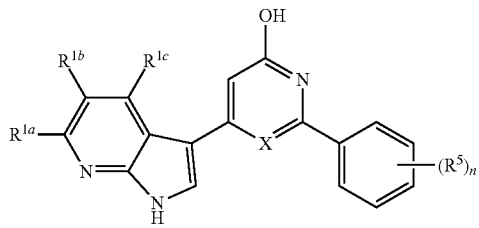

In one aspect, the present invention provides compounds of formula (IV), wherein X is N or $CR^2$;

$R^2$ is hydrogen or $C_{1-4}$-alkyl;

$R^{1a}$, $R^{1b}$, and $R^{1c}$ are independently hydrogen, hydroxy, nitro, halogen, cyano, trifluoromethyl, trifluoromethoxy, $C_{1-4}$-alkyl, —$OR^a$, —$NR^bR^c$; —$C(O)OR^a$, —$C(O)NR^bR^c$, —$NR^bC(O)R^c$, —NHC(O)$NHR^b$, or —$NHSO_2R^a$;

n is 0, 1, 2, 3, 4, or 5;

$R^5$ is selected from the group consisting of $C_{1-8}$-alkyl, $C_{2-8}$-alkenyl, $C_{2-8}$-alkynyl, aryl, heterocyclyl, halogen cyano, nitro, —$OR^d$, —$C(O)R^d$, —$C(O)OR^d$, —$OC(O)R^d$, —$NR^eR^f$, —$NR^eC(O)R^d$, —NHC(O)$NHR^e$, —$NHSO_2R^e$, —$C(O)NR^eR^f$, —$SR^d$, —$S(O)R^d$, —$SO_2R^d$, —$SO_2NR^eNR^f$, —$B(OH)_2$, —$CF_3$, —$CF_2CF_3$, —$OCF_3$, and —$OCF_2CF_3$ wherein (a) the $R^5 C_{1-8}$-alkyl, $C_{2-8}$-alkenyl, $C_{2-8}$-alkynyl, substituents are optionally substituted with one or more substituents selected from the group consisting of aryl, heterocyclyl, $C_{3-8}$-cycloalkyl, halogen, cyano, nitro, —$OR^d$, —$C(O)R^d$, —$C(O)OR^d$, —$OC(O)R^d$, —$NR^eR^f$, —$NR^eC(O)R^d$, —NHC(O)$NHR^e$, —$C(O)NR^eR^f$; and wherein (b) the $R^5$ aryl or heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, —$OR^g$, —$C(O)R^g$, —$C(O)OR^g$, —$OC(O)R^g$, —$NR^hR^i$, —$NR^hC(O)R^g$, —NHC(O)$NHR^h$, —$NHSO_2R^g$, —$C(O)NR^hR^i$, —$SR^g$, —$S(O)R^g$, —$SO_2R^g$, —$SO_2NR^hNR^i$, —$CF_3$, —$CF_2CF_3$, —$OCF_3$, and —$OCF_2CF_3$;

$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, $-NH_2$, $-NH(C_{1-8}$-alkyl), $-O(C_{1-8}$-alkyl)$NH_2$, and $-N(C_{1-8}$-alkyl)$_2$;

$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^b$ and $R^c$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, $-NH_2$, $-NH(C_{1-8}$-alkyl), and $-N(C_{1-8}$-alkyl)$_2$;

$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, aryl-($C_{1-8}$-alkyl)-, heterocyclyl, $C_{3-8}$-cycloalkyl, halogen, cyano, hydroxy, $C_{1-8}$-alkoxy, $-NH_2$, $-NH(C_{1-8}$-alkyl), and $-N(C_{1-8}$-alkyl)$_2$; wherein the aryl, aryl-($C_{1-8}$-alkyl), heterocyclyl, and $C_{3-8}$-cycloalkyl, alone or as part of another group, are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, $-NH_2$, $-NH(C_{1-8}$-alkyl), and $-N(C_{1-8}$-alkyl)$_2$;

$R^e$ and $R^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^e$ and $R^f$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, $-NH_2$, $-NH(C_{1-8}$-alkyl), and $-N(C_{1-8}$-alkyl)$_2$;

$R^g$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, $-NH_2$, $-NH(C_{1-8}$-alkyl), and $-N(C_{1-8}$-alkyl)$_2$;

$R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^i$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, $-NH_2$, $-NH(C_{1-8}$-alkyl), and $-N(C_{1-8}$-alkyl)$_2$;
or a pharmaceutically acceptable salt thereof.

In one embodiment of formula (IV), $R^{1a}$, $R^{1b}$, and $R^{1c}$ are hydrogen. In another embodiment of formula (IV), $R^{1b}$ and $R^{1c}$ are hydrogen and $R^{1a}$ is hydroxy, nitro, halogen, cyano, trifluoromethyl, trifluoromethoxy, $C_{1-4}$-alkyl, $-OR^a$, $-NR^bR^c$, $-C(O)OR^a$, $-C(O)NR^bR^c$, $-NR^bC(O)R^c$, $-NHC(O)NHR^b$, or $-NHSO_2R^a$. In another embodiment of formula (IV), $R^{1a}$ and $R^{1c}$ are hydrogen and $R^{1b}$ is hydroxy, nitro, halogen, cyano, trifluoromethyl, trifluoromethoxy, $C_{1-4}$-alkyl, $-OR^a$, $-NR^bR^c$, $-C(O)OR^a$, $-C(O)NR^bR^c$, $-NR^bC(O)R^c$, $-NHC(O)NHR^b$, or $-NHSO_2R^a$. In another embodiment of formula (IV), $R^{1c}$ is hydrogen and $R^{1a}$ and $R^{1b}$ are each independently hydroxy, nitro, halogen, cyano, trifluoromethyl, trifluoromethoxy, $C_{1-4}$-alkyl, $-OR^a$, $-NR^bR^c$, $-C(O)OR^a$, $-C(O)NR^bR^c$, $-NR^bC(O)R^c$, $-NHC(O)NHR^b$, or $-NHSO_2R^a$.

In one embodiment of formula (IV), X is N.

In another embodiment of formula (IV), X is $CR^2$ wherein $R^2$ is $C_{1-4}$-alkyl. In yet another embodiment of formula (IV), X is $CR^2$ wherein $R^2$ is hydrogen.

In another embodiment of formula (IV), n is 0. In another embodiment of formula (IV), n is 1. In another embodiment of formula (IV), n is 2. In another embodiment of formula (IV), n is 3.

In another embodiment of formula (IV), $R^5$ is selected from the group consisting of $C_{1-8}$-alkyl, $C_{2-8}$-alkenyl, $C_{2-8}$-alkynyl, aryl, heterocyclyl, halogen, oxo, cyano, nitro, $-OR^d$, $-C(O)R^d$, $-C(O)OR^d$, $-OC(O)R^d$, $-NR^eR^f$, $-NR^eC(O)R^d$, $-NHC(O)NHR^e$, $-NHSO_2R^e$, $-C(O)NR^eR^f$, $-SR^d$, $-S(O)R^d$, $-SO_2R^d$, $-SO_2NR^eNR^f$, $-B(OH)_2$, $-CF_3$, $-CF_2CF_3$, $-OCF_3$, and $-OCF_2CF_3$ wherein (a) the $R^5$ $C_{1-8}$-alkyl, $C_{2-8}$-alkenyl, $C_{2-8}$-alkynyl, substituents are optionally substituted with one or more substituents selected from the group consisting of aryl, heterocyclyl, $C_{3-8}$-cycloalkyl, halogen, cyano, nitro, oxo, $-OR^d$, $-C(O)R^d$, $-C(O)OR^d$, $-OC(O)R^d$, $-NR^eR^f$, $-NR^eC(O)R^d$, $-NHC(O)NHR^e$, $-C(O)NR^eR^f$; and wherein (b) the $R^5$ aryl or heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, oxo $-OR^g$, $-C(O)R^g$, $-C(O)OR^g$, $-OC(O)R^g$, $-NR^hR^i$, $-NR^hC(O)R^g$, $-NHC(O)NHR^h$, $-NHSO_2R^g$, $-C(O)NR^hR^i$, $-SR^g$, $-S(O)R^g$, $-SO_2R^g$, $-SO_2NR^hNR^i$, $-CF_3$, $-CF_2CF_3$, $-OCF_3$, and $-OCF_2CF_3$. In another embodiment of formula (IV), $R^5$ is selected from the group consisting of $C_{1-8}$-alkyl, heterocyclyl, halogen, $-OR^d$, $-C(O)OR^d$, $-NR^eR^f$, $-NR^eC(O)R^d$, $-NHSO_2R^e$, $-SO_2R^d$, $-CF_3$, and $-OCF_3$, wherein the $R^5 C_{1-8}$-alkyl, is optionally substituted with one or more $-OR^d$. In another embodiment of formula (IV), $R^5$ is selected from the group consisting of $C_{1-8}$-alkyl, heterocyclyl, halogen, $-OR^d$, $-C(O)OR^d$, $-NR^eR^f$, $-NR^eC(O)R^d$, $-NHSO_2R^e$, $-SO_2R^d$, $-CF_3$, and $-OCF_3$, wherein the $R^5 C_{1-8}$-alkyl, is optionally substituted with one or more $-OR^d$. $R^d$, at each occurrence, is selected from the group consisting of hydrogen, $C_{1-8}$-alkyl, heterocyclyl, and $C_{3-8}$-cycloalkyl, wherein the heterocyclyl is optionally substituted with one or more substituents independently selected from the group consisting of aryl-($C_{1-8}$-alkyl)-, wherein the aryl-($C_{1-8}$-alkyl), is optionally substituted with one or more halogen, and $R^e$ and $R^f$, at each occurrence, are independently selected from the group consisting of hydrogen, and $C_{3-8}$-cycloalkyl.

Specific embodiments contemplated as part of the invention include, but are not limited to, compounds of formula (I), for example:

2-(cyclohexylamino)-6-(1H-pyrrolo[2,3-b]pyridin-3-yl)pyrimidin-4(3H)-one;

2-(benzylamino)-6-(1H-pyrrolo[2,3-b]pyridin-3-yl)pyrimidin-4(3H)-one;
2-anilino-6-(1H-pyrrolo[2,3-b]pyrimidin-3-yl)pyrimidin-4(3H)-one;
2-[(trans-4-aminocyclohexyl)amino]-6-(1H-pyrrolo[2,3-b]pyridin-3-yl)pyrimidin-4(3H)-one;
2-[(3,5-difluorobenzyl)amino]-6-(1H-pyrrolo[2,3-b]pyridin-3-yl)pyrimidin-4(3H)-one;
2-(piperidin-4-ylamino)-6-(1H-pyrrolo[2,3-b]pyridin-3-yl)pyrimidin-4(3H)-one;
2-(4-hydroxypiperidin-1-yl)-6-(1H-pyrrolo[2,3-b]pyridin-3-yl)pyrimidin-4(3H)-one;
2-{[(1S)-1-phenylethyl]amino}-6-(1H-pyrrolo[2,3-b]pyridin-3-yl)pyrimidin-4(3H)-one;
6-(1H-pyrrolo[2,3-b]pyridin-3-yl)-2-(tetrahydro-2H-pyran-4-ylamino)pyrimidin-4(3H)-one;
6-(1H-pyrrolo[2,3-b]pyridin-3-yl)-2-[(tetrahydrofuran-2-ylmethyl)amino]pyrimidin-4(3H)-one;
2-[cyclohexyl(methyl)amino]-6-(1H-pyrrolo[2,3-b]pyridin-3-yl)pyrimidin-4(3H)-one;
2-{[(1R)-1-phenylethyl]amino}-6-(1H-pyrrolo[2,3-b]pyridin-3-yl)pyrimidin-4(3H)-one;
2-[(2-aminocyclohexyl)amino]-6-(1H-pyrrolo[2,3-b]pyridin-3-yl)pyrimidin-4(3H)-one;
2-(cycloheptylamino)-6-(1H-pyrrolo[2,3-b]pyridin-3-yl)pyrimidin-4(3H)-one;
6-(1H-pyrrolo[2,3-b]pyridin-3-yl)-2-(thiomorpholin-4-yl)pyrimidin-4(3H)-one;
2-{[2-(methylamino)ethyl]amino}-6-(1H-pyrrolo[2,3-b]pyridin-3-yl)pyrimidin-4(3H)-one;
2-[bis(2-methoxyethyl)amino]-6-(1H-pyrrolo[2,3-b]pyridin-3-yl)pyrimidin-4(3H)-one;
2-[(2-methoxyethyl)amino]-6-(1H-pyrrolo[2,3-b]pyridin-3-yl)pyrimidin-4(3H)-one;
2-[(2-hydroxyethyl)amino]-6-(1H-pyrrolo[2,3-b]pyridin-3-yl)pyrimidin-4(3H)-one;
6-(1H-pyrrolo[2,3-b]pyridin-3-yl)-2-{[2-(trifluoromethyl)benzyl]amino}pyrimidin-4(3H)-one;
2-[4-(hydroxymethyl)piperidin-1-yl]-6-(1H-pyrrolo[2,3-b]pyridin-3-yl)pyrimidin-4(3H)-one;
2-{[3-(morpholin-4-yl)propyl]amino}-6-(1H-pyrrolo[2,3-b]pyridin-3-yl)pyrimidin-4(3H)-one;
2-[(3-hydroxybenzyl)amino]-6-(1H-pyrrolo[2,3-b]pyridin-3-yl)pyrimidin-4(3H)-one;
2-(morpholin-4-yl)-6-(1H-pyrrolo[2,3-b]pyridin-3-yl)pyrimidin-4(3H)-one;
1-[6-oxo-4-(1H-pyrrolo[2,3-b]pyridin-3-yl)-1,6-dihydropyrimidin-2-yl]piperidine-4-carboxylic acid;
2-(cyclopentylamino)-6-(1H-pyrrolo[2,3-b]pyridin-3-yl)pyrimidin-4(3H)-one;
2-(4-methoxypiperidin-1-yl)-6-(1H-pyrrolo[2,3-b]pyridin-3-yl)pyrimidin-4(3H)-one;
2-[(2-hydroxycyclohexyl)amino]-6-(1H-pyrrolo[2,3-b]pyridin-3-yl)pyrimidin-4(3H)-one;
2-[(1-methylpiperidin-4-yl)amino]-6-(1H-pyrrolo[2,3-b]pyridin-3-yl)pyrimidin-4(3H)-one;
2-{[3-(1H-imidazol-1-yl)propyl]amino}-6-(1H-pyrrolo[2,3-b]pyridin-3-yl)pyrimidin-4(3H)-one;
2-({2-[2-(2-aminoethoxy)ethoxy]ethyl}amino)-6-(1H-pyrrolo[2,3-b]pyridin-3-yl)pyrimidin-4(3H)-one;
2-phenyl-6-(1H-pyrrolo[2,3-b]pyridin-3-yl)pyrimidin-4(3H)-one;
2-(2-methylphenyl)-6-(1H-pyrrolo[2,3-b]pyridin-3-yl)pyrimidin-4(3H)-one;
6-phenyl-4-(1H-pyrrolo[2,3-b]pyridin-3-yl)pyridin-2(1H)-one;
4-(1H-pyrrolo[2,3-b]pyridin-3-yl)-6-[3-(trifluoromethoxy)phenyl]pyridin-2(1H)-one;
4-(1H-pyrrolo[2,3-b]pyridin-3-yl)-6-[3-(trifluoromethyl)phenyl]pyridin-2(1H)-one;
6-(2,3-dimethylphenyl)-4-(1H-pyrrolo[2,3-b]pyridin-3-yl)pyridin-2(1H)-one;
6-(2-methylphenyl)-4-(1H-pyrrolo[2,3-b]pyridin-3-yl)pyridin-2(1H)-one;
6-(1,3-benzodioxol-5-yl)-4-(1H-pyrrolo[2,3-b]pyridin-3-yl)pyridin-2(1H)-one;
4-(1H-pyrrolo[2,3-b]pyridin-3-yl)-6-(3-thienyl)pyridin-2(1H)-one;
6-(2-naphthyl)-4-(1H-pyrrolo[2,3-b]pyridin-3-yl)pyridin-2(1H)-one;
6-(3-chlorophenyl)-4-(1H-pyrrolo[2,3-b]pyridin-3-yl)pyridin-2(1H)-one;
6-(2,3-dimethoxyphenyl)-4-(1H-pyrrolo[2,3-b]pyridin-3-yl)pyridin-2(1H)-one;
6-(2-fluoro-3-methoxyphenyl)-4-(1H-pyrrolo[2,3-b]pyridin-3-yl)pyridin-2(1H)-one;
6-(4-chloro-2-fluorophenyl)-4-(1H-pyrrolo[2,3-b]pyridin-3-yl)pyridin-2(1H)-one;
6-[2-methoxy-5-(trifluoromethyl)phenyl]-4-(1H-pyrrolo[2,3-b]pyridin-3-yl)pyridin-2(1H)-one;
2'-methoxy-4-(1H-pyrrolo[2,3-b]pyridin-3-yl)-2,3'-bipyridin-6(1H)-one;
6-(3-chloro-2-methylphenyl)-4-(1H-pyrrolo[2,3-b]pyridin-3-yl)pyridin-2(1H)-one;
3'-chloro-2'-methoxy-4-(1H-pyrrolo[2,3-b]pyridin-3-yl)-2,4'-bipyridin-6(1H)-one;
6-[3-(morpholin-4-yl)phenyl]-4-(1H-pyrrolo[2,3-b]pyridin-3-yl)pyridin-2(1H)-one;
6-[3-(methylsulfonyl)phenyl]-4-(1H-pyrrolo[2,3-b]pyridin-3-yl)pyridin-2(1H)-one;
6-(1H-pyrazol-4-yl)-4-(1H-pyrrolo[2,3-b]pyridin-3-yl)pyridin-2(1H)-one;
2'-methyl-4-(1H-pyrrolo[2,3-b]pyridin-3-yl)-2,3'-bipyridin-6(1H)-one;
6-[(3-methoxyphenyl)amino]-4-(1H-pyrrolo[2,3-b]pyridin-3-yl)pyridin-2(1H)-one;
6-anilino-4-(1H-pyrrolo[2,3-b]pyridin-3-yl)pyridin-2(1H)-one;
6-[(trans-4-aminocyclohexyl)amino]-4-(1H-pyrrolo[2,3-b]pyridin-3-yl)pyridin-2(1H)-one;
N-(trans-4-{[6-oxo-4-(1H-pyrrolo[2,3-b]pyridin-3-yl)-1,6-dihydropyridin-2-yl]amino}cyclohexyl)cyclopropanesulfonamide;
N-(trans-4-{[6-oxo-4-(1H-pyrrolo[2,3-b]pyridin-3-yl)-1,6-dihydropyridin-2-yl]amino}cyclohexyl)cyclopropanecarboxamide;
1-(4-fluorobenzyl)-N-(trans-4-{[6-oxo-4-(1H-pyrrolo[2,3-b]pyridin-3-yl)-1,6-dihydropyridin-2-yl]amino}cyclohexyl)azetidine-3-carboxamide;
2-(4-methylphenyl)-6-(1H-pyrrolo[2,3-b]pyridin-3-yl)pyrimidin-4(3H)-one;
2-(3-methylphenyl)-6-(1H-pyrrolo[2,3-b]pyridin-3-yl)pyrimidin-4(3H)-one;
2-(2,3-dimethylphenyl)-6-(1H-pyrrolo[2,3-b]pyridin-3-yl)pyrimidin-4(3H)-one; and
2-{[3-(3-aminopropoxy)benzyl]amino}-6-(1H-pyrrolo[2,3-b]pyridin-3-yl)pyrimidin-4(3H)-one.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like. Both tautomeric forms are intended to be encompassed by the scope of this invention, even though only one tautomeric form may be depicted. For example, compounds of formula (I) may tautomerise into compounds of the following structure:

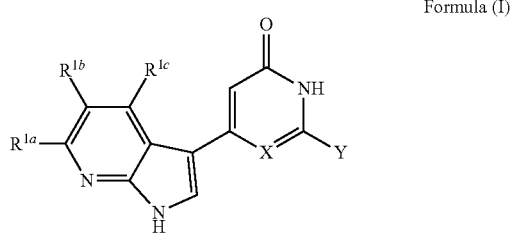

Formula (I)

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like. Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The present compounds may be prepared by a variety of processes well known for the preparation of compounds of this class. For example, the compounds of formula (I) wherein the groups X, Y, $R^{1a}$, $R^{1b}$, and $R^{1c}$ have the meanings as set forth in the summary unless otherwise noted, can be synthesized according to the general methods described in Schemes 1-5, using appropriate starting materials by methods generally available to one of ordinary skill in the art.

Abbreviations which have been used in the descriptions of the Schemes and the Examples that follow are: DMF for N,N-dimethylformamide, DMSO for dimethyl sulfoxide, DMSO-$d_6$ for deuteriated dimethyl sulfoxide, DME for dimethoxyethane, dppf for 1,1'-bis(diphenylphosphino)ferrocene, $Et_2O$ for diethyl ether, EtOAc for ethyl acetate, $Et_3N$ for triethylamine, Ts for toluene sulfonyl, and THF for tetrahydrofuran.

Schemes

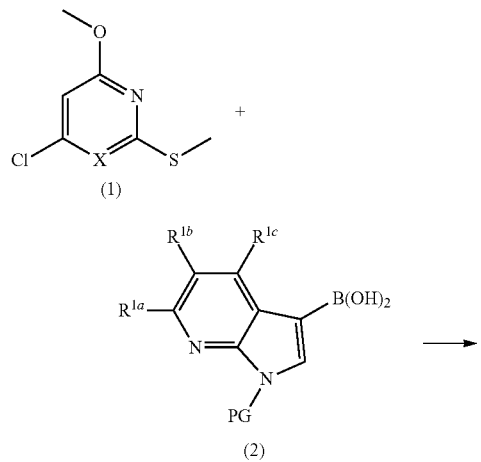

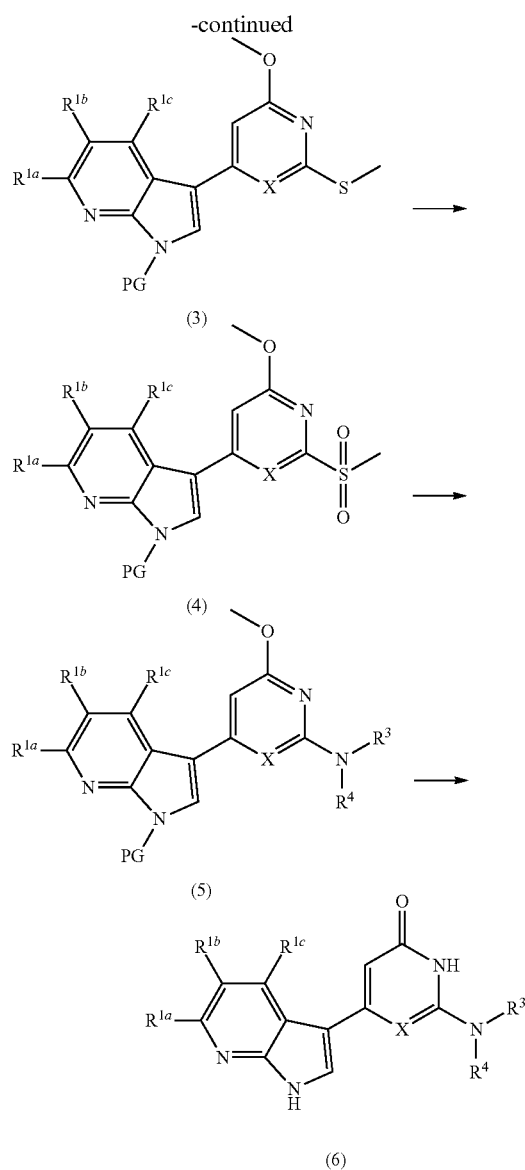

Compounds of formula (2) wherein $R^{1a}$, $R^{1b}$, and $R^{1c}$ are as described for formula (I) herein and PG is a suitable protecting group such as a benzenesulfonyl group, can be treated with compounds of formula (I) wherein X is N or $CR^2$; to provide compounds of formula (3) as shown in Scheme 1. The reaction is typically performed in the presence of a palladium catalyst and a base at elevated temperature (e.g. at about 70° C. to about 150° C. or optionally under microwave irradiation) and in a suitable solvent such as DMF, dioxane, ethanol, water, DME, or mixtures thereof. Non-limiting examples of suitable palladium catalysts include dichlorobis(triphenylphosphine) palladium (II), $PdCl_2(dppf)_2$, and tetrakis(triphenylphosphine) palladium. Suitable bases include, but are not limited to, cesium fluoride, sodium carbonate, potassium acetate, cesium carbonate. Oxidation of the methylthio functionality in compounds of formula (3) with an oxidizing agent such as, but not limited to, OXONE® in a suitable solvent such as methanol/$H_2O$ or ethyl acetate/$H_2O$ provides compounds of formula (4).

Displacement of the methylsulfonyl group of compounds of formula (4) with amines of formula $N(H)R^3R^4$, wherein $R^3$ and $R^4$ are as described for formula (I) herein, will provide compounds of formula (5). The reaction can be conducted in a suitable solvent (e.g. dioxane) or in excess of the amine employed, at a temperature from about 60° C. to about 150° C., optionally in the presence of a base (e.g. triethylamine, or diisopropylethyl amine) and optionally under microwave irradiation. Compounds of formula (6), which are representative of compounds of this invention, can be prepared by reacting compounds of formula (5) with an aqueous base such as but not limited to sodium hydroxide or potassium hydroxide in a solvent such as but not limited to dioxane, or ethanol to remove the protecting group, followed by a work-up and subsequent treatment with an acid such but not limited to aqueous HCl.

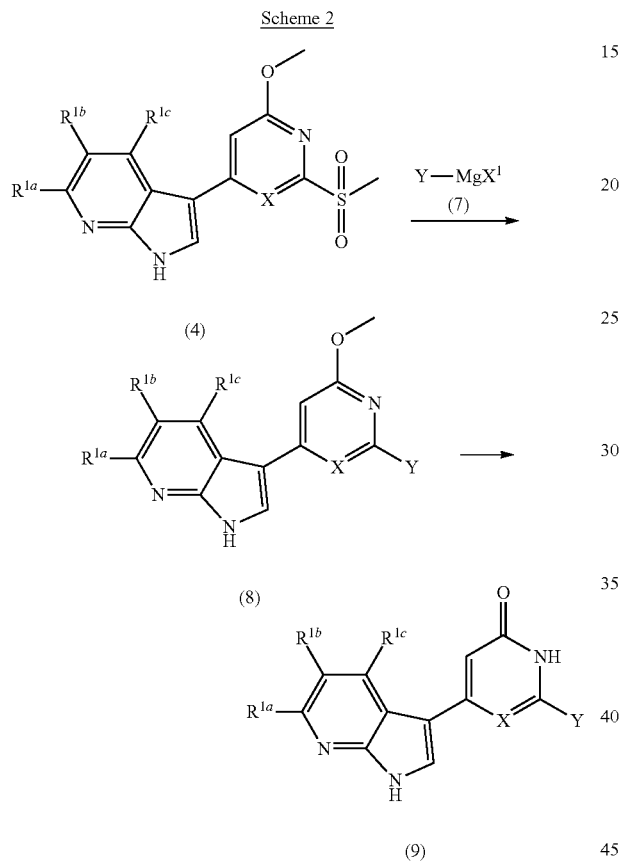

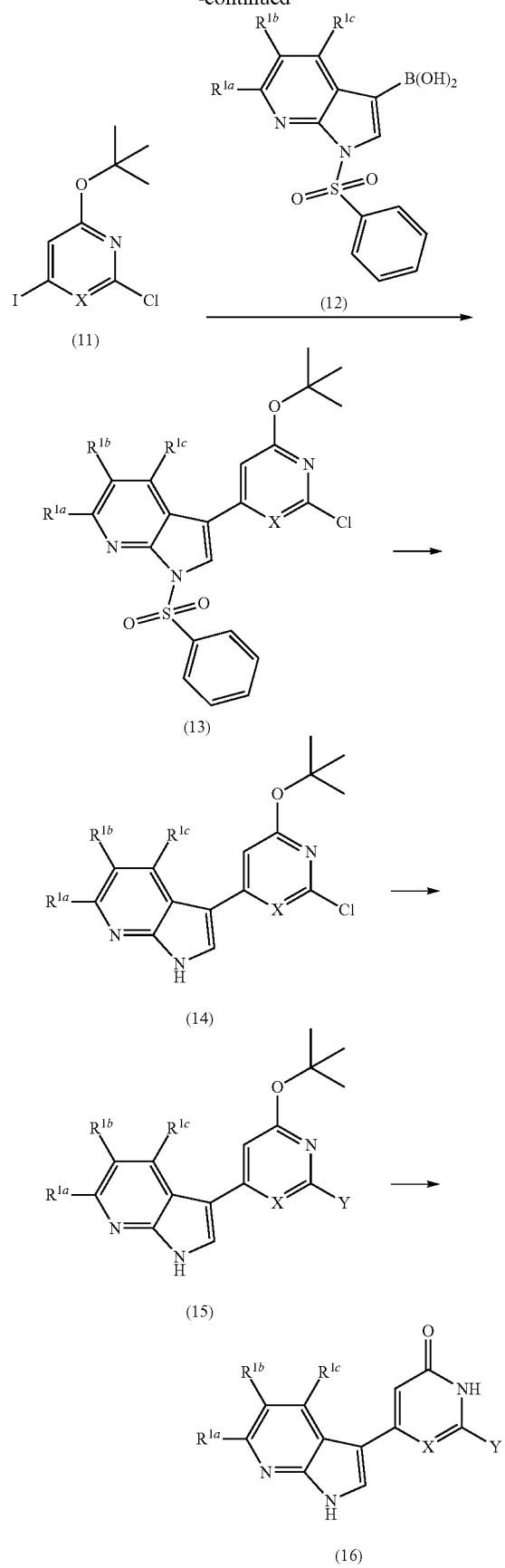

As shown in Scheme 2, compounds of formula (4) can be reacted with a Grignard reagent of formula (7) wherein Y is as aryl or heterocyclyl and $X^1$ is a halogen such as I, Br, or Cl or a pseudohalide such as a triflate. The Grignard reagent is typically added at low temperature, followed by the addition of an aqueous base such as but not limited to sodium hydroxide at ambient temperature. Addition of an acid such as but not limited to hydrochloric acid at an elevated temperature will provide compounds of formula (9), which are representative of the compounds of this invention.

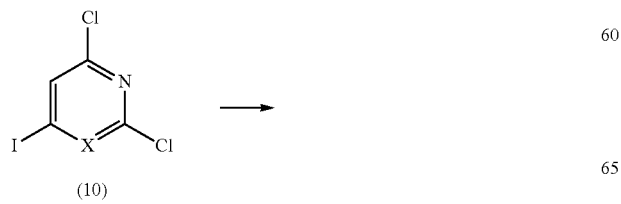

As shown in Scheme 3, compounds of formula (11) can be prepared from compounds of formula (10) by treating the latter with potassium tert-butoxide at reflux. Compounds of formula (12), wherein $R^{1a}$, $R^{1b}$, and $R^{1c}$ are as described for formula (I) herein, can be reacted with compounds of formula (11) to provide compounds of formula (13). The reaction is typically performed in the presence of a palladium catalyst and a base at elevated temperature (e.g. at about 70° C. to about 150° C. or optionally under microwave irradiation) and in a suitable solvent such as DMF, dioxane, ethanol, water, DME, or mixtures thereof. Non-limiting examples of suitable palladium catalysts include dichlorobis(triphenylphosphine) palladium (II), $PdCl_2(dppf)_2$, and tetrakis(triphenylphosphine) palladium. Suitable bases include, but are not limited to, sodium carbonate, potassium acetate, cesium carbonate. Removal of the benzenesulfonyl group from compounds of formula (13) with an aqueous base such as but not limited to sodium hydroxide or potassium hydroxide, will provide compounds of formula (14). The reaction is typically performed at an elevated temperature and may include an additional solvent such as but not limited to dioxane or ethanol. Compounds of formula (14) can be reacted with a boronic acid (Y—B(OH)$_2$) or a boron-ester wherein Y is aryl or heteroaryl, to provide compounds of formula (15). The reaction is typically performed in the presence of a palladium catalyst and a base at elevated temperature (e.g. at about 70° C. to about 150° C. or optionally under microwave irradiation) and in a suitable solvent such as DMF, dioxane, ethanol, water, DME, or mixtures thereof. Non-limiting examples of suitable palladium catalysts include dichlorobis(triphenylphosphine) palladium (II), $PdCl_2(dppf)_2$, and tetrakis(triphenylphosphine) palladium. Suitable bases include, but are not limited to, cesium fluoride, sodium carbonate, potassium acetate, cesium carbonate. Addition of an acid such as but not limited to trifluoroacetic acid at ambient or an elevated temperature will provide compounds of formula (16), which are representative of compounds of this invention.

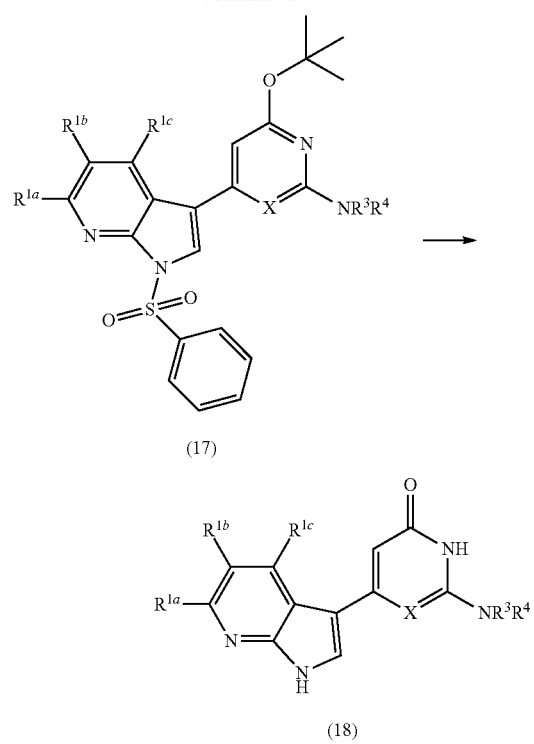

As shown in Scheme 4, direct displacement of the chloro in compounds of formula (13) with amines of formula N(H)$R^3R^4$ will provide compounds of formula (17). The reaction can be conducted in a suitable solvent (e.g. dioxane) or in excess of the amines employed, at a temperature from about 60° C. to about 150° C., optionally in the presence of a base (e.g. triethylamine, diisopropylethyl amine) and optionally under microwave irradiation. Addition of an acid such as but not limited to p-toluenesulfonic acid will provide compounds of formula (18), which are representative of compounds of this invention.

Scheme 4

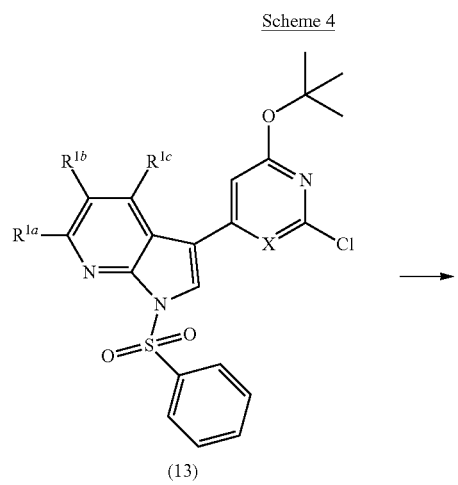

Scheme 5

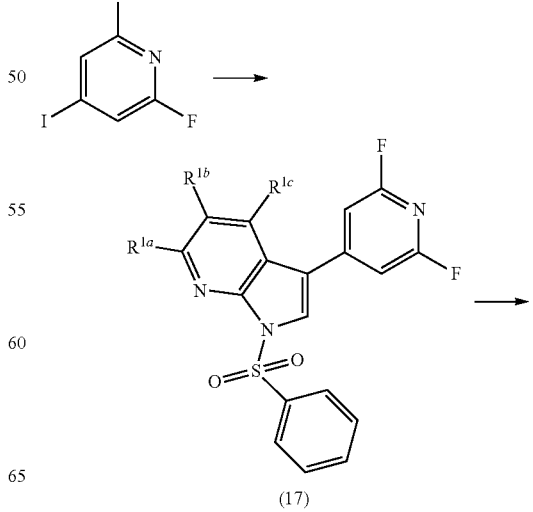

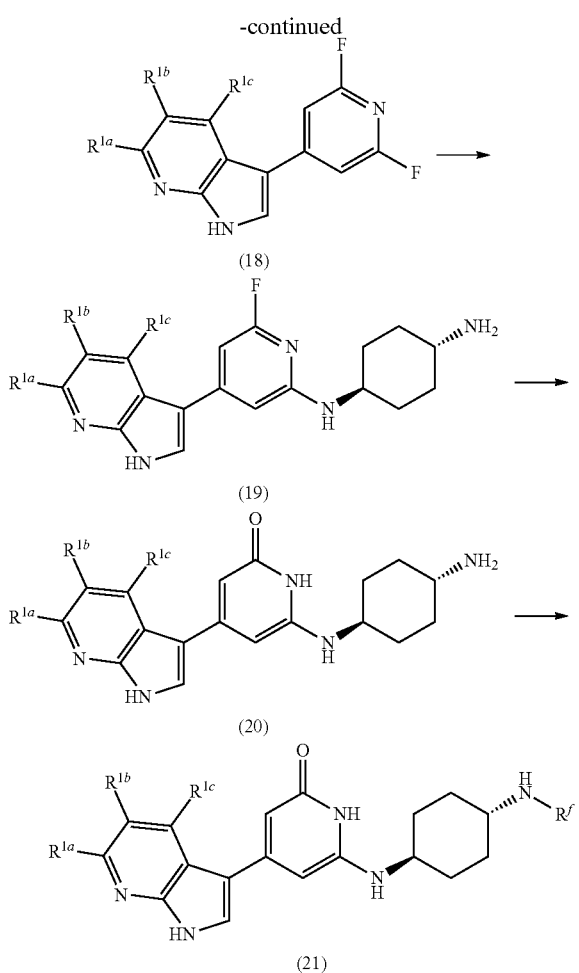

As shown in scheme 5, 2,6-difluoro-4-iodopyridine can be reacted with compounds of formula (12) to provide compounds of formula (17). The reaction is typically performed in the presence of a palladium catalyst and a base at elevated temperature (e.g. at about 70° C. to about 150° C. or optionally under microwave irradiation) and in a suitable solvent such as DMF, dioxane, ethanol, water, DME, or mixtures thereof. Non-limiting examples of suitable palladium catalysts include dichlorobis(triphenylphosphine) palladium (II), $PdCl_2(dppf)_2$, and tetrakis(triphenylphosphine) palladium. Suitable bases include, but are not limited to, sodium carbonate, potassium acetate, cesium carbonate. Removal of the benzenesulfonyl group from compounds of formula (17) with an aqueous base such as but not limited to sodium hydroxide or potassium hydroxide, will provide compounds of formula (18). The reaction is typically performed at an elevated temperature and may include an additional solvent such as but not limited to dioxane or ethanol. Displacement of the fluoro in compounds of formula (18) with trans-cyclohexane-1,4-diamine, will provide compounds of formula (19). The reaction is typically performed under microwave irradiation in a solvent such as but not limited to ethanol. Compounds of formula (19) can be heated using microwave irradiation with an aqueous acid such as but not limited to hydrochloric acid in a solvent such as but not limited to tert-butanol to provide compounds of formula (20). Compounds of formula (21), which are representative of compounds of this invention, can be prepared by reacting compounds of formula (20) by reacting the latter with compounds of formula $R^fSO_2Cl$, $R^fC(O)H$, $R^fC(O)OH$, $R^fC(O)Cl$ or $R^fC(O)OH$ under suitable coupling or reduction amination reaction conditions described herein, known to those skilled in the art, and readily available in the literature.

Unless otherwise noted, microwave reactions described herein were carried out either in a Biotage Initiator 8 or in a CEM Explorer at 200 W. All reverse-phase HPLC purifications were carried out using a Zorbax C-18, 250×2.54 column and a eluting with a 0-100% gradient of mobile phase A (0.1% trifluoroacetic acid (TFA) in water) and mobile phase B (0.1% TFA in $CH_3CN$).

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperitoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all CDC-7 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered.

The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide) or ABT-737 (i.e., N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-(3-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-veMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN®(naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARD10×ANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-nl, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine) (ONCOVIN®; P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTATAAE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zoledronic acid), zorubicin and the like.

The following examples are presented to provide what is believed to be the most useful and readily understood description of procedures and conceptual aspects of this invention. The exemplified compounds were named using ACD/ChemSketch, Release 12.00 Version 12.01 (13 May 2009, Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

EXAMPLES

Example 1

2-(cyclohexylamino)-6-(1H-pyrrolo[2,3-b]pyridin-3-yl)pyrimidin-4(3H)-one

Example 1A 3-(6-methoxy-2-(methylthio)pyrimidin-4-yl)-1-(phenylsulfonyl)-1H-pyrrolo[2,3-b]pyridine A mixture of 4-chloro-6-methoxy-2-(methylthio)pyrimidine (10.2 g, 53.7 mmol), 1-(phenylsulfonyl)-3-(4,4,5,5-tetramethyl-1,3,2-dioxaborolan-2-yl)-1H-pyrrolo[2,3-b]pyridine (18.8 g, 48.8 mmol), potassium carbonate (48.8 g, 98 mmol), and tetrakis(triphenylphosphine) palladium (2.26 g, 1.95 mmol) in 9/1 dimethoxyethane/N,N-dimethylformamide (200 mL) was evacuated under vacuum and refilled with nitrogen and heated at 85° C. for 20 minutes. The cooled mixture was filtered to give the title compound.

Example 1B 3-(6-methoxy-2-(methylsulfonyl)pyrimidin-4-yl)-1-(phenylsulfonyl)-1H-pyrrolo[2,3-b]pyridine A mixture of EXAMPLE 1A (6.2 g, 15.0 mmol) and OXONE® (92 g, 150 mmol) in ethyl acetate (350 mL) was stirred at 77° C. for 2 days. The mixture was filtered and the solids were washed with dichloromethane and concentrated to give the title compound.

Example 1C

N-cyclohexyl-4-methoxy-6-(1-(phenylsulfonyl)-1H-pyrrolo[2,3-b]pyridin-3-yl)pyrimidin-2-amine A solution of EXAMPLE 1B (6.7 g, 15.1 mmol) and cyclohexanamine (6.90 mL, 60.3 mmol) in dioxane (165 mL) was heated at 100° C. overnight. The mixture was concentrated to afford the crude title compound which was directly used in the next step.

Example 1D 2-(cyclohexylamino)-6-(1H-pyrrolo[2,3-b]pyridin-3-yl)pyrimidin-4(3H)-one hydrochloride To EXAMPLE 1C (6.99 g, ~15.1 mmol) was added dioxane (150 mL) and aqueous 1M NaOH (75 mL, 75 mmol). The mixture was heated at 100° C. for 1.5 hours and concentrated. The residue was partitioned between water and dichloromethane and the organic layer dried over sodium sulfate, filtered through silica gel with ethyl acetate, and concentrated. The residue was dissolved in 12% aqueous HCl (55 mL, 199 mmol) and heated at 80° C. for 2 days. The cooled mixture was filtered, and the crude HCl salt was isolated.

Example 1E

2-(cyclohexylamino)-6-(1H-pyrrolo[2,3-b]pyridin-3-yl)pyrimidin-4(3H)-one

The HCl salt from EXAMPLE 1D was dissolved in methanol (500 mL) and 7M ammonia in methanol (13.9 mL, 97 mmol) was added dropwise. The mixture was stirred at room temperature for 10 minutes and concentrated. The residue was washed with water and concentrated to provide the title compound as the free base. MS (ESI) m/e 310 (M+H)$^+$; $^1$H NMR (DMSO-d$_6$) δ 1.17-1.81 (m, 8H), 1.93-2.07 (m, 2H), 3.71-3.98 (m, 1H), 6.05 (s, 1H), 6.37 (d, J=6.35 Hz, 1H), 7.15 (dd, J=8.13, 4.56 Hz, 1H), 8.19 (d, J=2.78 Hz, 1H), 8.25 (dd, J=4.76, 1.59 Hz, 1H), 8.63 (d, J=7.14 Hz, 1H), 10.17 (s, 1H), 12.11 (s, 1H).

Example 22

22-(benzylamino)-6-(1H-pyrrolo[2,3-b]pyridin-3-yl)pyrimidin-4(3H)-one

The title compound was prepared as the free base using the procedure described for EXAMPLE 1 replacing cyclohexanamine with benzylamine MS (ESI) m/e 318 (M+H)$^+$; $^1$H NMR (DMSO-d$_6$) δ 4.65 (d, J=5.83 Hz, 2H), 6.08 (s, 1H), 6.92 (s, 1H), 7.06 (dd, J=7.98, 4.91 Hz, 1H), 7.26 (t, J=7.21 Hz, 1H), 7.32-7.47 (m, 4H), 8.16 (d, J=1.53 Hz, 1H), 8.22 (dd, J=4.60, 1.84 Hz, 1H), 8.38-8.50 (m, 1H), 10.57 (s, 1H), 12.07 (s, 1H).

Example 3

2-anilino-6-(1H-pyrrolo[2,3-b]pyridin-3-yl)pyrimidin-4(3H)-one

A mixture of EXAMPLE 1B (0.089 g, 0.20 mmol), and aniline (0.2 mL) in N-methylpyrrolidone (3 mL) was heated in a microwave at 235° C. for 1.5 hours. The mixture was concentrated and purified by reverse phase HPLC to provide the title compound. MS (ESI) m/e 304 (M+H)$^+$; $^1$H NMR (DMSO-d$_6$) δ 6.33 (s, 1H), 7.06-7.18 (m, 2H), 7.34-7.45 (m, 2H), 7.68 (d, J=7.67 Hz, 2H), 8.23 (s, 1H), 8.26-8.31 (m, 1H), 8.56 (d, J=7.67 Hz, 1H), 8.84 (s, 1H), 12.22 (s, 1H).

Example 4

2-[(trans'-4-aminocyclohexyl)amino]-6-(1H-pyrolo[2,3-b]pyridin-3-yl)pyrimidin-4(3H)-one The title compound was prepared as the HCl salt using the procedure described for EXAMPLE 1 replacing cyclohexanamine with trans-1,4-diaminocyclohexane. MS (ESI) m/e 325 (M+H)$^+$; $^1$H NMR (DMSO-d$_6$) δ 1.29-1.48 (m, 2H), 1.50-1.65 (m, 2H), 2.05 (t, J=14.49 Hz, 4H), 3.08 (d, J=4.27 Hz, 1H), 3.84 (s, 1H), 6.46 (s, 1H), 7.34 (s, 1H), 8.26 (d, J=4.27 Hz, 3H), 8.36-8.45 (m, 1H), 8.45-8.56 (m, 1H), 8.76 (s, 1H), 9.23 (s, 1H), 12.91 (s, 1H).

Example 5

2-[(3,5-difluorobenzyl)amino]-6-(1H-pyrrolo[2,3-b]pyridin-3-yl)pyrimidin-4(3H)-one The title compound was prepared as the HCl salt using the procedure described for EXAMPLE 1 replacing cyclohexanamine with (3,5-difluorophenyl)methanamine MS (ESI) m/e 354 (M+H)$^+$; $^1$H NMR (DMSO-d$_6$) δ 4.72 (d, J=3.38 Hz, 2H), 6.40 (s, 1H), 6.94-7.43 (m, 5H), 8.20-8.73 (m, 4H), 12.70 (s, 1H).

Example 6

2-(piperidin-4-ylamino)-6-(1H-pyrrolo[2,3-b]pyridin-3-yl)pyrimidin-4(3H)-one The title compound was prepared as the HCl salt using the procedure described for EXAMPLE 1 replacing cyclohexanamine with piperidin-4-amine MS (ESI) m/e 311 (M+H)$^+$; $^1$H NMR (DMSO-d$_6$) δ 1.29-1.43 (m, 2H), 1.81-1.92 (m, 5H), 2.98-3.12 (m, 3H), 4.44 (d, J=13.20 Hz, 2H), 6.16 (s, 1H), 7.18 (dd, J=7.83, 4.76 Hz, 1H), 8.22 (s, 1H), 8.26 (dd, J=4.60, 1.53 Hz, 1H), 8.55 (dd, J=7.98, 1.23 Hz, 1H).

Example 7

2-(4-hydroxypiperidin-1-yl)-6-(1H-pyrrolo[2,3-b]pyridin-3-yl)pyrimidin-4(3H)-one The title compound was prepared as the HCl salt using the procedure described for EXAMPLE 1 replacing cyclohexanamine with piperidin-4-ol. MS (ESI) m/e 312 (M+H)$^+$; $^1$H NMR (DMSO-d$_6$) δ 1.38-1.57 (m, 2H), 1.76-1.96 (m, 2H), 3.37-3.55 (m, 2H), 3.75-3.88 (m, 1H), 4.07-4.21 (m, 2H), 6.38 (s, 1H), 7.44 (dd, J=7.98, 5.22 Hz, 1H), 8.39-8.47 (m, 1H), 8.74 (d, J=7.67 Hz, 1H), 12.99 (s, 1H).

Example 8

2-{[(1S)-1-phenylethyl]amino}-6-(1H-pyrrolo[2,3-b]pyridin-3-yl)pyrimidin-4(3H)-one The title compound was prepared as the HCl salt using the procedure described for EXAMPLE 1 replacing cyclohexanamine with (S)-1-phenylethanamine. MS (ESI) m/e 332 (M+H)$^+$; $^1$H NMR (DMSO-d$_6$) δ 1.51 (d, J=6.75 Hz, 3H), 5.19 (q, J=6.85 Hz, 1H), 6.04 (s, 1H), 6.92 (s, 1H), 7.07 (dd, J=7.98, 4.60 Hz, 1H), 7.24 (t, J=7.36 Hz, 1H), 7.33-7.48 (m, 4H), 8.11 (s, 1H), 8.22 (dd, J=4.60, 1.53 Hz, 1H), 8.34 (d, J=7.67 Hz, 1H), 10.27 (s, 1H), 12.04 (s, 1H).

Example 9

6-(1H-pyrrolo[2,3-b]pyridin-3-yl)-2-(tetrahydro-2H-pyran-4-ylamino)pyrimidin-4(3H)-one The title compound was prepared as the HCl salt using the procedure described for EXAMPLE 1 replacing cyclohexanamine with tetrahydro-2H-pyran-4-amine MS (ESI) m/e 332 (M+H)$^+$; $^1$H NMR (DMSO-d$_6$) δ 1.37-1.67 (m, 2H), 1.96 (d, J=10.68 Hz, 2H), 3.45 (t, J=10.22 Hz, 2H), 3.85-3.96 (m, 2H), 4.05-4.18 (m, 2H), 6.46 (s, 1H), 7.28-7.38 (m, 1H), 8.35-8.47 (m, 1H), 8.46-8.59 (m, 1H), 8.75 (s, 1H), 9.37 (d, J=5.49 Hz, 1H), 12.90 (s, 1H).

Example 10

6-(1H-pyrrolo[2,3-b]pyridin-3-yl)-2-[(tetrahydrofuran-2-ylmethyl)amino]pyrimidin-4(3H)-one The title compound was prepared as the HCl salt using the procedure described for EXAMPLE 1 replacing cyclohexanamine with (tetrahydrofuran-2-yl)methanamine MS (ESI)

m/e 325 (M+H)+; 1H NMR (DMSO-d6) δ 1.54-1.70 (m, 1H), 1.77-2.09 (m, 3H), 3.48-3.74 (m, 3H), 3.81-3.90 (m, 1H), 3.98-4.10 (m, 1H), 6.49 (s, 1H), 7.29-7.39 (m, 1H), 8.42 (dd, J=4.88, 1.22 Hz, 1H), 8.50 (s, 1H), 8.84 (s, 1H), 9.02 (s, 1H), 12.92 (s, 1H).

Example 11

2-[cyclohexyl(methyl)amino]-6-(1H-pyrrolo[2,3-b]pyridin-3-yl)pyrimidin-4(3H)-one The title compound was prepared as the HCl salt using the procedure described for EXAMPLE 1 replacing cyclohexanamine with N-methylcyclohexanamine MS (ESI) m/e 324 (M+H)+; 1H NMR (DMSO-d6) δ 1.07-1.25 (m, 1H), 1.34-1.76 (m, 7H), 1.83 (d, J=12.58 Hz, 2H), 2.98 (s, 3H), 4.51 (t, J=11.35 Hz, 1H), 6.10 (s, 1H), 7.17 (dd, J=7.98, 4.60 Hz, 1H), 8.20 (d, J=2.15 Hz, 1H), 8.26 (dd, J=4.60, 1.23 Hz, 1H), 8.57-8.68 (m, 1H), 10.70 (s, 1H), 12.08 (s, 1H).

Example 12

2-{[(1R)-1-phenylethyl]amino}-6-(1H-pyrrolo[2,3-b]pyridin-3-yl)pyrimidin-4(3H)-one The title compound was prepared as the HCl salt using the procedure described for EXAMPLE 1 replacing cyclohexanamine with (R)-1-phenylethanamine MS (ESI) m/e 332 (M+H)+; 1H NMR (DMSO-d6) δ 1.51 (d, J=6.75 Hz, 3H), 5.19 (q, J=7.06 Hz, 1H), 6.04 (s, 1H), 6.92 (s, 1H), 7.07 (dd, J=7.98, 4.60 Hz, 1H), 7.24 (t, J=7.36 Hz, 1H), 7.37 (t, J=7.67 Hz, 2H), 7.41-7.47 (m, 2H), 8.10 (s, 1H), 8.22 (dd, J=4.60, 1.53 Hz, 1H), 8.34 (d, J=7.67 Hz, 1H), 10.26 (s, 1H), 12.03 (s, 1H).

Example 13

2-[(2-aminocyclohexyl)amino]-6-(1H-pyrrolo[2,3-b]pyridin-3-yl)pyrimidin-4(3H)-one The title compound was prepared as the HCl salt using the procedure described for EXAMPLE 1 replacing cyclohexanamine with cyclohexane-1,2-diamine MS (ESI) m/e 325 (M+H)+; 1H NMR (DMSO-d6) δ 1.19-2.19 (m, 10H), 3.02-3.19 (m, 1H), 4.07 (s, 1H), 7.19-7.49 (m, 2H), 8.14-8.65 (m, 5H), 12.96 (s, 1H).

Example 14

2-(cycloheptylamino)-6-(1H-pyrrolo[2,3-b]pyridin-3-yl)pyrimidin-4(3H)-one

The title compound was prepared as the HCl salt using the procedure described for EXAMPLE 1 replacing cyclohexanamine with cycloheptanamine MS (ESI) m/e 324 (M+H)+; 1H NMR (DMSO-d6) δ 1.44-1.74 (m, 10H), 1.91-2.08 (m, 2H), 3.95-4.15 (m, 1H), 6.06 (s, 1H), 6.37 (s, 1H), 7.15 (dd, J=7.97, 4.58 Hz, 1H), 8.19 (d, J=2.37 Hz, 1H), 8.25 (dd, J=4.75, 1.69 Hz, 1H), 8.64 (d, J=8.14 Hz, 1H), 10.17 (s, 1H), 12.13 (s, 1H).

Example 15

6-(1H-pyrrolo[2,3-b]pyridin-3-yl)-2-(thiomorpholin-4-yl)pyrimidin-4(3H)-one

The title compound was prepared as the HCl salt using the procedure described for EXAMPLE 1 replacing cyclohexanamine with thiomorpholine. MS (ESI) m/e 314 (M+H)+; 1H NMR (DMSO-d6) δ 2.61-2.75 (m, 4H), 3.99-4.14 (m, 4H), 6.21 (s, 1H), 7.18 (dd, J=7.93, 4.88 Hz, 1H), 8.21-8.31 (m, 2H), 8.53 (d, J=7.32 Hz, 1H), 10.99 (s, 1H), 12.16 (s, 1H).

Example 16

2-{[2-(methylamino)ethyl]amino}-6-(1H-pyrrolo[2,3-b]pyridin-3-yl)pyrimidin-4(3H)-one The title compound was prepared as the HCl salt using the procedure described for EXAMPLE 1 replacing cyclohexanamine with N1-methylethane-1,2-diamine. MS (ESI) m/e 285 (M+H)+; 1H NMR (DMSO-d6) δ 2.35 (s, 3H), 2.70-2.80 (m, 2H), 3.43-3.54 (m, 3H), 6.05 (s, 1H), 6.60 (s, 1H), 7.15 (dd, J=7.97, 4.58 Hz, 1H), 8.18 (s, 1H), 8.25 (dd, J=4.58, 1.53 Hz, 1H), 8.62 (dd, J=8.14, 1.70 Hz, 1H).

Example 17

2-[bis(2-methoxyethyl)amino]-6-(1H-pyrrolo[2,3-b]pyridin-3-yl)pyrimidin-4(3H)-one The title compound was prepared as the HCl salt using the procedure described for EXAMPLE 1 replacing cyclohexanamine with bis(2-methoxyethyl)amine MS (ESI) m/e 344 (M+H)+; 1H NMR (DMSO-d6) δ 3.30 (s, 6H), 3.61 (t, J=5.06 Hz, 4H), 3.76-3.95 (m, 4H), 6.36 (s, 1H), 7.34-7.43 (m, 1H), 8.38-8.44 (m, 1H), 8.36 (s, 1H), 8.81 (d, J=7.36 Hz, 1H), 12.85 (s, 1H).

Example 18

2-[(2-methoxyethyl)amino]-6-(1H-pyrrolo[2,3-b]pyridin-3-yl)pyrimidin-4(3H)-one

The title compound was prepared as the HCl salt using the procedure described for EXAMPLE 1 replacing cyclohexanamine with 2-methoxyethanamine MS (ESI) m/e 286 (M+H)+; 1H NMR (DMSO-d6) δ 3.32 (s, 3H), 3.52-3.65 (m, 4H), 6.08 (s, 1H), 6.47-6.58 (m, 1H), 7.16 (dd, J=7.93, 4.88 Hz, 1H), 8.20 (d, J=1.22 Hz, 1H), 8.26 (dd, J=4.58, 1.53 Hz, 1H), 8.61 (d, J=7.02 Hz, 1H), 10.47 (s, 1H), 12.13 (s, 1H).

Example 19

2-[(2-hydroxyethyl)amino]-6-(1H-pyrrolo[2,3-b]pyridin-3-yl)pyrimidin-4(3H)-one

The title compound was prepared as the HCl salt using the procedure described for EXAMPLE 1 replacing cyclohexanamine with 2-aminoethanol. MS (ESI) m/e 272 (M+H)+; 1H NMR (DMSO-d6) δ 3.50 (q, J=5.42 Hz, 2H), 3.62 (t, J=5.52 Hz, 2H), 6.05 (s, 1H), 6.61 (s, 1H), 7.16 (dd, J=7.98, 4.60 Hz, 1H), 8.17 (s, 1H), 8.25 (dd, J=4.60, 1.53 Hz, 1H), 8.60 (dd, J=7.98, 1.53 Hz, 1H).

Example 20

6-(1H-pyrrolo[2,3-b]pyridin-3-yl)-2-{[2-(trifluoromethyl)benzyl]amino}pyrimidin-4(3H)-one The title compound was prepared as the HCl salt using the procedure described for EXAMPLE 1 replacing cyclohexanamine with (2-(trifluoromethyl)phenyl)methanamine MS (ESI) m/e 386 (M+H)+; 1H NMR (DMSO-d6) δ 4.89 (d, J=4.30 Hz, 2H), 6.48 (s, 1H), 7.23 (s, 1H), 7.46-7.59 (m, 1H), 7.70 (d, J=3.99 Hz, 2H), 7.80 (d, J=7.67 Hz, 1H), 8.27-8.93 (m, 3H), 12.81 (s, 1H).

Example 21

2-[4-(hydroxymethyl)piperidin-1-yl]-6-(1H-pyrrolo[2,3-b]pyridin-3-yl)pyrimidin-4(3H)-one The title compound was prepared as the HCl salt using the procedure described for EXAMPLE 1 replacing cyclohexanamine with piperidin-4-ylmethanol. MS (ESI) m/e 326 (M+H)$^+$; $^1$H NMR (DMSO-d$_6$) δ 1.05-1.35 (m, 2H), 1.59-1.88 (m, 3H), 3.03 (t, J=12.04 Hz, 2H), 3.30 (d, J=5.76 Hz, 2H), 4.51 (d, J=12.89 Hz, 2H), 6.29 (s, 1H), 7.36 (dd, J=8.14, 5.09 Hz, 1H), 8.30-8.45 (m, 2H), 8.67 (d, J=7.80 Hz, 1H), 12.73 (s, 1H).

Example 22

2-{[3-(morpholin-4-yl)propyl]amino}-6-(1H-pyrrolo[2,3-b]pyridin-3-yl)pyrimidin-4(3H)-one The title compound was prepared as the HCl salt using the procedure described for EXAMPLE 1 replacing cyclohexanamine with 3-morpholinopropan-1-amine MS (ESI) m/e 355 (M+H)$^+$; $^1$H NMR (DMSO-d$_6$) δ 1.66-1.83 (m, 2H), 2.25-2.43 (m, 6H), 3.45 (q, J=6.44 Hz, 2H), 3.52-3.65 (m, 5H), 6.04 (s, 1H), 6.74 (s, 1H), 7.15 (dd, J=7.98, 4.60 Hz, 1H), 8.16 (s, 1H), 8.23-8.29 (m, 1H), 8.58-8.68 (m, 1H).

Example 23

2-[(3-hydroxybenzyl)amino]-6-(1H-pyrrolo[2,3-b]pyridin-3-yl)pyrimidin-4(3H)-one

The title compound was prepared as the HCl salt using the procedure described for EXAMPLE 1 replacing cyclohexanamine with 3-(aminomethyl)phenol. MS (ESI) m/e 334 (M+H)$^+$; $^1$H NMR (DMSO-d$_6$) δ 4.63 (d, J=3.68 Hz, 2H), 6.48 (s, 1H), 6.66-6.74 (m, 1H), 6.78-6.87 (m, 2H), 7.17 (t, J=7.83 Hz, 1H), 7.32 (dd, J=7.98, 4.91 Hz, 1H), 8.41 (d, J=3.68 Hz, 1H), 8.52 (d, J=7.06 Hz, 1H), 8.73 (s, 1H), 9.22 (s, 1H), 12.86 (s, 1H).

Example 24

2-(morpholin-4-yl)-6-(1H-pyrrolo[2,3-b]pyridin-3-yl)pyrimidin-4(3H)-one

The title compound was prepared as the HCl salt using the procedure described for EXAMPLE 1 replacing cyclohexanamine with morpholine. MS (ESI) m/e 298 (M+H)$^+$; $^1$H NMR (DMSO-d$_6$) δ 3.56-3.83 (m, 8H), 6.22 (s, 1H), 7.18 (dd, J=7.98, 4.60 Hz, 1H), 8.16-8.37 (m, 2H), 8.55 (d, J=7.98 Hz, 1H), 10.95 (s, 1H), 12.12 (s, 1H).

Example 25

1-[6-oxo-4-(1H-pyrrolo[2,3-b]pyridin-3-yl)-1,6-dihydropyrimidin-2-yl]piperidine-4-carboxylic acid The title compound was prepared as the HCl salt using the procedure described for EXAMPLE 1 replacing cyclohexanamine with piperidine-4-carboxamide. MS (ESI) m/e 340 (M+H)$^+$; $^1$H NMR (DMSO-d$_6$) δ 1.54-1.73 (m, 2H), 1.90-2.00 (m, 2H), 2.56-2.69 (m, 1H), 3.16-3.31 (m, 2H), 4.39 (d, J=13.50 Hz, 2H), 6.37 (s, 1H), 7.43 (dd, J=7.98, 5.22 Hz, 1H), 8.38-8.48 (m, 2H), 8.76 (d, J=7.67 Hz, 1H), 12.94 (s, 1H).

Example 26

2-(cyclopentylamino)-6-(1H-pyrrolo[2,3-b]pyridin-3-yl)pyrimidin-4(3H)-one

The title compound was prepared as the HCl salt using the procedure described for EXAMPLE 1 replacing cyclohexanamine with cyclopentanamine MS (ESI) m/e 295 (M+H)$^+$; $^1$H NMR (DMSO-d$_6$) δ 1.45-1.79 (m, 6H), 1.91-2.13 (m, 2H), 4.21-4.39 (m, 1H), 6.06 (s, 1H), 6.40-6.51 (m, 1H), 7.16 (dd, J=7.98, 4.60 Hz, 1H), 8.18 (d, J=1.84 Hz, 1H), 8.25 (dd, J=4.60, 1.53 Hz, 1H), 8.64 (dd, J=7.98, 1.23 Hz, 1H), 10.13 (s, 1H), 12.09 (s, 1H).

Example 27

2-(4-methoxypiperidin-1-yl)-6-(1H-pyrrolo[2,3-b]pyridin-3-yl)pyrimidin-4(3H)-one The title compound was prepared as the HCl salt using the procedure described for EXAMPLE 1 replacing cyclohexanamine with 4-methoxypiperidine. MS (ESI) m/e 326 (M+H)$^+$; $^1$H NMR (DMSO-d$_6$) δ 1.46-1.60 (m, 2H), 1.88-2.00 (m, 2H), 3.30 (s, 3H), 3.42-3.57 (m, 3H), 4.00-4.14 (m, 2H), 6.34 (s, 1H), 7.40 (dd, J=7.21, 5.06 Hz, 1H), 8.40 (s, 2H), 8.73 (d, J=7.67 Hz, 1H), 12.85 (s, 1H).

Example 28

2-[(2-hydroxycyclohexyl)amino]-6-(1H-pyrrolo[2,3-b]pyridin-3-yl)pyrimidin-4(3H)-one The title compound was prepared as the HCl salt using the procedure described for EXAMPLE 1 replacing cyclohexanamine with 2-aminocyclohexanol. MS (ESI) m/e 326 (M+H)$^+$; $^1$H NMR (DMSO-d$_6$) δ 1.13-1.79 (m, 8H), 2.98-3.09 (m, 1H), 3.86-3.93 (m, 1H), 5.88 (s, 1H), 7.29 (dd, J=7.93, 4.88 Hz, 1H), 7.81-7.95 (m, 2H), 8.31-8.40 (m, 2H), 10.97 (d, J=30.82 Hz, 1H), 12.65 (s, 1H).

Example 29

2-[(1-methylppiperidin-4-yl)amino]-6-(1H-pyrrolo[2,3-b]pyridin-3-yl)pyrimidin-4(3H)-one The title compound was prepared as the HCl salt using the procedure described for EXAMPLE 1 replacing cyclohexanamine with 1-methylpiperidin-4-amine MS (ESI) m/e 325 (M+H)$^+$; $^1$H NMR (DMSO-d$_6$) δ 1.47-1.60 (m, 2H), 1.93-2.02 (m, 2H), 2.06-2.16 (m, 2H), 2.21 (s, 3H), 2.68-2.79 (m, 2H), 3.78-3.92 (m, 1H), 6.04 (s, 1H), 6.88-7.01 (m, 1H), 7.15 (dd, J=7.98, 4.60 Hz, 1H), 8.17 (s, 1H), 8.23-8.27 (m, 1H), 8.61 (dd, J=7.98, 1.53 Hz, 1H).

Example 30

2-{[3-(1H-imidazol-1-yl)propyl]amino}-6-(1H-pyrrolo[2,3-b]pyridin-3-yl)pyrimidin-4(3H)-one The title compound was prepared as the HCl salt using the procedure described for EXAMPLE 1 replacing cyclohexanamine with 3-(1H-imidazol-1-yl)propan-1-amine MS (ESI) m/e 336 (M+H)$^+$; $^1$H NMR (DMSO-d$_6$) δ 2.00-2.10 (m, 2H), 3.17 (s, 1H), 3.33-3.40 (m, 2H), 3.51-3.59 (m, 1H), 4.09 (t, J=6.90 Hz, 2H), 6.06 (s, 1H), 6.78-6.86 (m, 1H), 6.92 (s, 1H), 7.17 (dd, J=7.98, 4.60 Hz, 1H), 7.22 (s, 1H), 7.67 (s, 1H), 8.15 (s, 1H), 8.25 (dd, J=4.60, 1.53 Hz, 1H), 8.52 (dd, J=7.98, 1.53 Hz, 1H).

Example 31

2-({2-[2-(2-amino ethoxy)ethoxy]ethyl}amino)-6-(1H-pyrrolo[2,3-b]pyridin-3-yl)pyrimidin-4(3H)-one The title compound was prepared as the HCl salt using the procedure described for EXAMPLE 1 replacing cyclohexanamine with 2,2'-(ethane-1,2-diylbis(oxy))diethanamine MS (ESI) m/e 359 (M+H)$^+$; $^1$H NMR (DMSO-d$_6$) δ 2.74 (t, J=5.59 Hz, 2H), 3.45 (t, J=5.76 Hz, 2H), 3.51-3.69 (m, 8H), 6.04 (s, 1H), 7.00-7.11 (m, 1H), 7.15 (dd, J=7.97, 4.58 Hz, 1H), 8.18 (s, 1H), 8.25 (dd, J=4.75, 1.70 Hz, 1H), 8.60 (dd, J=8.14, 1.70 Hz, 1H).

Example 32

2-phenyl-6-(1H-pyrrolo[2,3-b]pyridin-3-yl)pyrimidin-4(3H)-one

To a solution of EXAMPLE 1B (89 mg, 0.20 mmol) in 1,2-dimethoxyethane (2 mL) at 0° C. was added dropwise 3M phenylmagnesium bromide in diethyl ether (0.133 mL, 0.40 mmol)). The mixture was slowly warmed to room temperature and stirred for 15 minutes. To the solution was added dropwise 1M aqueous sodium hydroxide (2 mL, 2 mmol). The mixture was stirred at room temperature for 1 day and concentrated. The residue was dissolved in 12% aqueous HCl (0.62 mL, 2.25 mmol) and heated at 90° C. for 4 hours. The mixture was concentrated and purified by reverse phase HPLC to provide the title compound. MS (ESI) m/e 289 (M+H)$^+$; $^1$H NMR (DMSO-d$_6$) δ 6.78 (s, 1H), 7.25 (dd, J=7.93, 4.58 Hz, 1H), 7.54-7.65 (m, 3H), 8.24-8.34 (m, 3H), 8.44 (s, 1H), 8.69-8.75 (m, 1H), 12.32 (s, 1H).

Example 33

2-(2-methylphenyl)-6-(1H-pyrrolo[2,3-b]pyridin-3-yl)pyrimidin-4(3H)-one

The title compound was prepared using the procedure described for EXAMPLE 32 replacing phenylmagnesium bromide with o-tolylmagnesium bromide. MS (ESI) m/e 303 (M+H)$^+$; $^1$H NMR (DMSO-d$_6$) δ 2.45 (s, 3H), 6.74 (s, 1H), 7.17 (dd, J=7.93, 4.58 Hz, 1H), 7.31-7.41 (m, 2H), 7.45 (t, J=7.48 Hz, 1H), 7.55 (d, J=7.63 Hz, 1H), 8.28 (dd, J=4.58, 1.53 Hz, 1H), 8.32 (s, 1H), 8.55 (d, J=7.32 Hz, 1H), 12.28 (s, 1H), 12.42 (s, 1H).

Example 34

6-phenyl-4-(1H-pyrrolo[2,3-b]pyridin-3-yl)pyridin-2(1H)-one

Example 34A 2-tert-butoxy-6-chloro-4-iodopyridine

To a solution of 2,6 dichloro-4-iodo pyridine (1 g, 3.65 mmol) in 15 mL tetrahydrofuran was added 1M potassium tert-butoxide (4.02 mL, 4.02 mmol) and the solution heated at reflux for 2 hours. The mixture was diluted with ethyl acetate, washed with water and brine and dried over magnesium sulfate, filtered and concentrated. The crude material was used without further purification. MS (DCI) m/e 312.0 (M+H)$^+$.

Example 34B 3-(2-tert-butoxy-6-chloropyridin-4-yl)-1-(phenylsulfonyl)-1H-pyrrolo[2,3-b]pyridine To a solution of EXAMPLE 34A (2.6 g, 8.35 mmol) in 5:1 dimethoxyethane/ethanol (90 mL) was added 1-(phenylsulfonyl)-3-(4,4,5,5-tetramethyl-1,3,2-dioxaborolan-2-yl)-1H-pyrrolo[2,3-b]pyridine (3.53 g, 9.18 mmol), 1M aqueous sodium carbonate (6.68 mL) and dichlorobis(triphenylphosphine)-palladium (II) (0.29 g, 0.42 mmol). The reaction was heated at 80° C. for 3 hours, cooled, and diluted with ethyl acetate. The solution was washed with brine, dried over magnesium sulfate, filtered and concentrated to give the title compound. MS (ESI) m/e 442.0 (M+H)$^+$.

Example 34C 3-(2-tert-butoxy-6-chloropyridin-4-yl)-1H-pyrrolo[2,3-b]pyridine To a suspension of EXAMPLE 34B (2.15 g, 4.87 mmol) in 60 mL ethanol/water (5:1) was added powdered potassium hydroxide (1.09 g, 19.46 mmol). The suspension was heated at 50° C. for 3 hours, at which time the reaction was homogeneous. The solvent was removed and the crude material was dissolved in ethyl acetate, washed with water, and brine, dried over magnesium sulfate, filtered and concentrated. The crude material was purified by flash chromatography (Analogix280, gradient elution, 20-100% ethyl acetate/hexane) to give the title compound. MS (ESI) m/e 301.9 (M+H)$^+$.

Example 34D 3-(2-tert-butoxy-6-phenylpyridin-4-yl)-1H-pyrrolo[2,3-b]pyridine To a solution of EXAMPLE 34C (0.13 g, 0.43 mmol) in 7:3:2 dimethoxyethane/ethanol/water (3 mL) was added phenyl boronic acid (0.053 g, 0.43 mmol), 1M aqueous sodium carbonate (0.6 mL) and dichlorobis(triphenylphosphine)-palladium (II) (0.015 g, 0.022 mmol). The solution was heated to 160° C. in a CEM microwave @100 W for 20 minutes. The crude material was diluted with ethyl acetate, washed with brine, dried over magnesium sulfate, filtered, and concentrated. Purification by flash chromatography (Analogix 280, gradient elution, 5-75% ethyl acetate/hexane) gave the title compound. MS (ESI) m/e 344.0 (M+H)$^+$.

Example 34E 6-phenyl-4-(1H-pyrrolo[2,3-b]pyridin-3-yl)pyridin-2(1H)-one

To a solution of EXAMPLE 34D in 1 mL dichloromethane was added 1 mL trifluoroacetic acid. The solution was stirred at room temperature for 25 minutes and the solvent was removed. The crude material was diluted with ethyl acetate and washed with saturated sodium bicarbonate and brine, dried over magnesium sulfate, filtered, and concentrated to give the title compound. MS (ESI) m/e 287.9 (M+H)$^+$; $^1$H NMR (DMSO-d$_6$) δ 6.70 (s, 1H), 7.03 (s, 1H), 7.11-7.30 (m, 1H), 7.37-7.64 (m, 3H), 7.76-8.01 (m, 2H), 8.18-8.48 (m, 3H), 11.52 (s, 1H), 12.23 (s, 1H).

Example 35

4-(1H-pyrrolo[2,3-b]pyridin-3-yl)-6-[3-(trifluoromethoxy)phenyl]pyridin-2(1H)-one

Example 35A 3-(2-tert-butoxy-6-(3-(trifluoromethoxy)phenyl)pyridin-4-yl)-1H-pyrrolo[2,3-b]pyridine The title compound was prepared using the procedure described for EXAMPLE 34D substituting 3-(trifluoromethoxy)phenylboronic acid for phenyl boronic acid. MS (ESI) m/e 428.0 (M+H)

Example 35B 4-(1H-pyrrolo[2,3-b]pyridin-3-yl)-6-(3-(trifluoromethoxy)phenyl)pyridin-2(1H)-one To a solution EXAMPLE 35A (0.065 g, 0.152 mmol) in 1 mL dichloromethane was added trifluoroacetic acid (1 mL) and the solution stirred at room temperature for 1 hour. The solvent was removed and the crude material dried over high-vacuum for several hours to give the title compound as the trifluoroacetate salt. MS (ESI) m/e 371.9 (M+H)$^+$; $^1$H NMR (DMSO-d$_6$) δ 6.83 (s, 1H), 7.13-7.37 (m, 2H), 7.48 (d, J=8.14 Hz, 1H), 7.65 (t, J=7.97 Hz, 1H), 7.80-8.12 (m, 2H), 8.21-8.55 (m, 3H), 12.31 (s, 1H).

Example 36

4-(1H-pyrrolo[2,3-b]pyridin-3-yl)-6-[3-(trifluoromethyl)phenyl]pyridin-2(1H)-one

Example 36A 3-(2-tert-butoxy-6-(3-(trifluoromethyl)phenyl)pyridin-4-yl)-1H-pyrrolo[2,3-b]pyridine The title compound was prepared using the procedure described for EXAMPLE 34D substituting 3-(trifluoromethyl)phenylboronic acid for phenyl boronic acid. MS (ESI) m/e 428.0 (M+H).

Example 36B 4-(1H-pyrrolo[2,3-b]pyridin-3-yl)-6-(3-(trifluoromethyl)phenyl)pyridin-2(1H)-one The title compound was prepared as the trifluoroacetate salt using the procedure described for EXAMPLE 35B substituting EXAMPLE 36A for EXAMPLE 35A. MS (ESI) m/e 355.9 (M+H)±; $^1$H NMR (DMSO-d$_6$) δ 6.85 (d, J=1.36 Hz, 1H), 7.25 (dd, J=7.97, 4.58 Hz, 2H), 7.35 (s, 1H), 7.63-7.94 (m, 3H), 8.15-8.53 (m, 3H), 12.33 (s, 1H).

Example 37

6-(2,3-dimethylphenyl)-4-(1H-pyrrolo[2,3-b]pyridin-3-yl)pyridin-2(1H)-one

Example 37A 3-(2-tert-butoxy-6-(2,3-dimethylphenyl)pyridin-4-yl)-1H-pyrrolo[2,3-b]pyridine The title compound was prepared using the procedure described for EXAMPLE 34D substituting 2,3-dimethylphenylboronic acid for phenyl boronic acid. MS (ESI) m/e 372.0 (M+H)$^+$.

Example 37B 6-(2,3-dimethylphenyl)-4-(1H-pyrrolo[2,3-b]pyridin-3-yl)pyridin-2(1H)-one The title compound was prepared as the trifluoroacetate salt using the procedure described for EXAMPLE 35B substituting EXAMPLE 37A for EXAMPLE 35A. MS (ESI) m/e 315.9 (M+H)$^+$; $^1$H NMR (DMSO-d$_6$) δ 2.21 (s, 3H), 2.32 (s, 3H), 6.74 (d, J=1.70 Hz, 1H), 6.81 (d, J=1.36 Hz, 1H), 7.09-7.44 (m, 5H), 8.15-8.54 (m, 3H), 12.38 (d, J=2.03 Hz, 1H).

Example 38

6-(2-methylphenyl)-4-(1H-pyrrolo[2,3-b]pyridin-3-yl)pyridin-2(1H)-one

Example 38A 3-(2-tert-butoxy-6-o-tolylpyridin-4-yl)-1H-pyrrolo[2,3-b]pyridine The title compound was prepared using the procedure described for EXAMPLE 34D substituting 2-methylphenyl boronic acid for phenyl boronic acid. MS (ESI) m/e 358.0 (M+H)$^+$

Example 38B 4-(1H-pyrrolo[2,3-b]pyridin-3-yl)-6-o-tolylpyridin-2(1H)-one

The title compound was prepared as the trifluoroacetate salt using the procedure described for EXAMPLE 35B substituting EXAMPLE 38A for EXAMPLE 35A. MS (ESI) m/e 301.9 (M+H)$^+$; $^1$H NMR (DMSO-d$_6$) δ 2.35 (s, 3H), 6.74 (d, J=1.70 Hz, 1H), 6.78 (d, J=1.70 Hz, 1H), 7.24 (dd, J=7.80, 4.75 Hz, 1H), 7.29-7.46 (m, 4H), 8.08-8.53 (m, 3H), 12.36 (s, 1H).

Example 39

6-(1,3-benzodioxol-5-yl)-4-(1H-pyrrolo[2,3-b]pyridin-3-yl)pyridin-2(1H)-one

Example 39A 3-(2-(benzo[d][1,3]dioxol-5-yl)-6-tert-butoxypyridin-4-yl)-1H-pyrrolo[2,3-b]pyridine The title compound was prepared using the procedure described for EXAMPLE 34D substituting benzo[d][1,3]dioxol-5-ylboronic acid for phenyl boronic acid. MS (ESI) m/e 388.0 (M+H)$^+$.

Example 39B

6-(benzo[d][1,3]dioxol-5-yl)-4-(1H-pyrrolo[2,3-b]pyridin-3-yl)pyridin-2(1H)-one The title compound was prepared as the trifluoroacetate salt using the procedure described for EXAMPLE 35B substituting EXAMPLE 39A for EXAMPLE 35A. MS (ESI) m/e 331.9 (M+H)$^+$; $^1$H NMR (DMSO-d$_6$) δ 6.07-6.19 (m, 2H), 6.74 (d, J=1.70 Hz, 1H), 7.05 (s, 1H), 7.07 (s, 1H), 7.25 (dd, J=8.14, 4.75 Hz, 1H), 7.44 (dd, J=8.14, 2.03 Hz, 1H), 7.52 (d, J=2.03 Hz, 1H), 8.07-8.54 (m, 3H), 12.36 (s, 1H).

Example 40

4-(1H-pyrrolo[2,3-b]pyridin-3-yl)-6-(3-thienyl)pyridin-2(1H)-one

Example 40A

3-(2-tert-butoxy-6-(thiophen-3-yl)pyridin-4-yl)-1H-pyrrolo[2,3-b]pyridine

The title compound was prepared using the procedure described for EXAMPLE 34D substituting thiophen-3-ylboronic acid for phenyl boronic acid. MS (ESI) m/e 350.0 (M+H)$^+$.

Example 40B

4-(1H-pyrrolo[2,3-b]pyridin-3-yl)-6-(thiophen-3-yl)pyridin-2(1H)-one

The title compound was prepared as the trifluoroacetate salt using the procedure described for EXAMPLE 35B substituting EXAMPLE 40A for EXAMPLE 35A. MS (ESI) m/e 293.8 (M+H)$^+$; $^1$H NMR (DMSO-d$_6$) δ 6.72 (d, J=1.70 Hz, 1H), 7.20 (d, J=1.36 Hz, 1H), 7.26 (dd, J=8.14, 4.75 Hz, 1H), 7.73 (dd, J=5.09, 3.05 Hz, 1H), 7.84 (dd, J=5.09, 1.36 Hz, 1H), 8.19-8.50 (m, 4H), 12.40 (s, 1H).

Example 41

6-(2-naphthyl)-4-(1H-pyrrolo[2,3-b]pyridin-3-yl)pyridin-2(1H)-one

Example 41A

3-(2-tert-butoxy-6-(naphthalen-2-yl)-1,2-dihydropyridin-4-yl)-1H-pyrrolo[2,3-b]pyridine The title compound was prepared using the procedure described for EXAMPLE 34D substituting naphthalen-2-ylboronic acid for phenyl boronic acid. MS (ESI) m/e 394.0 (M+H)$^+$.

Example 41B

6-(naphthalen-2-yl)-4-(1H-pyrrolo[2,3-b]pyridin-3-yl)pyridin-2(1H)-one

The title compound was prepared as the trifluoroacetate salt using the procedure described for EXAMPLE 35B substituting EXAMPLE 41A for EXAMPLE 35A. MS (ESI) m/e 338.0 (M+H)$^+$; $^1$H NMR (DMSO-d$_6$) δ 6.82 (d, J=1.59 Hz, 1H), 7.19-7.37 (m, 2H), 7.61 (dd, J=6.35, 3.17 Hz, 2H), 7.92-8.12 (m, 4H), 8.35 (d, J=3.17 Hz, 1H), 8.38-8.48 (m, 2H), 8.51 (s, 1H), 12.19-12.57 (m, 1H).

Example 42

6-(3-chlorophenyl)-4-(1H-pyrrolo[2,3-b]pyridin-3-yl)pyridin-2(1H)-one

Example 42A

3-(2-tert-butoxy-6-(3-chlorophenyl)-1,2-dihydropyridin-4-yl)-1H-pyrrolo[2,3-b]pyridine The title compound was prepared using the procedure described for EXAMPLE 34D substituting 3-chlorophenylboronic acid for phenyl boronic acid. MS (ESI) m/e 378.0 (M+H)$^+$.

Example 42B

6-(3-chlorophenyl)-4-(1H-pyrrolo[2,3-b]pyridin-3-yl)pyridin-2(1H)-one

The title compound was prepared as the trifluoroacetate salt using the procedure described for EXAMPLE 35B substituting EXAMPLE 42A for EXAMPLE 35A. MS (ESI) m/e 321.9 (M+H)$^+$; $^1$H NMR (DMSO-d$_6$) δ 6.79 (s, 1H), 7.23 (dd, J=7.93, 4.76 Hz, 2H), 7.53 (t, J=4.76 Hz, 2H), 7.82-7.97 (m, 1H), 8.03 (s, 1H), 8.19-8.51 (m, 3H), 12.28 (s, 1H).

Example 43

6-(2,3-dimethoxyphenyl)-4-(1H-pyrrolo[2,3-b]pyridin-3-yl)pyridin-2(1H)-one

Example 43A

3-(2-tert-butoxy-6-(2,3-dimethoxyphenyl)-1,2-dihydropyridin-4-yl)-1H-pyrrolo[2,3-b]pyridine The title compound was prepared using the procedure described for EXAMPLE 34D substituting 2,3 dimethoxyphenylboronic acid for phenyl boronic acid. MS (ESI) m/e 404.1 (M+H)$^+$.

Example 43B

6-(2,3-dimethoxyphenyl)-4-(1H-pyrrolo[2,3-b]pyridin-3-yl)pyridin-2(1H)-one

The title compound was prepared as the trifluoroacetate salt using the procedure described for EXAMPLE 35B substituting EXAMPLE 43A for EXAMPLE 35A. MS (ESI) m/e 347.9 (M+H)$^+$; $^1$H NMR (DMSO-d$_6$) δ 3.68-3.76 (m, 3H), 3.84-3.91 (m, 3H), 6.89 (s, 1H), 6.99 (d, J=1.59 Hz, 1H), 7.11 (dd, J=6.35, 2.78 Hz, 1H), 7.18-7.24 (m, 2H), 7.27 (dd, J=7.93, 4.76 Hz, 1H), 8.25-8.45 (m, 3H), 12.42 (s, 1H).

Example 44

6-(2-fluoro-3-methoxyphenyl)-4-(1H-pyrrolo[2,3-b]pyridin-3-yl)pyridin-2(1H)-one

Example 44A

3-(2-tert-butoxy-6-(2-fluoro-3-methoxyphenyl)pyridin-4-yl)-1H-pyrrolo[2,3-b]pyridine The title compound was prepared using the procedure described for EXAMPLE 34D substituting 2-fluoro-3-methoxyphenylboronic acid for phenyl boronic acid. MS (ESI) m/e 392.0 (M+H)$^+$.

Example 44B

6-(2-fluoro-3-methoxyphenyl)-4-(1H-pyrrolo[2,3-b]pyridin-3-yl)pyridin-2 (1H)-one The title compound was prepared as the trifluoroacetate salt using the procedure described for EXAMPLE 35B substituting EXAMPLE 44A for EXAMPLE 35A. MS (ESI) m/e 335.9 (M+H)$^+$; $^1$H NMR (DMSO-$d_6$) δ 3.90 (s, 3H), 6.64-6.83 (m, 1H), 6.90 (s, 1H), 7.06-7.47 (m, 4H), 8.09-8.54 (m, 3H), 12.30 (s, 1H).

Example 45

6-(4-chloro-2-fluorophenyl)-4-(1H-pyrrolo[2,3-b]pyridin-3-yl)pyridin-2(1H)-one

Example 45A

3-(2-tert-butoxy-6-(4-chloro-2-fluorophenyl)pyridin-4-yl)-1H-pyrrolo[2,3-b]pyridine The title compound was prepared using the procedure described for EXAMPLE 34D substituting 2-fluoro-4-chlorophenylboronic acid for phenyl boronic acid. MS (ESI) m/e 396.0 (M+H)$^+$.

Example 45B

6-(4-chloro-2-fluorophenyl)-4-(1H-pyrrolo[2,3-b]pyridin-3-yl)pyridin-2(1H)-one The title compound was prepared as the trifluoroacetate salt using the procedure described for EXAMPLE 35B substituting EXAMPLE 45A for EXAMPLE 35A. MS (ESI) m/e 339.9 (M+H)$^+$; $^1$H NMR (DMSO-$d_6$) δ 6.77 (s, 1H), 6.95 (s, 1H), 7.22 (dd, J=7.93, 4.76 Hz, 1H), 7.45 (dd, J=8.53, 1.78 Hz, 1H), 7.63 (dd, J=10.31, 1.98 Hz, 1H), 7.76 (t, J=8.33 Hz, 1H), 8.23 (d, J=2.78 Hz, 1H), 8.27-8.41 (m, 2H), 12.11-12.41 (m, 1H).

Example 46

6-[2-methoxy-5-(trifluoromethyl)phenyl]-4-(1H-pyrrolo[2,3-b]pyridin-3-yl)pyridin-2(1H)-one

Example 46A

3-(2-tert-butoxy-6-(2-methoxy-5-(trifluoromethyl)phenyl)pyridin-4-yl)-1H-pyrrolo[2,3-b]pyridine The title compound was prepared using the procedure described for EXAMPLE 34D substituting 2-methoxy-5-(trifluoromethyl)phenylboronic acid for phenyl boronic acid. MS (ESI) m/e 442.1 (M+H)$^+$.

Example 46B

6-(2-methoxy-5-(trifluoromethyl)phenyl)-4-(1H-pyrrolo[2,3-b]pyridin-3-yl)pyridin-2(1H)-one The title compound was prepared as the trifluoroacetate salt using the procedure described for EXAMPLE 35B substituting EXAMPLE 46A for EXAMPLE 35A. MS (ESI) m/e 386.0 (M+H)$^+$; $^1$H NMR (DMSO-$d_6$) δ 3.86-3.98 (m, 3H), 6.73 (d, J=1.36 Hz, 1H), 6.88 (s, 1H), 7.23 (dd, J=7.80, 4.75 Hz, 1H), 7.35 (d, J=9.16 Hz, 1H), 7.83 (d, J=6.10 Hz, 2H), 8.24 (d, J=2.71 Hz, 1H), 8.28-8.39 (m, 2H), 12.27 (s, 1H).

Example 47

2'-methoxy-4-(1H-pyrrolo[2,3-b]pyridin-3-yl)-2,3'-bipyridin-6(1H)-one

Example 47A

3-(2-tert-butoxy-6-(2-methoxypyridin-3-yl)-1,2-dihydropyridin-4-yl)-1H-pyrrolo[2,3-b]pyridine The title compound was prepared using the procedure described for EXAMPLE 34D substituting 2-methoxypyridin-3-ylboronic acid for phenyl boronic acid. MS (ESI) m/e 375.0 (M+H)$^+$.

Example 47B

6-(2-methoxypyridin-3-yl)-4-(1H-pyrrolo[2,3-b]pyridin-3-yl)pyridin-2(1H)-one The title compound was prepared as the trifluoroacetate salt using the procedure described for EXAMPLE 35B substituting EXAMPLE 47A for EXAMPLE 35A. MS (ESI) m/e 318.9 (M+H)$^+$; $^1$H NMR (DMSO-$d_6$) δ 3.84-4.03 (m, 3H), 6.72 (s, 1H), 6.89 (s, 1H), 7.14 (dd, J=7.34, 4.96 Hz, 1H), 7.23 (dd, J=7.93, 4.76 Hz, 1H), 7.97 (dd, J=7.34, 1.78 Hz, 1H), 8.17-8.40 (m, 4H), 12.28 (s, 1H).

Example 48

6-(3-chloro-2-methylphenyl)-4-(1H-pyrrolo[2,3-b]pyridin-3-yl)pyridin-2(1H)-one

Example 48A

3-(2-tert-butoxy-6-(3-chloro-2-methylphenyl)-1,2-dihydropyridin-4-yl)-1H-pyrrolo[2,3-b]pyridine The title compound was prepared using the procedure described for EXAMPLE 34D substituting 2-methyl-3-chlorophenylboronic acid for phenylboronic acid. MS (ESI) m/e 392.0 (M+H)$^+$.

Example 48B

6-(3-chloro-2-methylphenyl)-4-(1H-pyrrolo[2,3-b]pyridin-3-yl)pyridin-2(1H)-one The title compound was prepared as the trifluoroacetate salt using the procedure described for EXAMPLE 35B substituting EXAMPLE 48A for EXAMPLE 35A. MS (ESI) m/e 335.9 (M+H)$^+$; $^1$H NMR (DMSO-d$_6$) δ 2.29-2.39 (m, 3H), 6.62 (s, 1H), 6.70 (s, 1H), 7.21 (dd, J=8.14, 4.75 Hz, 1H), 7.29-7.44 (m, 2H), 7.57 (dd, J=7.80, 1.70 Hz, 1H), 8.22 (d, J=2.71 Hz, 1H), 8.26-8.39 (m, 2H), 11.55 (s, 1H), 12.22 (s, 1H).

Example 49

3'-chloro-2'-methoxy-4-(1H-pyrrolo[2,3-b]pyridin-3-yl)-2,4'-bipyridin-6(1H)-one

Example 49A

3-(6-tert-butoxy-3'-chloro-2'-methoxy-2,4'-bipyridin-4-yl)-1H-pyrrolo[2,3-b]pyridine The title compound was prepared using the procedure described for EXAMPLE 34D substituting 3-chloro-2-methoxy-pyridin-4-ylboronic acid for phenylboronic acid. MS (ESI) m/e 549.1 (M+H)$^+$.

Example 49B

6-(3-chloro-2-methoxypyridin-4-yl)-4-(1H-pyrrolo[2,3-b]pyridin-3-yl)pyridin-2(1H)-one The title compound was prepared as the trifluoroacetate salt using the procedure described for EXAMPLE 35B substituting EXAMPLE 49A for EXAMPLE 35A. MS (ESI) m/e 352.9 (M+H)$^+$; $^1$H NMR (DMSO-d$_6$) δ 4.01 (s, 3H), 6.80 (s, 1H), 6.88 (s, 1H), 7.12-7.31 (m, 2H), 8.17-8.28 (m, 2H), 8.27-8.40 (m, 2H), 12.27 (d, J=1.59 Hz, 1H).

Example 50

6-[3-(morpholin-4-yl)phenyl]-4-(1H-pyrrolo[2,3-b]pyridin-3-yl)pyridin-2(1H)-one

Example 50A

4-(3-(6-tert-butoxy-4-(1H-pyrrolo[2,3-b]pyridin-3-yl)-1,6-dihydropyridin-2-yl)phenyl)morpholine The title compound was prepared using the procedure described for EXAMPLE 34D substituting 3-morpholinophenylboronic acid for phenylboronic acid. MS (ESI) m/e 429.2 (M+H)$^+$.

Example 50B

6-(3-morpholinophenyl)-4-(1H-pyrrolo[2,3-b]pyridin-3-yl)pyridin-2(1H)-one

The title compound was prepared as the trifluoroacetate salt using the procedure described for EXAMPLE 35B substituting EXAMPLE 50A for EXAMPLE 35A. MS (ESI) m/e 373.0 (M+H)$^+$; $^1$H NMR (DMSO-d$_6$) δ 3.22 (d, 4H), 3.77 (d, 4H), 6.76 (d, J=1.59 Hz, 1H), 7.09 (s, 2H), 7.25 (dd, J=8.13, 4.56 Hz, 1H), 7.29-7.43 (m, 3H), 8.14-8.56 (m, 3H), 12.36 (s, 1H).

Example 51

6-[3-(methylsulfonyl)phenyl]-4-(1H-pyrrolo[2,3-b]pyridin-3-yl)pyridin-2(1H)-one

Example 51A

3-(2-tert-butoxy-6-(3-(methylsulfonyl)phenyl)-1,2-dihydropyridin-4-yl)-1H-pyrrolo[2,3-b]pyridine The title compound was prepared using the procedure described for EXAMPLE 34D substituting 3-(methylsulfonyl)phenylboronic acid for phenylboronic acid. MS (ESI) m/e 422.0 (M+H)$^+$.

Example 51B

6-(3-(methylsulfonyl)phenyl)-4-(1H-pyrrolo[2,3-b]pyridin-3-yl)pyridin-2(1H)-one The title compound was prepared as the trifluoroacetate salt using the procedure described for EXAMPLE 35B substituting EXAMPLE 51A for EXAMPLE 35A. MS (ESI) m/e 366.0 (M+H)$^+$; $^1$H NMR (DMSO-d$_6$) δ 3.15-3.44 (s, 3H), 6.85 (s, 1H), 7.24 (dd, J=8.33, 4.76 Hz, 1H), 7.29-7.43 (m, 1H), 7.80 (t, J=7.93 Hz, 1H), 8.01 (d, J=7.93 Hz, 1H), 8.23-8.49 (m, 5H), 12.31 (s, 1H).

Example 52

6-(1H-pyrazol-4-yl)-4-(1H-pyrrolo[2,3-b]pyridin-3-yl)pyridin-2(1H)-one

Example 52A

3-(2-tert-butoxy-6-(1H-pyrazol-4-yl)-1,2-dihydropyridin-4-yl)-1H-pyrrolo[2,3-b]pyridine The title compound was prepared using the procedure described for EXAMPLE 34D substituting 4-(4,4,5,5-tetramethyl-1,3,2-dioxaborolan-2-yl)-1H-pyrazole for phenylboronic acid. MS (ESI) m/e 334.0 (M+H)+.

Example 52B 6-(1H-pyrazol-4-yl)-4-(1H-pyrrolo[2,3-b]pyridin-3-yl)pyridin-2(1H)-one The title compound was prepared as the trifluoroacetate salt using the procedure described for EXAMPLE 35B substituting EXAMPLE 52A for EXAMPLE 35A. MS (ESI) m/e 277.9 (M+H)+; $^1$H NMR (DMSO-d$_6$) δ 6.61 (s, 1H), 7.09 (d, J=1.59 Hz, 1H), 7.24 (dd, J=7.93, 4.76 Hz, 1H), 8.24-8.46 (m, 5H), 12.34 (s, 1H).

Example 53

2'-methyl-4-(1H-pyrrolo[2,3-b]pyridin-3-yl)-2,3'-bipyridin-6(1H)-one

Example 53A 3-(2-tert-butoxy-6-(2-methylpyridin-3-yl)-1,2-dihydropyridin-4-yl)-1H-pyrrolo[2,3-b]pyridine The title compound was prepared using the procedure described for EXAMPLE 34D substituting 2-methylpyridin-3-yl boronic acid for phenylboronic acid and CombiPhos-Pd6 (CombiPhos Catalysts, Inc, Catalog #AC2) for dichlorobis(triphenylphosphine)-palladium (II). MS (DCI) m/e 359.2 (M+H)+.

Example 53B 6-(2-methylpyridin-3-yl)-4-(1H-pyrrolo[2,3-b]pyridin-3-yl)pyridin-2(1H)-one The title compound was prepared as the trifluoroacetate salt using the procedure described for EXAMPLE 35B substituting EXAMPLE 53A for EXAMPLE 35A. MS (ESI) m/e 302.9 (M+H)+; $^1$H NMR (DMSO-d$_6$) δ 2.65-2.78 (m, 3H), 6.89 (d, J=1.36 Hz, 1H), 7.01 (s, 1H), 7.24 (dd, J=7.80, 4.75 Hz, 1H), 7.82 (dd, J=7.97, 5.59 Hz, 1H), 8.27 (d, J=2.71 Hz, 1H), 8.30-8.36 (m, 1H), 8.40 (d, J=8.14 Hz, 2H), 8.80 (dd, J=5.42, 1.70 Hz, 1H), 12.36 (s, 1H).

Example 54

6-[(3-methoxyphenyl)amino]-4-(1H-pyrrolo[2,3-b]pyridin-3-yl)pyridin-2(1H)-one

EXAMPLE 34B (0.2 g, 0.45 mmol), 3-methoxyaniline (0.8 g, 6.5 mmol) and p-toluenesulfonic acid (0.086 g, 0.45 mmol) was heated to 150° C. for 30 minutes in a CEM microwave @100W. The crude material was diluted with a small amount of dichloromethane and placed directly onto a silica gel column and purified (Analogix280, gradient elution, 2-10% methanol/dichloromethane) to give the title compound. MS (ESI) m/e 333.3 (M+H)+; $^1$H NMR (DMSO-d$_6$) δ 3.67-3.84 (m, 3H), 6.28 (s, 1H), 6.49 (d, J=6.71 Hz, 1H), 6.57 (s, 1H), 7.07-7.20 (m, 3H), 7.22 (s, 1H), 7.83 (d, J=2.44 Hz, 1H), 8.17-8.31 (m, 3H), 8.37 (s, 1H), 11.72 (s, 1H).

Example 55

6-anilino-4-(1H-pyrrolo[2,3-b]pyridin-3-yl)pyridin-2 (1H)-one

The title compound was prepared using the procedure described for EXAMPLE 54 substituting aniline for 3-methoxyaniline. MS (ESI) m/e 303.3 (M+H)+; $^1$H NMR (DMSO-d$_6$) δ 6.30 (s, 1H), 6.67 (s, 1H), 6.89 (s, 1H), 7.13-7.33 (m, 4H), 7.66 (s, 1H), 7.97 (d, J=2.03 Hz, 1H), 8.29 (d, J=5.09 Hz, 2H), 8.75 (s, 1H), 10.08 (s, 1H), 12.05 (s, 1H)

Example 56

6-[(trans-4-aminocyclohexyl)amino]-4-(1H-pyrrolo [2,3-b]pyridin-3-yl)pyridin-2(1H)-one

Example 56A 3-(2,6-difluoropyridin-4-yl)-1-(phenylsulfonyl)-1H-pyrrolo[2,3-b]pyridine A suspension of 1-(phenylsulfonyl)-3-(4,4,5,5-tetramethyl-1,3,2-dioxaborolan-2-yl)-1H-pyrrolo[2,3-b]pyridine (7.26 g, 18.9 mmol), 2,6-difluoro-4-iodopyridine (4.14 g, 17.2 mmol, *Eur. J. Org. Chem.*, 2004, 1018 and *Org. Lett.* 2007, 5175), dichlorobis(triphenylphosphine) palladium(II) (0.482 g, 0.687 mmol) and 1M aqueous sodium carbonate (13.7 mL, 13.7 mmol) in dimethoxyethane/ethanol/water (7:2:3) (80 mL) was degassed and heated at 80° C. for 1.5 hours. After cooling, the suspension was filtered, washed with water and ether, and concentrated to give the crude title compound. The filtrate was diluted with water and extracted twice with dichloromethane. The combined organic layers were dried over magnesium sulfate, filtered, concentrated, and purified using an ISCO Companion flash system eluting with dichloromethane/hexane (7:3 to 9:1) to give the title compound. The combined products were used in the next step without further purification.

Example 56B 3-(2,6-difluoropyridin-4-yl)-1H-pyrrolo[2,3-b]pyridine

A mixture of EXAMPLE 56A (8.01 g, 21.6 mmol) and 20% aqueous sodium hydroxide (12 mL, 21.6 mmol) in 1,4-dioxane (75 mL) was heated at 50° C. for 90 minutes. The mixture was concentrated and the residue triturated with water, filtered, and concentrated to give the title compound.

Example 56C trans-N$^1$-(6-fluoro-4-(1H-pyrrolo[2,3-b]pyridin-3-yl)pyridin-2-yl)cyclohexane-1,4-diamine A mixture of EXAMPLE 56B (0.60 g, 2.60 mmol) and trans-cyclohexane-1,4-diamine (1.04 g, 9.08 mmol) in ethanol (10 mL) was heated at in a Biotage Initiator microwave reactor at 170° C. for 80 minutes. After concentration, the residue was treated with 20% brine and extracted twice with ethyl acetate. The combined organic layers were concentrated and purified on a 110 g silica column (KP-NH from Biotage) eluting with ethyl acetate/methanol (97:3 to 90:10) to give the title compound.

Example 56D 6-(trans-4-aminocyclohexylamino)-4-(1H-pyrrolo[2,3-b]pyridin-3-yl)pyridin-2(1H)-one A mixture of EXAMPLE 56C (0.500 g, 1.54 mmol) and concentrated HCl (0.80 mL, 26.3 mmol) in tert-butanol (10 mL) was heated at 140° C. for 40 minutes in a Biotage Initiator microwave reactor. The top layer was decanted and the viscous bottom layer was dissolved in methanol and treated with saturated sodium bicarbonate until at a pH of 4. The solution was concentrated and the residue purified by reversed-phase HPLC on a Zorbax RX-C18 column (250× 21.2 mm, 7 μm particle size) using a gradient of 10-100% acetonitrile/0.1% aqueous trifluoroacetic acid to give the title compound as the trifluoroacetic acid salt. MS (DCI$^+$) m/z 324.2 (M+H)$^+$. $^1$H NMR (DMSO-d$_6$) δ 1.20-1.57 (m, 4H), 1.84-2.13 (m, 4H), 2.94-3.14 (m, 1H), 3.51-3.69 (m, 1H), 6.29 (s, 1H), 6.44 (s, 1H), 7.24 (dd, J=8.1, 4.7 Hz, 1H), 7.88 (d, J=4.3 Hz, 3H), 8.20 (d, J=2.8 Hz, 1H), 8.27 (dd, J=8.2, 1.2 Hz, 1H), 8.33 (dd, J=4.6, 1.5 Hz, 1H), 12.38 (s, 1H).

Example 57

N-(trans-4-{[6-oxo-4-(1H-pyrrolo[2,3-b]pyridin-3-yl)-1,6-dihydropyridin-2-yl]amino}cyclohexyl)cyclopropanesulfonamide A mixture of EXAMPLE 56D (70.0 mg, 0.127 mmol), triethylamine (0.088 mL, 0.64 mmol) and cyclopropanesulfonyl chloride (0.014 mL, 0.14 mmol) in N,N-dimethylformamide (1.5 mL) was stirred at room temperature for 5 hours. Water was added and the suspension was filtered and purified by reversed-phase HPLC to give the title compound as the trifluoroacetic acid salt. MS (DCI$^+$) m/z 428.3 (M+H)$^+$. $^1$H NMR (DMSO-d$_6$) δ 0.89-0.98 (m, 4H), 1.26-1.53 (m, 4H), 1.91-2.04 (m, 4H), 2.54-2.62 (m, 2H), 3.13-3.24 (m, 1H), 6.30 (s, 1H), 6.53 (s, 1H), 7.14 (d, J=7.6 Hz, 1H), 7.27 (dd, J=7.9, 4.6 Hz, 1H), 8.24 (d, J=2.8 Hz, 1H), 8.28 (dd, J=8.1, 1.4 Hz, 1H), 8.34 (dd, J=4.7, 1.4 Hz, 1H), 12.43 (s, 1H).

Example 58

N-(trans-4-{[6-oxo-4-(1H-pyrrolo[2,3-b]pyridin-3-yl)-1,6-dihydropyridin-2-yl]amino}cyclohexyl)cyclopropanecarboxamide A mixture of EXAMPLE 56D (70.0 mg, 0.127 mmol), triethylamine (0.088 mL, 0.64 mmol), N-hydroxybenzotriazole (38.9 mg, 0.254 mmol), 1-ethyl-3-[3-dimethylaminopropyl]carbodiimide hydrochloride (48.7 mg, 0.254 mmol) and cyclopropanecarboxylic acid (0.012 mL, 0.15 mmol) in tetrahydrofuran (2 mL) was stirred at room temperature for 5 hours. The mixture was concentrated and purified by reversed-phase HPLC to give the title compound as a trifluoroacetic acid salt. MS (DCI$^+$) m/z 392.2 (M+H)$^+$; $^1$H NMR (CD$_3$OD) δ 0.69-0.77 (m, 2H), 0.80-0.88 (m, 2H), 1.41-1.61 (m, 5H), 1.95-2.06 (m, 2H), 2.09-2.20 (m, 2H), 3.59-3.75 (m, 2H), 4.80 (s, 1H), 4.91 (s, 1H), 7.34 (dd, J=7.9, 4.9 Hz, 1H), 8.10 (s, 1H), 8.36 (dd, J=4.9, 1.2 Hz, 1H), 8.41 (dd, J=8.1, 1.4 Hz, 1H).

Example 59

1-(4-fluorobenzyl)-N-(trans-4-{[6-oxo-4-(1H-pyrrolo[2,3-b]pyridin-3-yl)-1,6-dihydropyridin-2-yl]amino}cyclohexyl)azetidine-3-carboxamide A mixture of EXAMPLE 56D (70.0 mg, 0.127 mmol), triethylamine (0.088 mL, 0.64 mmol), N-hydroxybenzotriazole (38.9 mg, 0.254 mmol), 1-ethyl-3-[3-dimethylaminopropyl]carbodiimide hydrochloride (48.7 mg, 0.254 mmol) and 1-(4-fluorobenzyl)azetidine-3-carboxylic acid (31.9 mg, 0.152 mmol) in tetrahydrofuran (2 mL) was stirred at room temperature for 5 hours. The reaction mixture was concentrated and purified by reversed-phase HPLC to give the title compound as a trifluoroacetic acid salt. MS (APCI$^+$) m/z 515.5 (M+H)$^+$; $^1$H NMR (DMSO-d$_6$) δ 1.23-1.46 (m, 4H), 1.74-1.93 (m, 2H), 1.94-2.09 (m, 2H), 3.38-4.30 (m, 7H), 4.37 (s, 2H), 6.28 (s, 1H), 6.44 (s, 1H), 7.17 (s, brd, 1H), 7.24 (dd, J=8.1, 4.7 Hz, 1H), 7.30 (t, J=8.9 Hz, 2H), 7.54 (dd, J=8.7, 5.3 Hz, 2H), 8.14 (d, J=7.6 Hz, 1H), 8.20 (d, J=1.8 Hz, 1H), 8.27 (d, J=7.6 Hz, 1H), 8.33 (dd, J=4.7, 1.4 Hz, 1H), 10.30 (s, brd, 1H), 12.39 (s, 1H).

Example 60

2-(4-methylphenyl)-6-(1H-pyrrolo[2,3-b]pyridin-3-yl)pyrimidin-4(3H)-one

The title compound was prepared using the procedure described for EXAMPLE 32 replacing phenylmagnesium bromide with p-tolylmagnesium bromide. MS (ESI) m/e 303 (M+H)$^+$; $^1$H NMR (DMSO-d$_6$) δ 2.41 (s, 3H), 6.74 (s, 1H), 7.24 (dd, J=7.93, 4.88 Hz, 1H), 7.39 (d, J=7.93 Hz, 2H), 8.17 (d, J=7.63 Hz, 2H), 8.31 (dd, J=4.58, 1.53 Hz, 1H), 8.42 (d, J=1.22 Hz, 1H), 8.70 (d, J=7.32 Hz, 1H), 12.31 (s, 1H).

Example 61

2-(3-methylphenyl)-6-(1H-pyrrolo[2,3-b]pyridin-3-yl)pyrimidin-4(3H)-one

The title compound was prepared using the procedure described for EXAMPLE 32 replacing phenylmagnesium bromide with m-tolylmagnesium bromide. MS (ESI) m/e 303 (M+H)$^+$; $^1$H NMR (DMSO-d$_6$) δ 2.44 (s, 3H), 6.76 (s, 1H), 7.25 (dd, J=7.93, 4.88 Hz, 1H), 7.39-7.53 (m, 2H), 8.02-8.14 (m, 2H), 8.31 (dd, J=4.58, 1.53 Hz, 1H), 8.43 (s, 1H), 8.69 (d, J=7.93 Hz, 1H), 12.28 (s, 1H).

Example 62

Chunqiu Lai 2-(2,3-dimethylphenyl)-6-(1H-pyrrolo[2,3-b]pyridin-3-yl)pyrimidin-4 (3H)-one The title compound was prepared using the procedure described for EXAMPLE 32 replacing phenylmagnesium bromide with (2,3-dimethylphenyl)magnesium bromide. MS (ESI) m/e 317 (M+H)$^+$; $^1$H NMR (DMSO-d$_6$) δ 2.29 (s, 3H), 2.34 (s, 3H), 6.73 (s, 1H), 7.16 (dd, J=7.93, 4.88 Hz, 1H), 7.25 (t, J=7.48 Hz, 1H), 7.32-7.38 (m, 2H), 8.27 (dd, J=4.73, 1.37 Hz, 1H), 8.31 (s, 1H), 8.54 (d, J=7.93 Hz, 1H), 12.27 (s, 1H).

Example 63

2-{[3-(3-aminopropoxy)benzyl]amino}-6-(1H-pyrrolo[2,3-b]pyridin-3-yl)pyrimidin-4(3H)-one

Example 63A 3-((4-methoxy-6-(1-(phenylsulfonyl)-1H-pyrrolo[2,3-b]pyridin-3-yl)pyrimidin-2-ylamino)methyl)phenol Example 1B (889 mg, 2.00 mmol), 3-(aminomethyl)phenol (739 mg, 6.00 mmol), triethylamine (0.836 ml, 6.00 mmol) and dioxane (8 ml) were placed in a pressure tube. The mixture was heated at 100° C. overnight. The cooled reaction mixture was concentrated in vacuo. Flash chromatography (gradient elution, ethyl acetate/hexane 5-50%) gave the title compound.

Example 63B tert-butyl 3-(3-((4-methoxy-6-(1-(phenylsulfonyl)-1H-pyrrolo[2,3-b]pyridin-3-yl)pyrimidin-2-ylamino)methyl)phenoxy)propylcarbamate To a mixture of Example 63A (0.510 g, 1.05 mmol), tert-butyl 3-hydroxypropylcarbamate (0.275 g, 1.57 mmol) and triphenylphosphine (0.412 g, 1.57 mmol) in tetrahydrofuran (13 ml) was added dropwise diisopropyl azodicarboxylate (DIAD) (0.305 ml, 1.57 mmol). The reaction mixture was stirred at room temperature for 3 hours and then concentrated in vacuo. Flash chromatography isolation (gradient elution, ethyl acetate/hexane 0-50%) gave the title compound.

Example 63C tert-butyl 3-(3-((4-methoxy-6-(1H-pyrrolo[2,3-b]pyridin-3-yl)pyrimidin-2-ylamino)methyl)phenoxy)propylcarbamate A mixture of Example 63B (600 mg, 0.93 mmol) in methanol (12 mL) and NaOH aqueous solution (1M, 4 mL) was stirred at room temperature for 16 hours. The mixture was filtered, and the solid was washed with water and dried in vacuo to give the title compound.

Example 63D 2-(3-(3-aminopropoxy)benzylamino)-6-(1H-pyrrolo[2,3-b]pyridin-3-yl)pyrimidin-4(3H)-one To Example 63C (297 mg, 0.59 mmol) was added aqueous HCl (12 M, 8.0 ml) and the mixture was heated at 90° C. for 5 hours. The cooled reaction mixture was concentrated in vacuo to give the title compound as an HCl salt. MS (ESI) m/e 391(M+H)$^+$; $^1$H NMR (300 MHz, DMSO-d$_6$) δ ppm 1.94-2.11 (m, 1H) 2.86-3.02 (m, 2H) 4.00-4.11 (m, 2H) 4.58-4.73 (m, 2H) 6.12-6.53 (m, 1H) 6.87 (d, J=8.82 Hz, 1H) 6.96-7.06 (m, 2H) 7.16-7.37 (m, 2H) 7.82-8.10 (m, 3H) 8.35 (s, 1H) 8.50 (d, J=7.80 Hz, 1H) 12.63 (s, 1H).

Example 68

Enzyme Inhibition Data

This example describes the assays that may be used to identify compounds having kinase activity.

Cdc7 (BEV coexpressed huCDC7/DBF4) is prepared internally. Cdc7 assays are conducted as follows with final concentrations as listed. In 384-well v-bottom polypropylene plates, 6 μL compound (2% DMSO), is mixed with 6 μL of Cdc7 (2 ug/mL), and Jerini peptide substrate A-All (biotin-C$_6$linker-TPSDSLIYDDGLS) (2 μM), followed by immediate initiation with 6 μL λ-[$^{33}$P]-ATP (1 μM, 20 mCi/μmol) using a reaction buffer comprising 25 mM HEPES, pH 7.5, 1 mM DTT, 10 mM MgCl$_2$, 100 μM Na$_3$VO$_4$, 0.075 mg/ml Triton X-100. Reactions are quenched after 1 hr by the addition of 90 μL stop buffer (50 mM EDTA, 2M NaCl). 85 μL, of the stopped reactions are transferred to 384-well streptavidin-coated plates (FlashPlate Plus, Perkin Elmer), incubated 30 minutes at room temperature and washed 3 times with 0.05% Tween-20/PBS using an ELX-405 automated plate washer (BioTek), and counted on a TopCount Scintillation Plate Reader (Packard). IC50 values are determined via non-linear regression fitting of enzyme inhibition data and corresponding Ki values are generated assuming ATP-competitive (equilibrium) inhibition and using the experimentally determined apparent ATP Km of 0.7 μM (as determined using the above assay condition, but varying ATP).

Table 1 depicts enzyme inhibition data (K$_i$) for exemplary compounds. In Table 1, "A" represents a K$_i$ of less than 10 nM and "B" represents a K$_i$ of between 10 nM and 100 nM.

TABLE 1

| Example | Cdc7 Inhibition |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |

Compounds of the present invention assessed by the above-described assays were found to have Cdc7 kinase-inhibiting activity.

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A compound having formula (I)

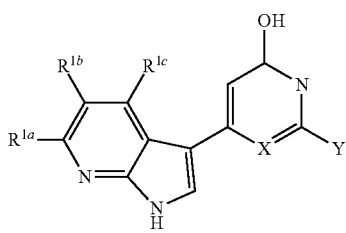

Formula (I)

wherein $R^{1a}$, $R^{1b}$ and $R^{1c}$ are independently hydrogen, hydroxy, nitro, halogen, cyano, trifluoromethyl, trifluoromethoxy, $C_{1-4}$-alkyl, —$OR^a$, —$NR^bR^c$; —$C(O)OR^a$, —$C(O)NR^bR^c$, —$NR^bC(O)R^c$, —$NHC(O)NHR^b$, or —$NHSO_2R^a$;

X is N;

$R^2$ is hydrogen or $C_{1-4}$-alkyl;

Y is $NR^3R^4$, $NR^6C(O)R^2$, $NR^6SO_2R^2$, aryl, or heterocyclyl, wherein the aryl and heterocyclyl are optionally substituted with one or more $R^5$;

$R^3$ is hydrogen, $C_{1-8}$-alkyl, $C_{2-8}$-alkenyl, $C_{2-8}$-alkynyl, $C_{3-8}$-cycloalkyl, $C_{3-8}$-cycloalkyl-($C_{1-8}$-alkyl)-, heterocycloalkyl, heterocycloalkyl-($C_{1-8}$-alkyl)-, aryl, aryl-($C_{1-8}$-alkyl)-, heteroaryl-, or heteroaryl-($C_{1-8}$-alkyl), wherein (a) the $R^3C_{1-8}$-alkyl, $C_{2-8}$-alkenyl, $C_{2-8}$-alkynyl substituents, alone or as part of another group, are optionally substituted with one or more substituents selected from the group consisting of halogen, cyano, nitro, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, —$SO_2NR^bNR^c$, and aryl; and (b) the $R^3C_{3-8}$-cycloalkyl, heterocycloalkyl, aryl, and heteroaryl, alone or as part of another group, are optionally substituted with one or more $R^5$;

$R^4$ is hydrogen or $C_{1-8}$-alkyl; wherein the $C_{1-8}$-alkyl is optionally substituted with one or more substituents selected from the group consisting of halogen, cyano, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$;

$R^5$ is selected from the group consisting of $C_{1-8}$-alkyl, $C_{2-8}$-alkenyl, $C_{2-8}$-alkynyl, aryl, heterocyclyl, halogen, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$NHSO_2R^e$, —$C(O)NR^eR^f$, —$SR^d$, —$S(O)R^d$, —$SO_2R^d$, —$SO_2NR^eNR^f$, —$B(OH)_2$, —$CF_3$, —$CF_2CF_3$, —$OCF_3$, and —$OCF_2CF_3$ wherein (a) the $R^5C_{1-8}$-alkyl, $C_{2-8}$-alkenyl, $C_{2-8}$-alkynyl, substituents are optionally substituted with one or more substituents selected from the group consisting of aryl, heterocyclyl, $C_{3-8}$-cycloalkyl, halogen, cyano, nitro, —$OR^d$, $C(O)R^d$, $C(O)OR^d$, —$OC(O)R^d$, —$NR^eR^f$, —$NR^eC(O)R^d$, —$NHC(O)NHR^e$, —$C(O)NR^eR^f$; and wherein (b) the $R^5$ aryl or heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, —$OR^g$, —$C(O)R^g$, —$C(O)OR^g$, —$OC(O)R^g$, —$NR^hR^i$, —$NR^hC(O)R^g$, —$NHC(O)NHR^h$, —$NHSO_2R^g$, —$C(O)NR^hR^i$, —$SR^g$, —$S(O)R^g$, —$SO_2R^g$, —$SO_2NR^hNR^i$, —$CF_3$, —$CF_2CF_3$, —$OCF_3$, and —$OCF_2CF_3$;

$R^6$ is hydrogen or $C_{1-8}$-alkyl;

$R^7$ is $C_{1-8}$-alkyl, $C_{2-8}$-alkenyl, $C_{2-8}$-alkynyl, $C_{3-8}$-cycloalkyl, $C_{3-8}$-cycloalkyl-($C_{1-8}$-alkyl)-, heterocycloalkyl, heterocycloalkyl-($C_{1-8}$-alkyl)-, aryl, aryl-($C_{1-8}$-alkyl)-, heteroaryl-, or heteroaryl-($C_{1-8}$-alkyl)-, wherein (a) the $R^7C_{1-8}$-alkyl, $C_{2-8}$-alkenyl, $C_{2-8}$-alkynyl substituents, alone or as part of another group, are optionally substituted with one or more substituents selected from the group consisting of halogen, cyano, nitro, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, —$SO_2NR^6NR^e$, and aryl; and (b) the $R^7C_{3-8}$-cycloalkyl, heterocycloalkyl, aryl, and heteroaryl, alone or as part of another group, are optionally substituted with one or more $R^5$;

$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), —O ($C_{1-8}$-alkyl)$NH_2$, and —$N(C_{1-8}$-alkyl)$_2$;

$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^b$ and $R^c$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, aryl-($C_{1-8}$-alkyl)-, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$; wherein the aryl, aryl-($C_{1-8}$-alkyl), heterocyclyl, and $C_{3-8}$-cycloalkyl, alone or as part of another group, are optionally substituted with one or more substituents independently selected from the group consisting of $C_{1-8}$-alkyl, aryl, heterocyclyl, $C_{3-8}$- cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^e$ and $R^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^e$ and $R^f$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^g$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^i$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

or a pharmaceutically acceptable salt thereof.

2. The compound of claim 1, wherein $R^{1a}$, $R^{1b}$, and $R^{1c}$ are hydrogen.

3. The compound of claim 1, wherein Y is $NR^3R^4$.

4. The compound of claim 3, wherein $R^3$ is $C_{1-8}$-alkyl, wherein the $C_{1-8}$-alkyl is optionally substituted with one or two $R^5$.

5. The compound of claim 3, wherein $R^3$ is aryl or heteroaryl, wherein the aryl and heteroaryl are optionally substituted with one or more $R^5$.

6. The compound of claim 3, wherein $R^3$ is $C_{3-8}$-cycloalkyl or heterocycloalkyl, wherein the $C_{3-8}$-cycloalkyl or heterocycloalkyl are optionally substituted with one or more $R^5$.

7. The compound of claim 3, wherein $R^3$ is $C_{3-8}$-cycloalkyl($C_{1-8}$-alkyl), heterocycloalkyl($C_{1-8}$-alkyl), aryl-($C_{1-8}$-alkyl), or heteroaryl($C_{1-8}$-alkyl), wherein the $R^3C_{3-8}$-cycloalkyl, heterocycloalkyl, aryl, and heteroaryl are optionally substituted with one or more $R^5$.

8. The compound of claim 3, wherein $R^4$ is hydrogen or methyl.

9. The compound of claim 1, wherein Y is heterocyclyl, wherein the heterocyclyl is optionally substituted with one or more $R^5$.

10. The compound of claim 1, wherein Y is aryl, wherein the aryl is optionally with one or more $R^5$.

11. The compound of claim 1 wherein $R^{1a}$, $R^{1b}$, and $R^{1c}$ are hydrogen, X is N, Y is $NR^3R^4$, wherein $R^3$ is $C_{3-8}$-cycloalkyl, wherein the $C_{3-8}$-cycloalkyl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, and wherein $R^d$, $R^e$, and $R^f$ are independently selected from the group consisting of hydrogen, $C_{1-8}$-alkyl, and $C_{3-8}$-cycloalkyl.

12. The compound of claim 1 wherein $R^{1a}$, $R^{1b}$ and $R^{1c}$ are hydrogen, X is N, Y is $NR^3R^4$, wherein $R^3$ is aryl, wherein the aryl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

13. The compound of claim 1 wherein $R^{1a}$, $R^{1b}$ and $R^{1c}$ are hydrogen, X is N, Y is $NR^3R^4$, wherein $R^3$ is aryl-($C_{1-8}$-alkyl), wherein the aryl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

14. The compound of claim 1 wherein $R^{1a}$, $R^{1b}$ and $R^{1c}$ are hydrogen, X is N, Y is $NR^3R^4$, wherein $R^3$ is heterocycloalkyl, wherein the heterocycloalkyl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

15. The compound of claim 1 wherein $R^{1a}$, $R^{1b}$, and $R^{1c}$ are hydrogen, X is N, Y is $NR^3R^4$, wherein $R^3$ is heterocycloalkyl-($C_{1-8}$-alkyl)-, wherein the heterocycloalkyl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

16. The compound of claim 1 wherein $R^{1a}$, $R^{1b}$, and $R^{1c}$ are hydrogen, X is N, Y is heterocyclyl, wherein the heterocyclyl is optionally substituted with one or more substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

17. The compound of claim 1 wherein $R^{1a}$, $R^{1b}$, and $R^{1c}$ are hydrogen, X is N, Y is $NR^3R^4$, wherein $R^3$ is heteroaryl-($C_{1-8}$-alkyl), wherein the aryl is optionally substituted with one or two substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

18. The compound of claim 1 wherein $R^{1a}$, $R^{1b}$, and $R^{1c}$ are hydrogen, X is N, Y is aryl, wherein the aryl is optionally substituted with one or more substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

19. The compound of claim 1 wherein $R^{1a}$, $R^{1b}$, and $R^{1c}$ are hydrogen, X is N, Y is heteroaryl, wherein the heteroaryl is optionally substituted with one or more substituents independently selected from the group consisting of $C_{1-8}$-alkyl, heterocyclyl, halogen, —$OR^d$, —$C(O)OR^d$, —$NR^eR^f$, —$NR^eC(O)R^d$, —$NHSO_2R^e$, —$SO_2R^d$, —$CF_3$, and —$OCF_3$ wherein the $C_{1-8}$-alkyl is optionally substituted with one or more —$OR^d$, wherein $R^4$ is hydrogen or $C_{1-8}$-alkyl, and wherein $R^d$, $R^e$, and $R^f$ are independently selected from the group consisting of hydrogen, $C_{1-8}$-alkyl, and $C_{3-8}$-cycloalkyl.

20. The compound of claim 1 which is
2-(cyclohexylamino)-6-(1H-pyrrolo[2,3-b]pyridin-3-yl)pyrimidin-4(3H)-one;
2-(benzylamino)-6-(1H-pyrrolo[2,3-b]pyridin-3-yl)pyrimidin-4(3H)-one;
2-anilino-6-(1H-pyrrolo[2,3-b]pyridin-3-yl)pyrimidin-4(3H)-one;
2-[(trans-4-aminocyclohexyl)amino]-6-(1H-pyrrolo[2,3-b]pyridin-3-yl)pyrimidin-4(3H)-one;
2-[(3,5-difluorobenzyl)amino]-6-(1H-pyrrolo[2,3-b]pyridin-3-yl)pyrimidin-4(3H)-one;
2-(piperidin-4-ylamino)-6-(1H-pyrrolo[2,3-b]pyridin-3-yl)pyrimidin-4(3H)-one;
2-(4-hydroxypiperidin-1-yl)-6-(1H-pyrrolo[2,3-b]pyridin-3-yl)pyrimidin-4(3H)-one;
2-{[(1S)-1-phenylethyl]amino}-6-(1H-pyrrolo[2,3-b]pyridin-3-yl)pyrimidin-4(3H)-one;
6-(1H-pyrrolo[2,3-b]pyridin-3-yl)-2-(tetrahydro-2H-pyran-4-ylamino)pyrimidin-4(3H)-one;
6-(1H-pyrrolo[2,3-b]pyridin-3-yl)-2-[(tetrahydrofuran-2-ylmethyl)amino]pyrimidin-4(3H)-one;
2-[cyclohexyl(methyl)amino]-6-(1H-pyrrolo[2,3-b]pyridin-3-yl)pyrimidin-4(3H)-one;
2-{[(1R)-1-phenylethyl]amino}-6-(1H-pyrrolo[2,3-b]pyridin-3-yl)pyrimidin-4(3H)-one;
2-[(2-aminocyclohexyl)amino]-6-(1H-pyrrolo[2,3-b]pyridin-3-yl)pyrimidin-4(3H)-one;
2-(cycloheptylamino)-6-(1H-pyrrolo[2,3-b]pyridin-3-yl)pyrimidin-4(3H)-one;
6-(1H-pyrrolo[2,3-b]pyridin-3-yl)-2-(thiomorpholin-4-yl)pyrimidin-4(3H)-one;
2-{[2-(methylamino)ethyl]amino}-6-(1H-pyrrolo[2,3-b]pyridin-3-yl)pyrimidin-4(3H)-one;
2-[bis(2-methoxyethyl)amino]-6-(1H-pyrrolo[2,3-b]pyridin-3-yl)pyrimidin-4(3H)-one;
2-[(2-methoxyethyl)amino]-6-(1H-pyrrolo[2,3-b]pyridin-3-yl)pyrimidin-4(3H)-one;
2-[(2-hydroxyethyl)amino]-6-(1H-pyrrolo[2,3-b]pyridin-3-yl)pyrimidin-4(3H)-one;
6-(1H-pyrrolo[2,3-b]pyridin-3-yl)-2-{[2-(trifluoromethyl)benzyl]amino}pyrimidin-4(3H)-one;
2-[4-(hydroxymethyl)piperidin-1-yl]-6-(1H-pyrrolo[2,3-b]pyridin-3-yl)pyrimidin-4(3H)-one;
2-{[3-(morpholin-4-yl)propyl]amino}-6-(1H-pyrrolo[2,3-b]pyridin-3-yl)pyrimidin-4(3H)-one;
2-[(3-hydroxybenzyl)amino]-6-(1H-pyrrolo[2,3-b]pyridin-3-yl)pyrimidin-4(3H)-one;
2-(morpholin-4-yl)-6-(1H-pyrrolo[2,3-b]pyridin-3-yl)pyrimidin-4(3H)-one;
1-[6-oxo-4-(1H-pyrrolo[2,3-b]pyridin-3-yl)-1,6-dihydropyrimidin-2-yl]piperidine-4-carboxylic acid;
2-(cyclopentylamino)-6-(1H-pyrrolo[2,3-b]pyridin-3-yl)pyrimidin-4(3H)-one;
2-(4-methoxypiperidin-1-yl)-6-(1H-pyrrolo[2,3-b]pyridin-3-yl)pyrimidin-4(3H)-one;
2-[(2-hydroxycyclohexyl)amino]-6-(1H-pyrrolo[2,3-b]pyridin-3-yl)pyrimidin-4(3H)-one;
2-[(1-methylpiperidin-4-yl)amino]-6-(1H-pyrrolo[2,3-b]pyridin-3-yl)pyrimidin-4(3H)-one;
2-{[3-(1H-imidazol-1-yl)propyl]amino}-6-(1H-pyrrolo[2,3-b]pyridin-3-yl)pyrimidin-4(3H)-one;
2-({2-[2-(2-aminoethoxy)ethoxy]ethyl}amino)-6-(1H-pyrrolo[2,3-b]pyridin-3-yl)pyrimidin-4(3H)-one;
2-phenyl-6-(1H-pyrrolo[2,3-b]pyridin-3-yl)pyrimidin-4(3H)-one;
2-(2-methylphenyl)-6-(1H-pyrrolo[2,3-b]pyridin-3-yl)pyrimidin-4(3H)-one;
2-(4-methylphenyl)-6-(1H-pyrrolo[2,3-b]pyridin-3-yl)pyrimidin-4(3H)-one;
2-(3-methylphenyl)-6-(1H-pyrrolo[2,3-b]pyridin-3-yl)pyrimidin-4(3H)-one;
2-(2,3-dimethylphenyl)-6-(1H-pyrrolo[2,3-b]pyridin-3-yl)pyrimidin-4(3H)-one; or
2-{[3-(3-aminopropoxy)benzyl]amino}-6-(1H-pyrrolo[2,3-b]pyridin-3-yl)pyrimidin-4(3H)-one.

21. A pharmaceutical composition comprising a compound or pharmaceutically acceptable salt of claim 1 and pharmaceutically acceptable excipient.

* * * * *

UNITED STATES PATENT AND TRADEMARK OFFICE
CERTIFICATE OF CORRECTION

PATENT NO.       : 9,181,246 B2
APPLICATION NO.  : 14/444540
DATED            : November 10, 2015
INVENTOR(S)      : Penning et al.

Page 1 of 1

It is certified that error appears in the above-identified patent and that said Letters Patent is hereby corrected as shown below:

In the claims

Column 89, line 23, claim 1: " 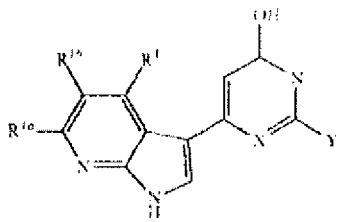 " to read as 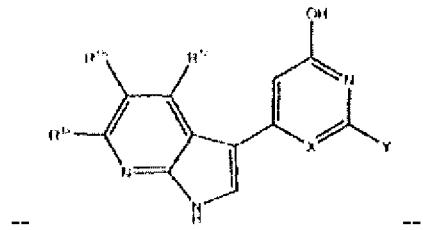 --

Column 89, line 38, claim 1: "$NR^6C(O)R^2$, $NR^6SO_2R^2$," to read as --$NR^6C(O)R^7$, $NR^6SO_2R^7$,--

Column 90, line 27, claim 1: "$NHC(O)NHR^h$," to read as --$NHC(O)NHR^b$,--

Column 90, line 28, claim 1: "$SO_2NR^6NR^e$," to read as --$SO_2NR^6NR^c$,--

Column 91, line 60, claim 10: "the aryl is optionally with" to read as --the aryl is optionally substituted with--

Signed and Sealed this
Twenty-third Day of August, 2016

Michelle K. Lee
*Director of the United States Patent and Trademark Office*